United States Patent
Maresca et al.

(10) Patent No.: US 11,254,928 B2
(45) Date of Patent: Feb. 22, 2022

(54) GENE MODIFICATION ASSAYS

(71) Applicant: ASTRAZENECA AB, Södertälje (SE)

(72) Inventors: Marcello Maresca, Södertälje (SE); Amir Taheri-Ghahfarokhi, Södertälje (SE); Mohammad Bohlooly-Yeganeh, Södertälje (SE); Lorenz M. Mayr, Södertälje (SE)

(73) Assignee: ASTRAZENECA AB, Södertälje (SE)

( * ) Notice: Subject to any disclaimer, the term of this patent is extended or adjusted under 35 U.S.C. 154(b) by 609 days.

(21) Appl. No.: 16/070,406

(22) PCT Filed: Jan. 13, 2017

(86) PCT No.: PCT/IB2017/000106
§ 371 (c)(1),
(2) Date: Jul. 16, 2018

(87) PCT Pub. No.: WO2017/122096
PCT Pub. Date: Jul. 20, 2017

(65) Prior Publication Data
US 2019/0024074 A1   Jan. 24, 2019

Related U.S. Application Data

(60) Provisional application No. 62/279,337, filed on Jan. 15, 2016.

(51) Int. Cl.
| | | |
|---|---|---|
| *C12N 15/11* | (2006.01) | |
| *C12N 15/85* | (2006.01) | |
| *C12N 15/87* | (2006.01) | |
| *C12N 15/90* | (2006.01) | |
| *C12N 5/074* | (2010.01) | |
| *C12N 15/10* | (2006.01) | |
| *C12N 15/63* | (2006.01) | |
| *C12N 5/0735* | (2010.01) | |

(52) U.S. Cl.
CPC ......... *C12N 15/102* (2013.01); *C12N 5/0606* (2013.01); *C12N 5/0696* (2013.01); *C12N 15/111* (2013.01); *C12N 15/63* (2013.01); *C12N 15/85* (2013.01); *C12N 15/87* (2013.01); *C12N 15/907* (2013.01); *C12N 2310/20* (2017.05); *C12N 2320/10* (2013.01); *C12N 2320/12* (2013.01)

(58) Field of Classification Search
CPC .............. C12N 15/111; C12N 2310/20; C12N 2320/10; C12N 15/85; C12N 9/22; C12N 15/87; C12N 15/102; C12N 15/90; C12N 15/00–15/907; C12Y 301/21–301/21007
See application file for complete search history.

(56) References Cited

U.S. PATENT DOCUMENTS

2014/0045176 A1   2/2014   Kim et al.

FOREIGN PATENT DOCUMENTS

| WO | 2015/006294 A2 | 1/2015 | |
|---|---|---|---|
| WO | 2015/123339 A1 | 8/2015 | |
| WO | WO-2017107898 A2 * | 6/2017 | ........... C12N 15/113 |

OTHER PUBLICATIONS

Ramakrishna et al. Surrogate reporter-based enrichment of cells containing RNA-guided Cas9 nuclease-induced mutations. Nature Communications, vol. 5, 3378, Feb. 26, 2014, printed as pp. 1-10, including pp. 1-22 of Supplementary Data. (Year: 2014).*
Sander et al. CRISPR-Cas systems for editing, regulating and targeting genomes. Nature Biotechnology, vol. 32, No. 4, pp. 347-355, Mar. 2, 2014. (Year: 2014).*
Makarova et al. An updated evolutionary classification of CRISPR-Cas systems. Nature Reviews Microbiology, vol. 13, pp. 722-736, Sep. 28, 2015. (Year: 2015).*
Chu et al. Tracking genome engineering outcome at individual DNA breakpoints. Nature Biotechnology, vol. 33, No. 5, pp. 543-548, Mar. 24, 2015, including pp. 1/2-2/2 of Online Methods, and pp. 1/20-20/20 of Supplementary Text and Figures. (Year: 2015).*
Bitinate et al., "FokI dimerization is required for DNA cleavage," Proc Natl Acad Sci USA 95:10570-10575 (1998).
Boch et al., "Breaking the Code of DNA Binding Specificity of TAL-Type III Effectors," Science 326(5959):1509-1512 (2009).
Boch, "TALEs of genome targeting," Nat Biotechnol 29(2):135-136 (2011).
Cathomen et al., "Zinc-finger nucleases: the next generation emerges," Mol Ther 16(7):1200-1207 (2008).
Christian et al., "Targeting DNA Double-Strand Breaks with TAL Effector Nucleases," Genetics 186:757-761 (2010).
He et al., "Comparison of surrogate reporter systems for enrichment of cells with mutations induced by genome editors," J Biotechnol 221:49-54 (2016).
Kim et al., "Hybrid restriction enzymes: Zinc finger fusions to Fok I cleavage domain," Proc Natl Acad Sci USA 93:1156-1160 (1996).
Kim et al., "Surrogate reporters for enrichment of cells with nuclease-induced mutations," Nat Methods 8(11):941-943 (2011).
Kim et al., "A guide to genome engineering with programmable nucleases," Nat Rev Genet 15(5):321-334 (2014).
Koike-Yusa et al., "Genome-wide recessive genetic screening in mammalian cells with a lentiviral CRISPR-guide RNA library," Nat Biotechnol 32(3):267-273 (2014).
Mali et al., "RNA-Guided Human Genome Engineering via Cas9," Science 339(6121):823-826 (2013).

(Continued)

*Primary Examiner* — Jennifer Dunston
(74) *Attorney, Agent, or Firm* — Medler, Ferro, Woodhouse & Mills PLLC

(57) ABSTRACT

Provided herein, in some embodiments, are nucleic acid-based tools that may be used for high-throughput functional genomics studies as well as for the generation of knockout (gene inactivation or deletion) or knockin (gene activation or insertion) cell lines. Tools of the present disclosure include an "activatable reporter cassette," a guide RNA construct and a nuclease that can be used together, for example, to modify and isolate targeted cells of interest.

20 Claims, 32 Drawing Sheets
Specification includes a Sequence Listing.

(56) References Cited

OTHER PUBLICATIONS

Maresca et al., "Obligate ligation-gated recombination (ObLiGaRe): custom-designed nuclease-mediated targeted integration through nonhomologous end joining," Genome Res 23(3):539-546 (2013).
Miller et al., "A TALE nuclease architecture for efficient genome editing," Nat Biotechnol 29(2):143-148 (2011).
Moscou et al., "A Simple Cipher Governs DNA Recognition by TAL Effectors," Science 326(5959):1501 (2009).
Sander et al., "CRISPR-Cas systems for editing, regulating and targeting genomes," Nature Biotechnol 32(4):347-355 (2014).
Shalem et al., "Genome-Scale CRISPR-Cas9 Knockout Screening in Human Cells," Science 343(6166):84-47 (2014).
Wang et al., "Genetic screens in human cells using the CRISPR/Cas9 system," Science 343(6166):80-84 (2014).
Zetsche et al., "Cpf1 is a single RNA-guided Endonuclease of a class 2 CRISPR-Cas system," Cell 163(3):759-771 (2015).
Zhou et al., "High-throughput screening of a CRISPR/Cas9 library for functional genomics in human cells," Nature 509(7501):487-91 (2014).
Brooks et al., "Transcriptional silencing is associated with extensive methylation of the CMV promoter following adenoviral gene delivery to muscle," J. Gene Med. 6:395-404 (2004).
Hong et al., "Methylation of episomal plasmids as a barrier to transient gene expression via a synthetic delivery vector," Biomolecular Engineering. 18:185-192 (2001).

\* cited by examiner

Fig. 5B

Sequencing results for '- BSD Cr1': 16%

```
TGCACAAGATGGATGATCGTCCAGAGGAACG    WT (31x)
TGCACAAGATGGATGATCGTCGTC-AGAGGAACG  Δ1 (2x)
TGCACAAGATGGATGATCGTC--------CG     Δ8
TG--------------------------AACG    Δ25
TGCACAAGATGGATGATCGTCCaAGAGGAAC     +1
TGCACAAGATGGATGATCGTCtCAGAGGAACG    G>a, C>t
                                    n = 37
```

Sequencing results for '+BSD Cr1': 67%

```
TGCACAAGATGGATGATCGTCCAGAGGAACG     WT (11x)
TGCACAAGATGGATGATCGT-CAGGAACG       Δ1 (3x)
TGCACAAGATGGATGATC--CAGAGGAACG      Δ2
TGCACAAGATGGATGATC---CAGAGGAACG     Δ3
TGCACAAGATGGAT-------CAGAGGAACG     Δ7
TGCACAAGAT----------CG              Δ9 (3x)
TGCACAAGAT----------CAGAGGAACG      Δ11
TGCACAAGA-----------CAGAGGAACG      Δ12
TGCACAAGAT-----------AGAGGAACG      Δ12
TGCACAAGATGG---------GGAACG         Δ13
TGCACAAGA------------GAGAGGAACG     Δ14
TGCACAAGA------------GGAACG         Δ15
TGCACAAGA-------------GGAACG        Δ16
TGCACAAGATGGATGATCGTC-CAGAGGAACG    Δ251
TGCACAAGATGGATGATCGTC-CAGAGGAACG    Δ262
TGCACAAGATGGATGATCGTCtCAGAGGAAC     +1
TGCACAAGATGGATGATCGTCtCAGAGGAAC     +1
TGCACAAGATGGATGATCGTCtCAGAGGAAC     +1
TGCACAAGATGGATGATCGTCggtgatccta     +143
                                    n = 33
```

TARGET-sequencePAM    (Δ): deletions    (+): insertions

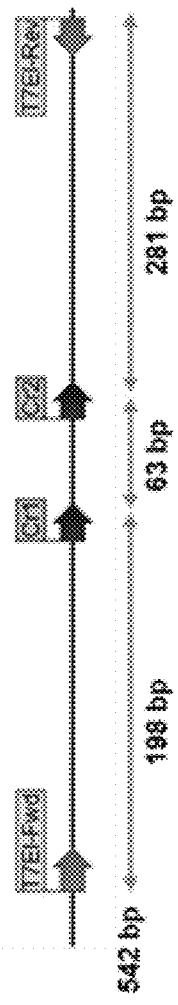

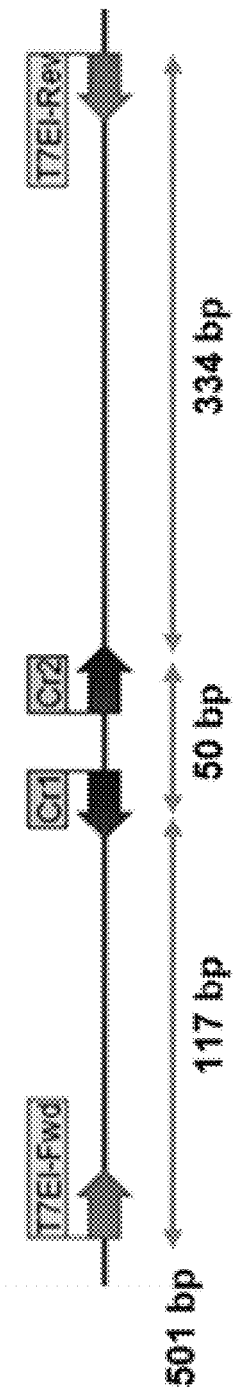

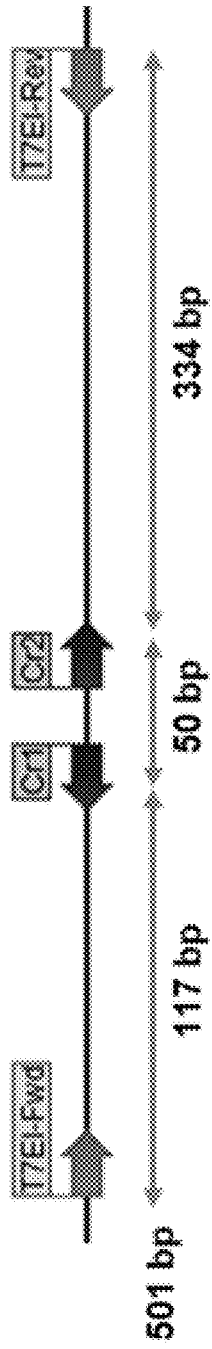

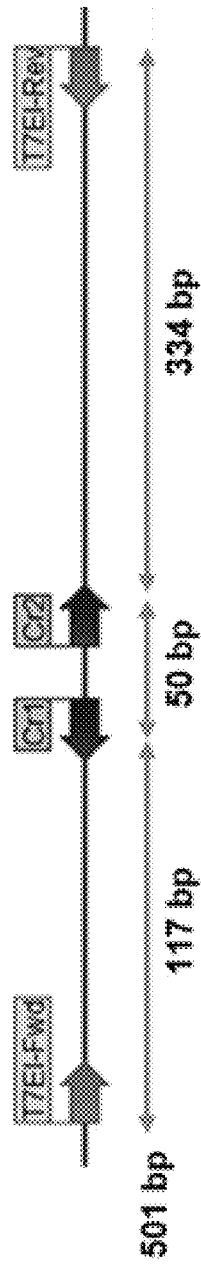

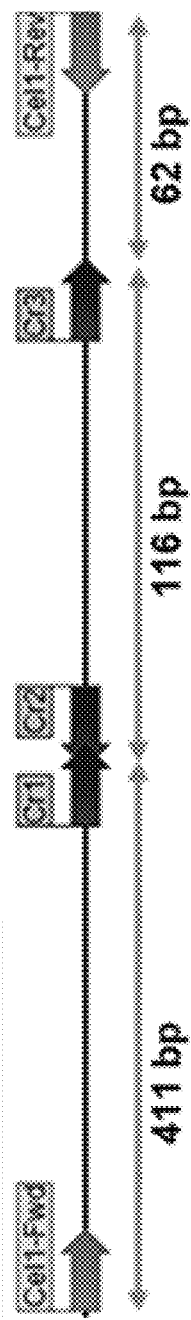
Fig. 11A
Fig. 11B

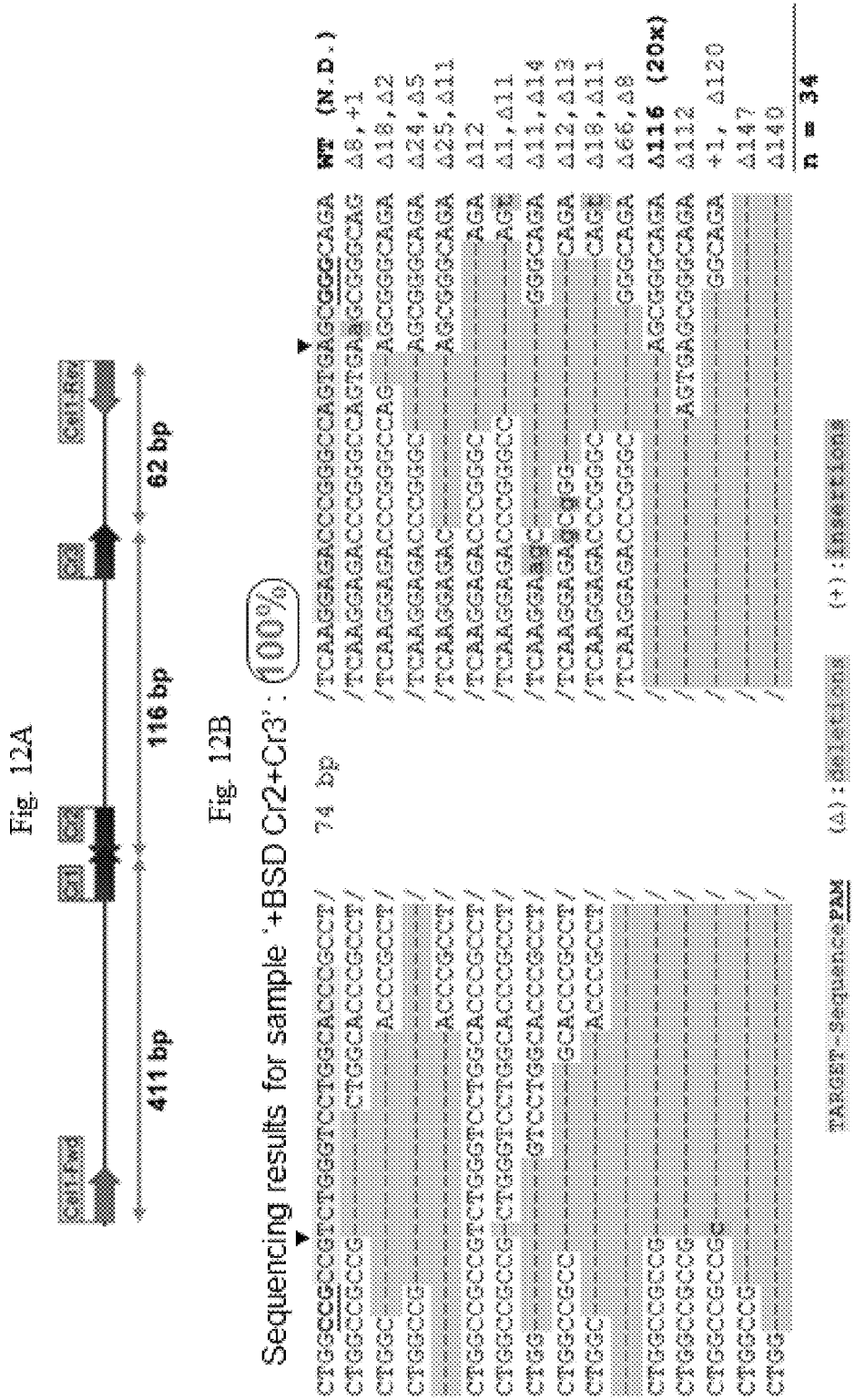

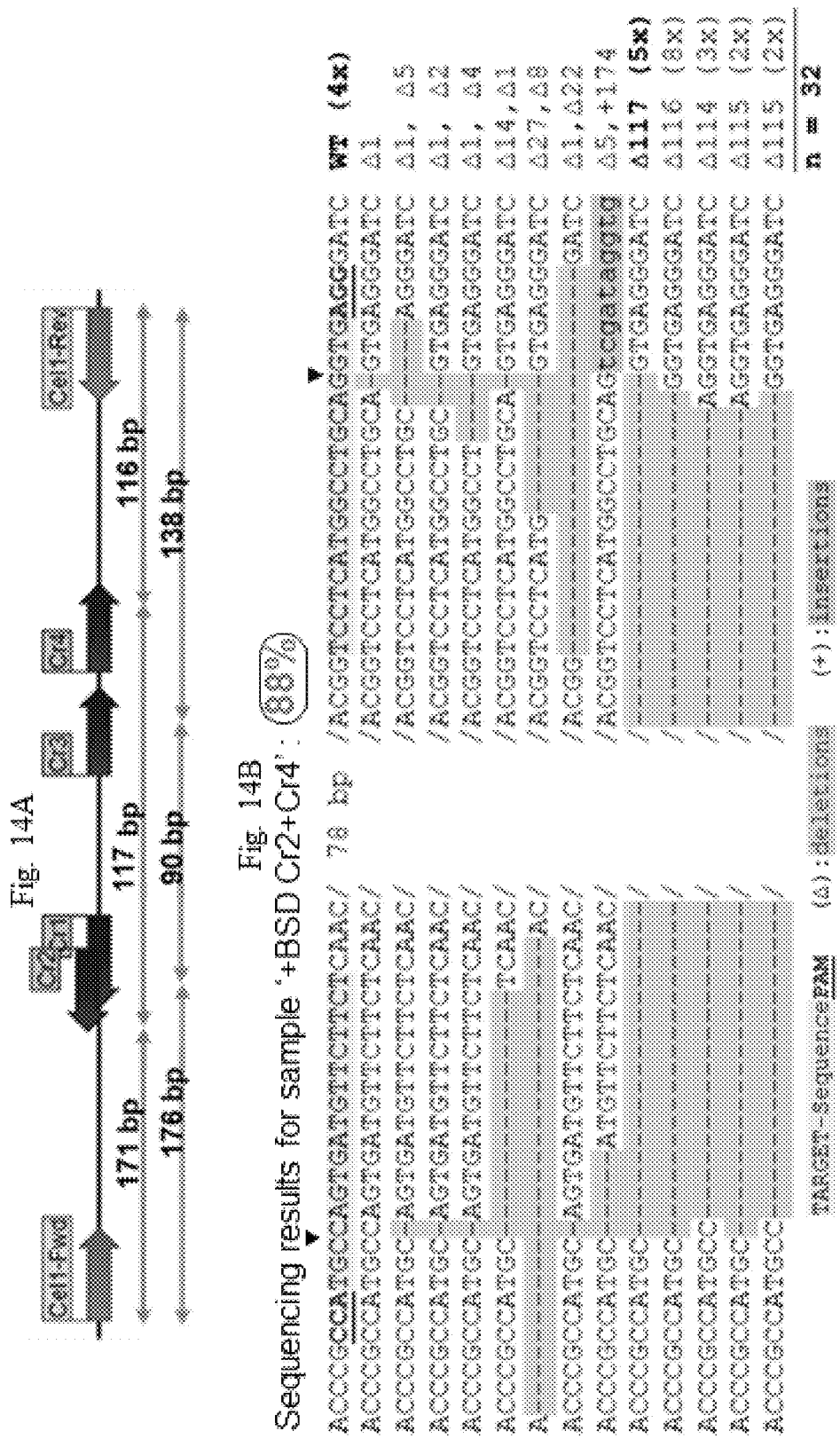

Fig. 19

Fig. 25C
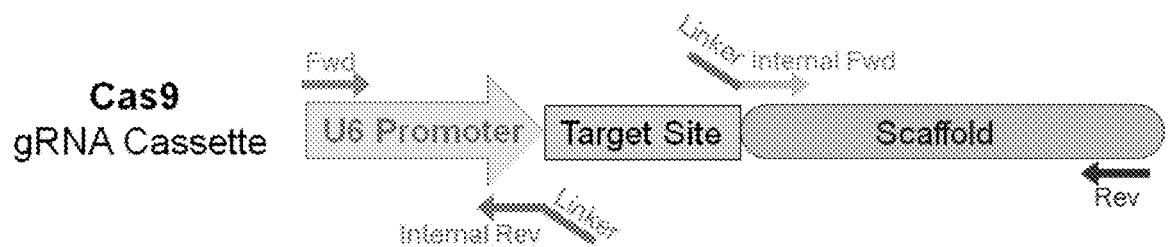
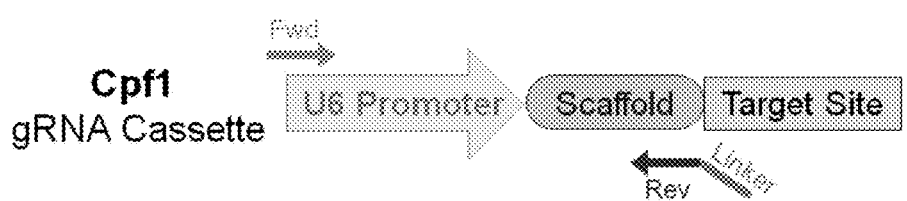
Fig. 26A
Fig. 26B
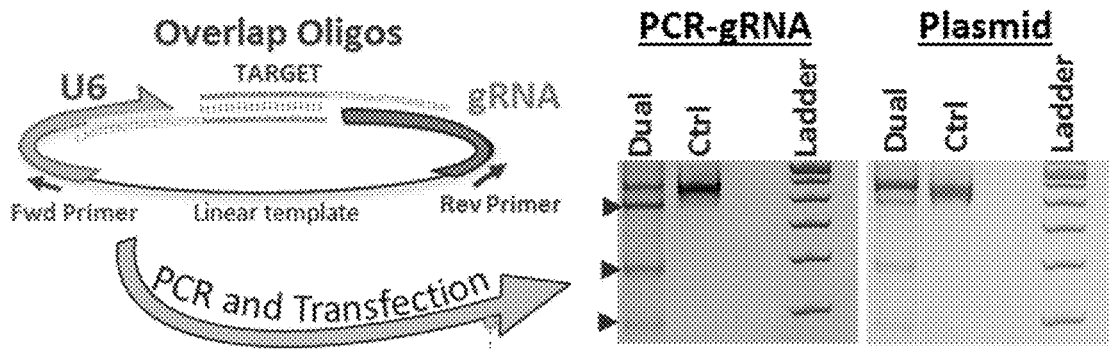
Fig. 27A
Fig. 27B
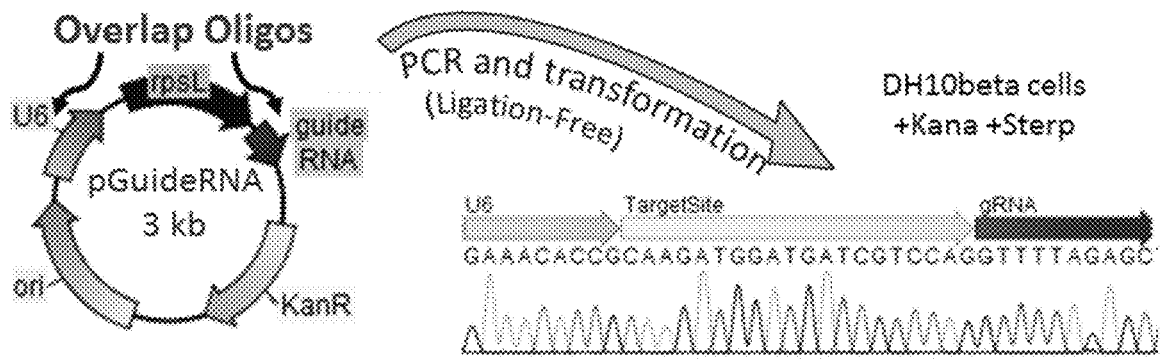

Fig. 31
30% starting confluency
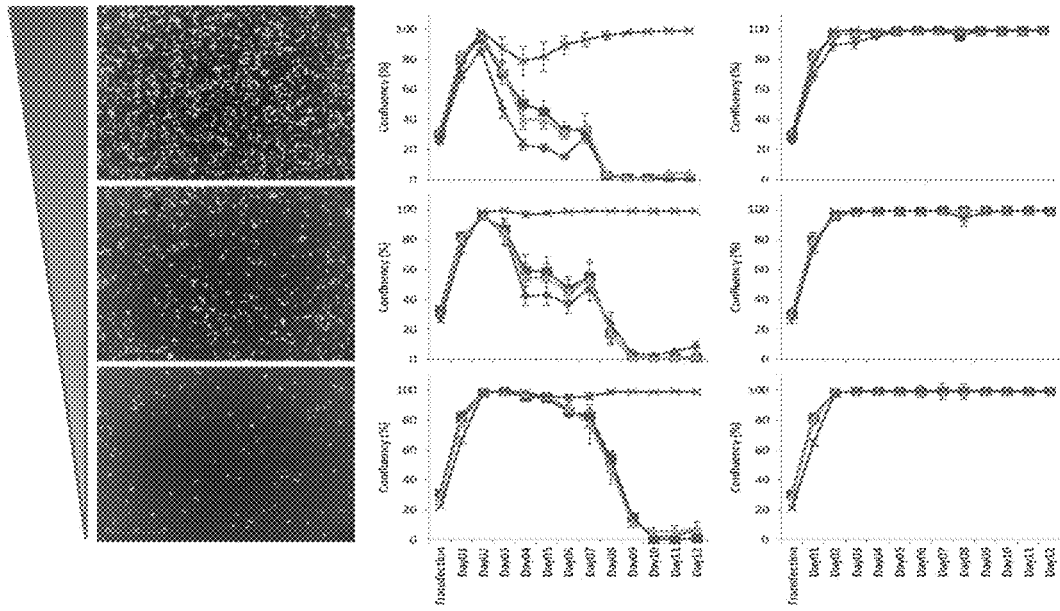
50% starting confluency
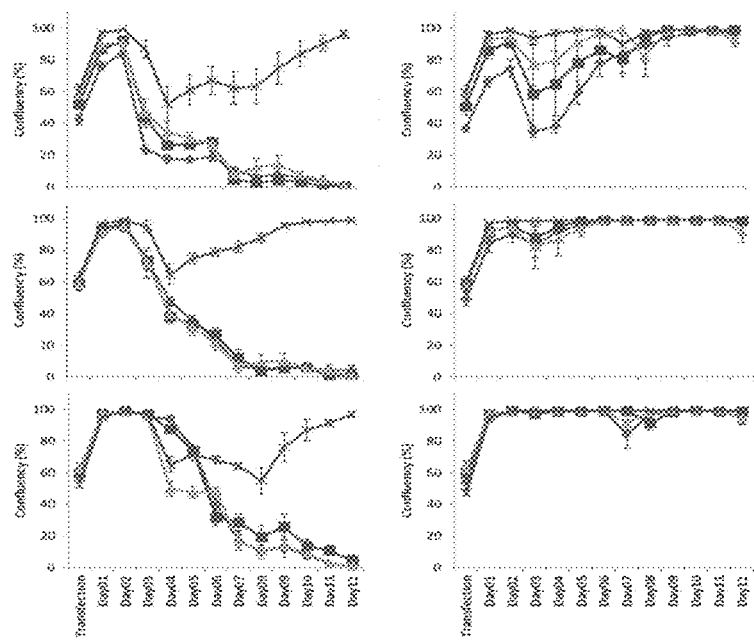
→ Alu Cr1  → Alu Cr2  → Alu Cr3  → AAVS1

SEQUENCE LISTING

```
<160> NUMBER OF SEQ ID NOS: 167

<210> SEQ ID NO 1
<211> LENGTH: 31
<212> TYPE: DNA
<213> ORGANISM: Unknown
<220> FEATURE:
```

```
<223> OTHER INFORMATION: Description of Unknown:
      MAP3K1 sequence

<400> SEQUENCE: 1
tgcacaagat ggatgatcgt ccagaggaac g                                    31

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tgcacaagat ggatgatcgt cagaggaacg                                      30

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tgcacaagat ggatgatcgt ccg                                             23

<210> SEQ ID NO 4
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4 tgaacg                                                                 6

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tgcacaagat ggatgatcgt cccagaggaa c                                    31

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tgcacaagat ggatgatcat tcagaggaac g                                    31

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 7
tgcacaagat ggatgatcgt cagaggaacg                                         30

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tgcacaagat ggatgatcgt cgaggaacg                                          29

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tgcacaagat ggatgatcca gaggaacg                                           28

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tgcacaagat ggatcagagg aacg                                               24

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tgcacaagat ggatgatcgt cg                                                 22

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tgcacaagat cagaggaacg                                                    20

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 13
tgcacaagac agaggaacg                                                    19

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tgcacaagat agaggaacg                                                    19

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tgcacaagat ggggaacg                                                     18

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tgcacaagag aggaacg                                                      17

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tgcacaagat ggaacg                                                       16

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tgcacaagag gaacg                                                        15

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 19
tgcacaagat ggatgatcgt c                                         21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgcacaagat ggatgatcgt c                                         21

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tgcacaagat ggatgatcgt ctcagaggaa c                              31

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tgcacaagat ggatgatcgt cacagaggaa c                              31

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tgcacaagat ggatgatcgt cccagaggaa c                              31

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tgcacaagat ggatgatcgt cggtgactct c                              31

<210> SEQ ID NO 25
<211> LENGTH: 31
<212> TYPE: DNA
<213> ORGANISM: Unknown
<220> FEATURE:
<223> OTHER INFORMATION: Description of Unknown:
      MAP3K1 sequence

<400> SEQUENCE: 25
```

```
tgccagcctg aagcacgaa tggttggaaa g                              31
```

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26

```
tgccagcctg gaagcacgaa ag                                       22
```

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27

```
tgccagcctg gaagcacgaa ttggttggaa a                             31
```

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28

```
tgccagcctg gaagcacgaa tttggaaag                                29
```

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29

```
tgccagcctg gaagcacgaa gttggaaag                                29
```

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30

```
tgccagcctg gaagcacgaa ttggaaag                                 28
```

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tgccagcctg aagcacggt tggaaag                27

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tgccagcctg aagcacgaa tgaaag                 26

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tgccagcctg aatggttgg aaag                   24

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tgccagcctg aagcacgaa g                      21

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tgccagcctg gttggaaag                        19

<210> SEQ ID NO 36
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tgccagcctg gaaag                            15

<210> SEQ ID NO 37
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tgcttggaaa g                                11

<210> SEQ ID NO 38
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38 ttggaaag                                                                  8

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tgccagcctg gaagcac                                                       17

<210> SEQ ID NO 40

<400> SEQUENCE: 40

000

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tgccagcctg gaagcacgaa t                                                  21

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tgccagctgt ggttggaaag                                                    20

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tgccagcctg gaagcacgaa ttggttggaa a                                       31

<210> SEQ ID NO 44
<211> LENGTH: 94
<212> TYPE: DNA
<213> ORGANISM: Unknown
<220> FEATURE:

<223> OTHER INFORMATION: Description of Unknown:
      MAK3K1 sequence
<220> FEATURE:
<221> NAME/KEY: modified_base
<222> LOCATION: (32)..(63)
<223> OTHER INFORMATION: a, c, t, g, unknown or other

<400> SEQUENCE: 44
tgcacaagat ggatgatcgt ccagaggaac gnnnnnnnnn nnnnnnnnnn nnnnnnnnn      60 nnntgccagc ctggaagcac gaatggttgg aaag      94

<210> SEQ ID NO 45
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(39)
<223> OTHER INFORMATION: a, c, t, g, unknown or other

<400> SEQUENCE: 45
tgcacaagat gnnnnnnnnn nnnnnnnnnn nnnnnnnnnt gccggttgga aag      53

<210> SEQ ID NO 46
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tgcacaagat ggatgatcgt cggttggaaa g      31

<210> SEQ ID NO 47
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tgcacaagat ggatgatcgt ctggttggaa ag      32

<210> SEQ ID NO 48
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tgcacaagat ggatgatcgt cggttggaaa g      31

<210> SEQ ID NO 49
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tgcacaagat ggatgattgt cggttggaaa g        31

<210> SEQ ID NO 50
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tgcacaagat ggatgatcgt gggttggaaa g        31

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tgcacaagat ggatgatcgt ccggttggaa ag        32

<210> SEQ ID NO 52
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tgcacaagat ggatgatcgt catggttgga aag        33

<210> SEQ ID NO 53
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tgcacaagat ggatgatcgt ctggttggaa ag        32

<210> SEQ ID NO 54
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54 gttggaaag        9

<210> SEQ ID NO 55
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55 ttggaaag 8

<210> SEQ ID NO 56
<211> LENGTH: 94
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (32)..(63)
<223> OTHER INFORMATION: a, c, t, g, unknown or other

<400> SEQUENCE: 56
tggcggattc agtaaacggg gtcattagtt cnnnnnnnnn nnnnnnnnnn nnnnnnnnn    60 nnngcccata tatggagttc cgcgggttgg aaag                              94

<210> SEQ ID NO 57
<211> LENGTH: 31
<212> TYPE: DNA
<213> ORGANISM: Unknown
<220> FEATURE:
<223> OTHER INFORMATION: Description of Unknown:
    AAVS1 sequence

<400> SEQUENCE: 57
agaacctgga ggtggtgcgc ttcttggtgg a                                 31

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 58
agaacctggg gtggtgcgct tcttggtgga                                   30

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 59
agaacctgga gtggtgcgct tcttggtgga                                   30

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 60
agaacctggt ggtgcgcttc ttggtgga                                     28

<210> SEQ ID NO 61
<211> LENGTH: 25
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 61
agaacctggt gcgcttcttg gtgga                                          25

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
agaacctgga cgcttcttgg tgga                                           24

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
aggtggtgcg cttcttggtg ga                                             22

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
aggtggtgcg cttcttggtg ga                                             22

<210> SEQ ID NO 65
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tgcgcttctt ggtgga                                                    16

<210> SEQ ID NO 66
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66 agaacctgg                                                             9

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 67
agaacctggt gcttcttggt gga                                        23

<210> SEQ ID NO 68
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
agaactgcat tgatggtgcg cttcttggtg g                               31

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
agaacctgga gtggtgcgct tcttggtgga                                 30

<210> SEQ ID NO 70
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
agaacctggt ggtgcgcttc ttggtgga                                   28

<210> SEQ ID NO 71
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
agaacctgga gcgcttcttg gtgga                                      25

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
agaacctgga cttcttggtg ga                                         22

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 73
agaacctgga ttcttggtgg a                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ggtggtgcgc ttcttggtgg a                                              21

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
agaacctgga tcttggtgga                                                20

<210> SEQ ID NO 76
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76 agaacctgg                                                             9

<210> SEQ ID NO 77
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gcttcttggt gga                                                       13

<210> SEQ ID NO 78
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
agaacctgga gggtggtgcg cttcttggtg g                                   31

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 79
gggtggtgcg cttcttggtg g        21

<210> SEQ ID NO 80
<211> LENGTH: 31
<212> TYPE: DNA
<213> ORGANISM: Unknown
<220> FEATURE:
<223> OTHER INFORMATION: Description of Unknown:
      AAVS1 sequence

<400> SEQUENCE: 80
ccactgtgaa ccaggcagac aacgagggct g        31

<210> SEQ ID NO 81
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ccactgtgaa ccaggcagac gagggctg        28

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ccactgtgaa cgagggctg        19

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ccactgtgaa ccaggcctg        19

<210> SEQ ID NO 84
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ccactgtgaa ccaggcagac aaacgagggc t        31

<210> SEQ ID NO 85
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ccactgtgaa ccaggcagac gagggctg                                          28

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ccactgtgaa ccaggcagac                                                   20

<210> SEQ ID NO 87
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ccactgtgaa ccag                                                         14

<210> SEQ ID NO 88
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ccactgtgaa ccaggcagac aaacgagggc t                                      31

<210> SEQ ID NO 89
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ccactgtgaa ccaggcagac aggaaggggc a                                      31

<210> SEQ ID NO 90
<211> LENGTH: 70
<212> TYPE: DNA
<213> ORGANISM: Unknown
<220> FEATURE:
<223> OTHER INFORMATION: Description of Unknown:
      AAVS1 sequence

<400> SEQUENCE: 90
agaacctgga ggtggtgcgc ttcttggtgg agcagggcgc cactgtgaac caggcagaca       60
acgagggctg                                                              70

<210> SEQ ID NO 91
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 91
agaacggtgg tgcgcttctt ggtggagcag ggcgccactg tgaaccaacg agggctg         57

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
agaacctgga aacgagggct g                                                21

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
agaacctgga gaacgagggc tg                                               22

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
agaacctgga gcgagggctg                                                  20

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
agaacctgga ggacgagggc tg                                               22

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
agaacctgga acgagggctg                                                  20

<210> SEQ ID NO 97
<211> LENGTH: 149
<212> TYPE: DNA
<213> ORGANISM: Unknown
<220> FEATURE:
<223> OTHER INFORMATION: Description of Unknown:
      GFAP sequence
<220> FEATURE:
<221> NAME/KEY: modified_base
```

```
<222> LOCATION: (32)..(116)
<223> OTHER INFORMATION: a, c, t, g, unknown or other

<400> SEQUENCE: 97
ggggcctggc tcctggccgc cgtctgggtc cnnnnnnnnn nnnnnnnnnn nnnnnnnnn      60 nnnnnnnnnn nnnnnnnnnn nnnnnnnnnn nnnnnnnnnn nnnnnnnnnn nnnnnnttca    120
aggagacccg ggccagtgag cgggcagag                                       149

<210> SEQ ID NO 98
<211> LENGTH: 147
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (32)..(116)
<223> OTHER INFORMATION: a, c, t, g, unknown or other

<400> SEQUENCE: 98
ggggcctggc tcctggccgc cgtctgggtc cnnnnnnnnn nnnnnnnnnn nnnnnnnnn      60 nnnnnnnnnn nnnnnnnnnn nnnnnnnnnn nnnnnnnnnn nnnnnnnnnn nnnnnnttca    120
aggagacccg ggccagtgcg ggcagag                                         147

<210> SEQ ID NO 99
<211> LENGTH: 143
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (32)..(116)
<223> OTHER INFORMATION: a, c, t, g, unknown or other

<400> SEQUENCE: 99
ggggcctggc tcctggccgc cgtctgggtc cnnnnnnnnn nnnnnnnnnn nnnnnnnnn      60 nnnnnnnnnn nnnnnnnnnn nnnnnnnnnn nnnnnnnnnn nnnnnnnnnn nnnnnnttca    120
aggagacccg ggccagtgca gag                                             143

<210> SEQ ID NO 100
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (32)..(116)
<223> OTHER INFORMATION: a, c, t, g, unknown or other

<400> SEQUENCE: 100
ggggcctggc tcctggccgc cgtctgggtc cnnnnnnnnn nnnnnnnnnn nnnnnnnnn      60 nnnnnnnnnn nnnnnnnnnn nnnnnnnnnn nnnnnnnnnn nnnnnnnnnn nnnnnnttca    120
aggagacccg ggccagtgag                                                 140

<210> SEQ ID NO 101
<211> LENGTH: 138
<212> TYPE: DNA
<213> ORGANISM: Artificial Sequence
```

```
<220> FEATURE:
<223> OTHER INFORMATION: Description of Artificial Sequence: Synthetic
      polynucleotide
<220> FEATURE:
<221> NAME/KEY: modified_base
<222> LOCATION: (32)..(116)
<223> OTHER INFORMATION: a, c, t, g, unknown or other

<400> SEQUENCE: 101
ggggcctggc tcctggccgc cgtctgggtc cnnnnnnnnn nnnnnnnnnn nnnnnnnnnn      60
nnnnnnnnnn nnnnnnnnnn nnnnnnnnnn nnnnnnnnnn nnnnnnnnnn nnnnnnttca     120
aggagacccg ggccagtg                                                   138

<210> SEQ ID NO 102
<211> LENGTH: 138
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (32)..(116)
<223> OTHER INFORMATION: a, c, t, g, unknown or other

<400> SEQUENCE: 102
ggggcctggc tcctggccgc cgtctgggtc cnnnnnnnnn nnnnnnnnnn nnnnnnnnnn      60
nnnnnnnnnn nnnnnnnnnn nnnnnnnnnn nnnnnnnnnn nnnnnnnnnn nnnnnnttca     120
aggagacccg ggccagag                                                   138

<210> SEQ ID NO 103
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (32)..(116)
<223> OTHER INFORMATION: a, c, t, g, unknown or other

<400> SEQUENCE: 103
ggggcctggc tcctggccgc cgtctgggtc cnnnnnnnnn nnnnnnnnnn nnnnnnnnnn      60
nnnnnnnnnn nnnnnnnnnn nnnnnnnnnn nnnnnnnnnn nnnnnnnnnn nnnnnnttca     120
aggagacccg ggcagag                                                    137

<210> SEQ ID NO 104
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (32)..(116)
<223> OTHER INFORMATION: a, c, t, g, unknown or other

<400> SEQUENCE: 104
ggggcctggc tcctggccgc cgtctgggtc cnnnnnnnnn nnnnnnnnnn nnnnnnnnnn      60
nnnnnnnnnn nnnnnnnnnn nnnnnnnnnn nnnnnnnnnn nnnnnnnnnn nnnnnnttca     120
aggagacccg ggccagt                                                    137
```

<210> SEQ ID NO 105
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ggggcctggc tcctggccgc cgagcgggca gag                                    33

<210> SEQ ID NO 106
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106 gcagag                                                                   6

<210> SEQ ID NO 107
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
ggggcctggc tcctggccgc cgagtgagcg ggcagag                                37

<210> SEQ ID NO 108
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (32)..(112)
<223> OTHER INFORMATION: a, c, t, g, unknown or other

<400> SEQUENCE: 108
ggggcctggc tcctggccgc cgtctgggtc cnnnnnnnnn nnnnnnnnnn nnnnnnnnnn        60
nnnnnnnnnn nnnnnnnnnn nnnnnnnnnn nnnnnnnnnn nnnnnnnnnn nnttcaagga      120
gacccgggcc atctctgcgg gcaga                                            145

<210> SEQ ID NO 109
<211> LENGTH: 149
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (32)..(116)
<223> OTHER INFORMATION: a, c, t, g, unknown or other

<400> SEQUENCE: 109
ggggcctggc tcctggccgc cgtctgggtc cnnnnnnnnn nnnnnnnnnn nnnnnnnnnn        60
nnnnnnnnnn nnnnnnnnnn nnnnnnnnnn nnnnnnnnnn nnnnnnnnnn nnnnnnttca      120

```
aggagacccg ggccagtggc aaacaacag                                      149
```

<210> SEQ ID NO 110
<211> LENGTH: 149
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (32)..(116)
<223> OTHER INFORMATION: a, c, t, g, unknown or other

<400> SEQUENCE: 110

```
ggggcctggc tcctggccgc cgtctgggtc cnnnnnnnnn nnnnnnnnnn nnnnnnnnnn     60
nnnnnnnnnn nnnnnnnnnn nnnnnnnnnn nnnnnnnnnn nnnnnnnnnn nnnnnnttca    120
aggagacccg ggccagtgcc aagtctcca                                      149
```

<210> SEQ ID NO 111
<211> LENGTH: 136
<212> TYPE: DNA
<213> ORGANISM: Unknown
<220> FEATURE:
<223> OTHER INFORMATION: Description of Unknown:
      GFAP sequence
<220> FEATURE:
<221> NAME/KEY: modified_base
<222> LOCATION: (32)..(105)
<223> OTHER INFORMATION: a, c, t, g, unknown or other

<400> SEQUENCE: 111

```
ctggccgccg tctgggtcct ggcacccgcc tnnnnnnnnn nnnnnnnnnn nnnnnnnnnn     60
nnnnnnnnnn nnnnnnnnnn nnnnnnnnnn nnnnnnnnnn nnnnntcaag gagacccggg    120
ccagtgagcg ggcaga                                                    136
```

<210> SEQ ID NO 112
<211> LENGTH: 128
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (24)..(97)
<223> OTHER INFORMATION: a, c, t, g, unknown or other

<400> SEQUENCE: 112

```
ctggccgccg ctggcacccg cctnnnnnnn nnnnnnnnnn nnnnnnnnnn nnnnnnnnnn     60
nnnnnnnnnn nnnnnnnnnn nnnnnnnnnn nnnnnntca aggagacccg ggccagtgaa    120
gcgggcag                                                             128
```

<210> SEQ ID NO 113
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (14)..(87)
<223> OTHER INFORMATION: a, c, t, g, unknown or other

<400> SEQUENCE: 113
ctggcacccg cctnnnnnnn nnnnnnnnnn nnnnnnnnnn nnnnnnnnnn nnnnnnnnnn    60
nnnnnnnnnn nnnnnnnnnn nnnnnntca aggagacccg ggccagagcg ggcaga          116

<210> SEQ ID NO 114
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (8)..(81)
<223> OTHER INFORMATION: a, c, t, g, unknown or other

<400> SEQUENCE: 114
ctggccgnnn nnnnnnnnn nnnnnnnnnn nnnnnnnnnn nnnnnnnnnn nnnnnnnnnn    60
nnnnnnnnnn nnnnnnnnnn ntcaaggaga cccgggcagc gggcaga                  107

<210> SEQ ID NO 115
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (9)..(82)
<223> OTHER INFORMATION: a, c, t, g, unknown or other

<400> SEQUENCE: 115
acccgcctnn nnnnnnnnn nnnnnnnnnn nnnnnnnnnn nnnnnnnnnn nnnnnnnnnn    60
nnnnnnnnnn nnnnnnnnnn nntcaaggag acagcgggca ga                       102

<210> SEQ ID NO 116
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (32)..(105)
<223> OTHER INFORMATION: a, c, t, g, unknown or other

<400> SEQUENCE: 116
ctggccgccg tctgggtcct ggcacccgcc tnnnnnnnn nnnnnnnnnn nnnnnnnnnn    60
nnnnnnnnnn nnnnnnnnnn nnnnnnnnnn nnnnnnnnnn nnnntcaag gagacccggg    120 caga                                                                 124

<210> SEQ ID NO 117
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (31)..(104)
<223> OTHER INFORMATION: a, c, t, g, unknown or other

<400> SEQUENCE: 117

```
ctggccgccg ctgggtcctg gcacccgcct nnnnnnnnnn nnnnnnnnnn nnnnnnnnnn     60
nnnnnnnnnn nnnnnnnnnn nnnnnnnnnn nnnnnnnnnn nnnntcaagg agacccgggc    120
cagt                                                                 124

<210> SEQ ID NO 118
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (21)..(94)
<223> OTHER INFORMATION: a, c, t, g, unknown or other

<400> SEQUENCE: 118
ctgggtcctg gcacccgcct nnnnnnnnnn nnnnnnnnnn nnnnnnnnnn nnnnnnnnnn     60
nnnnnnnnnn nnnnnnnnnn nnnnnnnnnn nnnntcaagg aagcgggcag a             111

<210> SEQ ID NO 119
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (20)..(93)
<223> OTHER INFORMATION: a, c, t, g, unknown or other

<400> SEQUENCE: 119
ctggccgccg cacccgcctn nnnnnnnnnn nnnnnnnnnn nnnnnnnnnn nnnnnnnnnn     60
nnnnnnnnnn nnnnnnnnnn nnnnnnnnnn nnntcaagga gagcgggcag a             111

<210> SEQ ID NO 120
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (14)..(87)
<223> OTHER INFORMATION: a, c, t, g, unknown or other

<400> SEQUENCE: 120
ctggcacccg cctnnnnnnn nnnnnnnnnn nnnnnnnnnn nnnnnnnnnn nnnnnnnnnn     60
nnnnnnnnnn nnnnnnnnnn nnnnnnntca aggagacccg ggccagt                  107

<210> SEQ ID NO 121
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(39)
<223> OTHER INFORMATION: a, c, t, g, unknown or other

<400> SEQUENCE: 121
nnnnnnnnnn nnnnnnnnnn nnnnnnnnnn nnnnnnnnnt caaggagacc cgggcgggca     60
```

-continued ga                                                                  62

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ctggccgccg agcgggcaga                                               20

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ctggccgccg agtgagcggg caga                                          24

<210> SEQ ID NO 124
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ctggccgccg cggcaga                                                  17

<210> SEQ ID NO 125
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125 ctggccg                                                              7

<210> SEQ ID NO 126
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126 ctgg                                                                 4

<210> SEQ ID NO 127
<211> LENGTH: 110
<212> TYPE: DNA
<213> ORGANISM: Unknown
<220> FEATURE:
<223> OTHER INFORMATION: Description of Unknown:
      BCL6 sequence
<220> FEATURE:
<221> NAME/KEY: modified_base
<222> LOCATION: (32)..(80)

<223> OTHER INFORMATION: a, c, t, g, unknown or other

<400> SEQUENCE: 127
catgccagtg atgttcttct caaccttaat cnnnnnnnnn nnnnnnnnnn nnnnnnnnnn    60
nnnnnnnnnn nnnnnnnnnn tgagcagttt agagcccata aaacggtcct              110

<210> SEQ ID NO 128
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (31)..(79)
<223> OTHER INFORMATION: a, c, t, g, unknown or other

<400> SEQUENCE: 128
catgccagta tgttcttctc aaccttaatc nnnnnnnnnn nnnnnnnnnn nnnnnnnnnn    60
nnnnnnnnnn nnnnnnnnnt gagcagttta gagcccataa aacggtcct               109

<210> SEQ ID NO 129
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(65)
<223> OTHER INFORMATION: a, c, t, g, unknown or other

<400> SEQUENCE: 129
catgccagtg ataatcnnnn nnnnnnnnnn nnnnnnnnnn nnnnnnnnnn nnnnnnnnnn    60
nnnnntgagc agtcct                                                    76

<210> SEQ ID NO 130
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(59)
<223> OTHER INFORMATION: a, c, t, g, unknown or other

<400> SEQUENCE: 130
catgccagtc nnnnnnnnnn nnnnnnnnnn nnnnnnnnnn nnnnnnnnnn nnnnnnnnt    60 gagcagttta gagcccataa aacggtcct                                      89

<210> SEQ ID NO 131
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(69)
<223> OTHER INFORMATION: a, c, t, g, unknown or other

<400> SEQUENCE: 131
catgccagtg aaccttaatc nnnnnnnnnn nnnnnnnnnn nnnnnnnnnn nnnnnnnnnn        60
nnnnnnnnnt gagcagttta gagccaaacg gtcct                                  95

<210> SEQ ID NO 132
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(74)
<223> OTHER INFORMATION: a, c, t, g, unknown or other

<400> SEQUENCE: 132
catgccagtg ttctcaacct taatcnnnnn nnnnnnnnnn nnnnnnnnnn nnnnnnnnnn        60
nnnnnnnnnn nnnntgagca gtttagagca aacggtcct                              99

<210> SEQ ID NO 133
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
catgccaatg ttcttctcaa ccttaaaaac ggtcct                                 36

<210> SEQ ID NO 134
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(56)
<223> OTHER INFORMATION: a, c, t, g, unknown or other

<400> SEQUENCE: 134
catgccagtg nnnnnnnnnn nnnnnnnnnn nnnnnnnnnn nnnnnnnnnn nnnnntgag        60 cagtttagag cccataaaaa cggtcc                                            86

<210> SEQ ID NO 135
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (32)..(80)
<223> OTHER INFORMATION: a, c, t, g, unknown or other

<400> SEQUENCE: 135
atgccagtga atgttcttct caaccttaat cnnnnnnnnn nnnnnnnnnn nnnnnnnnnn        60
nnnnnnnnnn nnnnnnnnnn tgagcagttt agagcccata aaacggtcct                  110

<210> SEQ ID NO 136
<211> LENGTH: 20
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 136
catgccagtg aaacggtcct                                              20

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
catgccagtg aaaacggtcc t                                            21

<210> SEQ ID NO 138
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
catgccagtg ataaacggtc ct                                           22

<210> SEQ ID NO 139
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
catgccagtg attaaacggt cct                                          23

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
catgccagtg atgaaacggt cct                                          23

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
catgccagtg taaacggtcc t                                            21

<210> SEQ ID NO 142
<211> LENGTH: 138
<212> TYPE: DNA
<213> ORGANISM: Unknown

```
<220> FEATURE:
<223> OTHER INFORMATION: Description of Unknown:
      BCL6 sequence
<220> FEATURE:
<221> NAME/KEY: modified_base
<222> LOCATION: (31)..(108)
<223> OTHER INFORMATION: a, c, t, g, unknown or other

<400> SEQUENCE: 142
acccgccatg ccagtgatgt tcttctcaac nnnnnnnnnn nnnnnnnnnn nnnnnnnnnn    60
nnnnnnnnnn nnnnnnnnnn nnnnnnnnnn nnnnnnnnnn nnnnnnnac ggtcctcatg    120 gcctgcaggt gagggatc                                                 138

<210> SEQ ID NO 143
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (31)..(108)
<223> OTHER INFORMATION: a, c, t, g, unknown or other

<400> SEQUENCE: 143
acccgccatg ccagtgatgt tcttctcaac nnnnnnnnnn nnnnnnnnnn nnnnnnnnnn    60
nnnnnnnnnn nnnnnnnnnn nnnnnnnnnn nnnnnnnnnn nnnnnnnac ggtcctcatg    120 gcctgcagtg agggatc                                                  137

<210> SEQ ID NO 144
<211> LENGTH: 132
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (30)..(107)
<223> OTHER INFORMATION: a, c, t, g, unknown or other

<400> SEQUENCE: 144
acccgccatg cagtgatgtt cttctcaacn nnnnnnnnn nnnnnnnnnn nnnnnnnnnn    60
nnnnnnnnnn nnnnnnnnnn nnnnnnnnnn nnnnnnnnnn nnnnnnacg gtcctcatgg    120 cctgcaggga tc                                                       132

<210> SEQ ID NO 145
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (30)..(107)
<223> OTHER INFORMATION: a, c, t, g, unknown or other

<400> SEQUENCE: 145
acccgccatg cagtgatgtt cttctcaacn nnnnnnnnn nnnnnnnnnn nnnnnnnnnn    60
nnnnnnnnnn nnnnnnnnnn nnnnnnnnnn nnnnnnnnnn nnnnnnacg gtcctcatgg    120 cctgcgtgag ggatc                                                    135
```

<210> SEQ ID NO 146
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (30)..(107)
<223> OTHER INFORMATION: a, c, t, g, unknown or other

<400> SEQUENCE: 146
acccgccatg cagtgatgtt cttctcaacn nnnnnnnnn nnnnnnnnnn nnnnnnnnnn        60
nnnnnnnnnn nnnnnnnnnn nnnnnnnnnn nnnnnnnnnn nnnnnnacg gtcctcatgg       120 cctgtgaggg atc                                                         133

<210> SEQ ID NO 147
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (17)..(94)
<223> OTHER INFORMATION: a, c, t, g, unknown or other

<400> SEQUENCE: 147
acccgccatg ctcaacnnnn nnnnnnnnnn nnnnnnnnnn nnnnnnnnnn nnnnnnnnnn        60
nnnnnnnnnn nnnnnnnnnn nnnnnnnnnn nnnnacggtc tcatggcct gcagtgaggg       120 atc                                                                    123

<210> SEQ ID NO 148
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (4)..(81)
<223> OTHER INFORMATION: a, c, t, g, unknown or other

<400> SEQUENCE: 148
aacnnnnnnn nnnnnnnnnn nnnnnnnnnn nnnnnnnnnn nnnnnnnnnn nnnnnnnnnn        60
nnnnnnnnnn nnnnnnnnnn nacggtcctc atggtgaggg atc                        103

<210> SEQ ID NO 149
<211> LENGTH: 115
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (30)..(107)
<223> OTHER INFORMATION: a, c, t, g, unknown or other

<400> SEQUENCE: 149
acccgccatg cagtgatgtt cttctcaacn nnnnnnnnn nnnnnnnnnn nnnnnnnnnn        60
nnnnnnnnnn nnnnnnnnnn nnnnnnnnnn nnnnnnnnnn nnnnnnnacg ggatc           115

<210> SEQ ID NO 150
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (26)..(103)
<223> OTHER INFORMATION: a, c, t, g, unknown or other

<400> SEQUENCE: 150
acccgccatg catgttcttc tcaacnnnnn nnnnnnnnnn nnnnnnnnnn nnnnnnnnnn    60
nnnnnnnnnn nnnnnnnnnn nnnnnnnnnn nnnnnnnnnn nnnacggtcc tcatggcctg   120
cagtcgatag gtg                                                      133

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
acccgccatg cgtgagggat c                                              21

<210> SEQ ID NO 152
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
acccgccatg cggtgaggga tc                                             22

<210> SEQ ID NO 153
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
acccgccatg ccaggtgagg gatc                                           24

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
acccgccatg caggtgaggg atc                                            23

<210> SEQ ID NO 155
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
acccgccatg ccggtgaggg atc                                              23

<210> SEQ ID NO 156
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
gtatttcgat tcttggctt tatatatctt gtggaaagga cgaaacaccg gccatagctt       60
aattaatcgt tttagagcta gaaatagcaa gttaaaa                               97

<210> SEQ ID NO 157
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gtatttcgat tcttggctt tatatatctt gtggaaagga cgaaacaccg cctacatgta       60
ggtatgggag ttttagagct agaaatagca agttaaaa                              98

<210> SEQ ID NO 158
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
gtatttcgat tcttggctt tatatatctt gtggaaagga cgaaacaccg gccatagctt       60
aattaatcgt tttagagcta gaaatagcaa gttaaaa                               97

<210> SEQ ID NO 159
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
gtatttcgat tcttggctt tatatatctt gtggaaagga cgaaacaccg cgtgaccagt       60
catttgcggt tttagagcta gaaatagcaa gttaaaa                               97

<210> SEQ ID NO 160
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160

```
gtatttcgat tcttggctt tatatatctt gtggaaagga cgaaacaccg ccctccagct    60
tgactaaagt tttagagcta gaaatagcaa gttaaaa                            97
```

<210> SEQ ID NO 161
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161

```
gtatttcgat tcttggctt tatatatctt gtggaaagga cgaaacaccg atgagagttt    60
aggccgctgt tttagagcta gaaatagcaa gttaaaa                            97
```

<210> SEQ ID NO 162
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162

```
gtatttcgat tcttggctt tatatatctt gtggaaagga cgaaacaccg caactcccat    60
attgaggttg ttttagagct agaaatagca agttaaaa                           98
```

<210> SEQ ID NO 163
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163

```
gtatttcgat tcttggctt tatatatctt gtggaaagga cgaaacaccg ttgtttctta    60
ctcttagatg ttttagagct agaaatagca agttaaaa                           98
```

<210> SEQ ID NO 164
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164

```
gtatttcgat tcttggctt tatatatctt gtggaaagga cgaaacaccg tctcaagctt    60
cttggcgcgg ttttagagct agaaatagca agttaaaa                           98
```

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165

```
gttttagagc tagaaatagc                                               20
```

<210> SEQ ID NO 166

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
cacctttcct gctttgtggc                                                   20

<210> SEQ ID NO 167
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
gaaacaccgc aagatggatg atcgtccagg ttttagagc                              39
```

GENE MODIFICATION ASSAYS

RELATED APPLICATIONS

This application claims the benefit under 35 U.S.C. § 119(e) of U.S. provisional application No. 62/279,337, filed Jan. 15, 2016, which is incorporated by reference herein in its entirety.

REFERENCE TO AN ELECTRONIC SEQUENCE LISTING

The instant application contains a Sequence Listing which has been filed electronically in ASCII format and is hereby incorporated by reference in its entirety. Said ASCII copy, created on Oct. 23, 2018, is named 0098-0025US1_SL.txt and is 48,435 bytes in size.

BACKGROUND

The clustered, regularly interspaced, short palindromic repeats (CRISPR)-associated protein 9 (Cas9) system is a technology used for precise genome editing in mammalian cells. A growing number of studies successfully utilized CRISPR technology for performing genetic screens in either pooled or arrayed formats, most commonly through lentiviral delivery of guide RNA libraries. The key advantages of viral-based delivery of Cas9 and guide RNA libraries are the high efficiency of transduction in a broad range of cell types, being detectable downstream of pooled phenotypic screens by next-generation sequencing and possibility to enrich transduced cells using antibiotic selection markers.

SUMMARY

Provided herein, in some embodiments, are nucleic acid-based tools that may be used for high-throughput functional genomics studies as well as for the generation of knockout (gene inactivation or deletion) or knockin (gene activation or insertion) cell lines. Tools of the present disclosure include an "activatable reporter cassette," a guide RNA construct and a nuclease that can be used together, for example, to modify and isolate targeted cells of interest. As discussed in more detail below, an activatable reporter cassette includes a nuclease recognition site (NRS) flanked by two selection marker genes. The first selection marker gene is typically promoterless (not operably linked to a promoter) and may be used for selection of modified cells (e.g., knockin or knockout cells) with minimal risk of random integrations, and the second selection marker gene, which is downstream from the NRS and configured out-of-frame, may be used for enrichment of targeted cells during screening, for example. Transcription of the first (upstream) selectable marker gene is activated upon integration of the activatable reporter cassette into an intron of an endogenous expressed gene of interest. The first selectable marker is transcribed from the endogenous promoter of that gene. Transcription of the second (downstream) selectable marker gene is regulated by nuclease cleavage of the nuclease recognition site located between the two selection marker genes. Cleavage of this site results in a reconfiguration of the second selectable marker from out-of-frame to in-frame, permitting its transcription from the endogenous promoter located upstream.

Thus, expression of the first (upstream) selectable marker gene indicates integration of the activatable reporter cassette into an endogenous expressed gene of interest, and expression of the second (downstream) selectable marker gene indicates cleavage of the nuclease recognition site.

Typically, a cell for use in a gene modification assay, for example, contains (e.g., is co-transfected with) an activatable reporter cassette and a guide RNA (gRNA) construct. A gRNA construct encodes at least two different gRNAs: one gRNA targeting (complementary to) the nuclease recognition site of the activatable reporter construct, and at least one gRNA targeting a site in a gene of interest that is specific to that gene of interest. A nuclease that cleaves the nuclease recognition site(s) is also used in the methods provided herein. In some embodiments, the activatable reporter cassette includes a nucleic acid encoding a nuclease that cleaves the nuclease recognition site(s). In other embodiments, the gRNA construct includes a nucleic acid encoding the nuclease. In yet other embodiments, a nucleic acid encoding the nuclease may be introduced into a cell on a separate (independently replicating) vector. In still other embodiments, a nuclease that cleaves the nuclease recognition site(s) may be introduced (e.g., as purified protein) directly into, or may be expressed by, the cell that expresses an activatable reporter cassette and a gRNA construct.

FIG. 1A shows an example of how the various tools of the present disclosure may be implemented to identify (e.g., to screen for) an inactivated target gene of interest. As shown in the embodiment represented in FIG. 1A, an activatable reporter cassette is inserted into the AAVS1 locus of a cell and its expression is driven by an endogenous promoter located at the AAVS1 locus. The cassette contains a nuclease recognition site (NRS1) flanked by an upstream selectable marker gene that encodes puromycin N-acetyl-transferase (which confers resistance to puromycin) and a downstream, out-of-frame selectable marker gene that encodes blasticidin S deaminase (which confers resistance to blasticidin S). The endogenous gene of interest (Gene X) also contains a nuclease recognition site (NRS2), although the sequence of NRS2 differs from the sequence of NRS1. A nuclease (e.g., Cas9 or Cpf1) associated with a gRNA that targets NRS1 and a nuclease associated with a gRNA that targets NRS2 are also depicted. Each gRNA guides the nuclease to the respective nuclease recognition sites.

In the absence of a nuclease that recognizes and cleaves the nuclease recognition sites, the downstream (out-of-frame) selectable marker gene of the activatable reporter cassette is not expressed and the full-length gene of interest is expressed. In the presence of a nuclease that recognizes and cleaves the nuclease recognition sites, upon cleavage of the sites, the downstream selectable marker gene is reconfigured so that it is in-frame and is expressed, and the gene of interest is no longer expressed. Expression of the downstream selectable marker gene, which is only expressed upon cleavage of the activatable reporter cassette (at NRS1), serves as an indicator that the gene of interest was also cleaved and presumably inactivated (at NRS2).

The constructs and methods of the present disclosure may be used, for example, to facilitate screening of guide RNA libraries in arrayed or pooled format, or to facilitate cloning and expressing of single and guide RNAs, permitting the preparation of cost-efficient plasmid-based guide RNA (gRNA) libraries. Further, in some embodiments, the constructs and methods of the present disclosure may be used to enhance negative selection screens and synthetic lethality screens.

Thus, some embodiments of the present disclosure provide engineered nucleic acid constructs comprising a deoxyribonucleic acid-binding domain recognition site (DNA-BDRS) and an activatable reporter cassette that comprises a nuclease recognition site flanked by an upstream selectable marker gene and a downstream out-of-frame selectable marker gene that is different from the upstream selectable marker gene. In some embodiments, the upstream selectable marker gene is promoterless. In some embodiments, the upstream selectable marker gene is operably linked to a promoter.

Some embodiments of the present disclosure provide cells comprising (a) a target gene of interest that comprises at least one nuclease recognition site (NRS) specific to the gene of interest, (b) an engineered nucleic acid construct comprising a DNA-BDRS and an activatable reporter cassette that comprises a NRS flanked by an upstream selectable marker gene and a downstream out-of-frame selectable marker gene that is different from the upstream selectable marker gene, and (c) a programmable nuclease that binds to the DNA-BDRS. In some embodiments, cells further comprise a guide RNA (gRNA) complementary to the nuclease recognition site of the activatable reporter cassette and a gRNA complementary to the nuclease recognition site of the target gene of interest. In some embodiments, cells further comprise a nuclease that cleaves the NRS of the activatable reporter cassette and cleaves the NRS of the gene of interest.

Also provided herein are populations of cells of the present disclosure as well as cultures comprising cell media and population of cells.

Some embodiments of the present disclosure provide cells expressing (a) a target gene of interest that comprises a nuclease recognition site specific to the target gene of interest, (b) an activatable reporter cassette comprising a nuclease recognition site flanked by an upstream selectable marker gene and a downstream out-of-frame selectable marker gene that is different from the upstream selectable marker gene, (c) a nuclease that cleaves the nuclease recognition site of the activatable reporter cassette and cleaves the nuclease recognition site of the target gene of interest, and (d) a guide RNA (gRNA) complementary to the nuclease recognition site of the activatable reporter cassette and a gRNA complementary to the nuclease recognition site of the target gene of interest.

The present disclosure also provides methods of producing cells for a gene modification assay, comprising transfecting cells that express (a) a target gene of interest that comprises a nuclease recognition site specific to the target gene of interest, (b) an activatable reporter cassette that comprises a nuclease recognition site flanked by an upstream selectable marker gene and a downstream out-of-frame selectable marker gene that is different from the upstream selectable marker gene, and (c) a nuclease that cleaves the nuclease recognition site of (a) and (b), with at least one engineered nucleic acid that encodes a guide RNA (gRNA) complementary to the nuclease recognition site of (a) and a gRNA complementary to the nuclease recognition site of (b), thereby producing cells for a gene modification assay.

Some embodiments provide methods of producing cells for a gene modification assay, comprising: (a) transfecting a first population of cells that express (i) a first target gene of interest that comprises a nuclease recognition site specific to the first target gene of interest, (ii) an activatable reporter cassette that comprises a nuclease recognition site flanked by an upstream selectable marker gene and a downstream out-of-frame selectable marker gene that is different from the upstream selectable marker gene, and (iii) a nuclease that cleaves the nuclease recognition site of (a)(i) and the nuclease recognition site of (a)(ii) with at least one engineered nucleic acid that encodes a guide RNA (gRNA) complementary to the nuclease recognition site of (a)(i) and a gRNA complementary to the nuclease recognition site of (a)(ii); and (b) transfecting a second population of cells that express (i) a second target gene of interest that comprises a nuclease recognition site, (ii) an activatable reporter cassette that comprises a nuclease recognition site flanked by an upstream selectable marker gene and a downstream out-of-frame selectable marker gene that is different from the upstream selectable marker gene, and (iii) a nuclease that cleaves the nuclease recognition site of (b)(i) and the nuclease recognition site of (b)(ii) with at least one engineered nucleic acid that encodes a guide RNA (gRNA) complementary to the nuclease recognition site of (b)(i) and a gRNA complementary to the nuclease recognition site of (b)(ii), thereby producing cells for a gene modification assay.

Some embodiments provide methods of producing cells for a gene modification assay, comprising: introducing into cells that express (a) a target gene of interest that comprises a nuclease recognition site specific to the target gene of interest, (b) an activatable reporter cassette that comprises a nuclease recognition site flanked by an upstream selectable marker gene and a downstream out-of-frame selectable marker gene that is different from the upstream selectable marker gene, and (c) a nuclease that cleaves the nuclease recognition site of (a) and (b), at least one engineered guide RNA (gRNA) complementary to the nuclease recognition site of (a) and a gRNA complementary to the nuclease recognition site of (b), thereby producing cells for a gene modification assay.

Also provided herein are methods of producing cells for a gene modification assay, comprising: transfecting cells that express (a) a target gene of interest that comprises a nuclease recognition site specific to the target gene of interest and (b) an activatable reporter cassette that comprises a nuclease recognition site flanked by an upstream selectable marker gene and a downstream out-of-frame selectable marker gene that is different from the upstream selectable marker gene, with at least one engineered nucleic acid that encodes a guide RNA (gRNA) complementary to the nuclease recognition site of (a) and a gRNA complementary to the nuclease recognition site of (b), thereby producing cells for a gene modification assay.

The present disclosure further provides methods of producing cells for a gene modification assay, comprising: transfecting cells that express (a) a target gene of interest that comprises a nuclease recognition site specific to the target gene of interest and (b) a nuclease that cleaves the nuclease recognition site of the target gene of interest and cleaves a nuclease recognition site of an activatable reporter cassette, with an engineered nucleic acid construct comprising a deoxyribonucleic acid-binding domain recognition site (DNA-BDRS) and an activatable reporter cassette that comprises a nuclease recognition site flanked by an upstream selectable marker gene and a downstream an out-of-frame selectable marker gene that is different from the upstream selectable marker gene.

Further provided herein are methods of producing cells for a gene modification assay, comprising: transfecting cells that express a target gene of interest that comprises a nuclease recognition site specific to the target gene of interest with an engineered nucleic acid construct comprising a deoxyribonucleic acid-binding domain recognition site (DNA-BDRS) and an activatable reporter cassette that comprises a nuclease recognition site flanked by an upstream selectable marker gene and a downstream an out-of-frame selectable marker gene that is different from the upstream selectable marker gene.

BRIEF DESCRIPTION OF THE DRAWINGS

FIG. 5B shows sequencing results for DNA extracted from cells expressing: an activatable reporter cassette containing an out-of-frame BSD gene and a plasmid encoding Cas9, a gRNA targeting a NRS of the activatable reporter cassette, and a gRNA (gRNA-Cr1) targeting a NRS (Cr1) of the MAP3K1 gene (SEQ ID NOs: 1-6, left panel, top to bottom; SEQ ID NOs: 1 and 7-24, right panel, top to bottom). In the absence of BSD, 16% of the sequenced alleles were mutated. In the presence of BSD, the frequency of mutated alleles increased to 67%.

FIG. 6A shows a schematic depicting the location of two nuclease recognition target sites (Cr1 and Cr2) and primers used for amplifying the surrounding regions. FIG. 6B shows sequencing results for DNA extracted from cells expressing: an activatable reporter cassette containing an out-of-frame BSD gene and a plasmid encoding Cas9, a gRNA targeting a NRS of the activatable reporter cassette, and a gRNA (gRNA-Cr2) targeting a NRS (Cr2) of the MAP3K1 gene (SEQ ID NOs: 25-27, left panel, top to bottom, SEQ ID NOs: 25, 28-43, right panel, top to bottom). In the absence of BSD, 10% of the sequenced alleles were mutated. In the presence of BSD, the frequency of mutated alleles increased to 93%.

FIG. 8A shows a schematic depicting the location of two nuclease recognition target sites (Cr1 and Cr2) and primers used for amplifying the surrounding regions. FIG. 8B shows sequencing results for DNA extracted from cells expressing: an activatable reporter cassette containing an out-of-frame BSD gene and a plasmid encoding Cas9, a gRNA targeting a NRS of the activatable reporter cassette, and a gRNA (gRNA-Cr1) targeting a NRS (Cr1) of the AAVS1 gene (SEQ ID NOs: 57-68, left panel, top to bottom, SEQ ID NOs: 57, 69-79, right panel, top to bottom). In the absence of BSD, 32% of the sequenced alleles were mutated. In the presence of BSD, the frequency of mutated alleles increased to 75%.

FIG. 9A shows a schematic depicting the location of two nuclease recognition target sites (Cr1 and Cr2) and primers used for amplifying the surrounding regions. FIG. 9B shows sequencing results for DNA extracted from cells expressing: an activatable reporter cassette containing an out-of-frame BSD gene and a plasmid encoding Cas9, a gRNA targeting a NRS of the activatable reporter cassette, and a gRNA (gRNA-Cr2) targeting a NRS (Cr2) of the AAVS1 gene (SEQ ID NOs: 80-84, left panel, top to bottom, SEQ ID NOs: 80, 85-89, right panel, top to bottom). In the absence of BSD, 10% of the sequenced alleles were mutated. In the presence of BSD, the frequency of mutated alleles increased to 53%.

FIG. 10A shows a schematic depicting the location of two nuclease recognition target sites (Cr1 and Cr2) and primers used for amplifying the surrounding regions. FIG. 10B shows sequencing results for DNA extracted from cells expressing: an activatable reporter cassette containing an out-of-frame BSD gene and a plasmid encoding Cas9, a gRNA targeting a NRS of the activatable reporter cassette, and a dual gRNA (gRNA-Cr1+Cr2) targeting two different nuclease recognition sites (Cr1 and Cr2) of the AAVS1 gene (SEQ ID NOs: 90-96, top to bottom). In the presence of BSD, the frequency of mutated alleles was 85%.

FIG. 11A shows a schematic depicting the location of three nuclease recognition target sites (Cr1, Cr2 and Cr3) and primers used for amplifying the surrounding regions. FIG. 11B shows sequencing results for DNA extracted from cells expressing: an activatable reporter cassette containing an out-of-frame BSD gene and a plasmid encoding Cas9, a gRNA targeting a NRS of the activatable reporter cassette, and a dual gRNA (gRNA-Cr1+Cr3) targeting two different nuclease recognition sites (Cr1 and Cr3) of the GFAP gene (SEQ ID NOs: 97-110, top to bottom). In the presence of BSD, the frequency of mutated alleles was 97%.

FIG. 12A shows a schematic depicting the location of three nuclease recognition target sites (Cr1, Cr2 and Cr3) and primers used for amplifying the surrounding regions. FIG. 12B shows sequencing results for DNA extracted from cells expressing: an activatable reporter cassette containing an out-of-frame BSD gene and a plasmid encoding Cas9, a gRNA targeting a NRS of the activatable reporter cassette, and a dual gRNA (gRNA-Cr2+Cr3) targeting two different nuclease recognition sites (Cr2 and Cr3) of the GFAP gene (SEQ ID NOs: 111-126, top to bottom). In the presence of BSD, the frequency of mutated alleles was 100%.

FIG. 14A shows a schematic depicting the location of four nuclease recognition target sites (Cr1, Cr2, Cr3 and Cr4) and primers used for amplifying the surrounding regions. FIG. 14B shows sequencing results for DNA extracted from cells expressing: an activatable reporter cassette containing an out-of-frame BSD gene and a plasmid encoding Cas9, a gRNA targeting a NRS of the activatable reporter cassette, and a dual gRNA (gRNA-Cr2+Cr4) targeting two different nuclease recognition sites (Cr2 and Cr4) of the BCL6 gene (SEQ ID NOs: 142-155, top to bottom). In the presence of BSD, the frequency of mutated alleles was 88%.

FIG. 18A shows that targeting the activatable reporter cassette using a single gRNA can result in frameshifts and only ⅓ of the targeted cells acquire resistance, for example. FIG. 18B shows CrNRS1 repeated twice and, depending on the fidelity of the repair mechanism, a higher percentage of the cells (more than ⅔) express BSD after CrNRS1 targeting, for example.

FIG. 19 shows an example of how an activatable reporter cassette can be used in a negative selection assay. Cells are transfected with nucleic acids encoding an activatable reporter cassette (puro-NRS1-BSD (out-of-frame)), Cas9, and a gRNA construct: a gRNA targeting NRS1 of the activatable reporter cassette and a gRNA targeting a recognition site (Cr1) in Alu (panels 1-3 (left to right)), 5.8S, or telomere. Targeting each of the foregoing sites was expected to result in cell lethality. In the presence of BSD, most or all of the cells died, which indicates that in transfected cells, the lethality genes were correctly targeted. However, in absence of selection with BSD, cells show 100% confluency—the small proportion of untransfected (WT) cells masked the readout.

FIG. 23C shows GFP-positive cells two weeks following BSD selection.

FIG. 25C shows schematics of two strategies for generating gRNAs using PCR for both Cas9 and Cpf1 is. In both strategies, the protospacer may be amplified using linkered primers.

FIG. 26A shows an overlap-extension design of oligonucleotides for a PCR method that can be used to amplify any cassette containing U6 promoter together with a gRNA backbone (SEQ ID NOS 165-166, respectively, in order of appearance). FIG. 26B shows that PCR-based gRNA products are efficient to induce gene knock out in HEK293 cells stably expressing Cas9.

FIG. 27A shows an example of how overlap-extension oligonucleotides can be used for ligation-free cloning of gRNAs. FIG. 27B shows that 9 out of 11 gRNAs are correctly assembled into the vector using PCR products generated by overlap extension (SEQ ID NO: 167).

FIG. 29A, bottom panel, shows results from NGS analyses on samples containing large indels induced by dual-gRNAs.

FIG. 31 shows confluency measurements using INCUCYTE® after transfection of gRNAs with and without REMindel. Lethality screening results for three lethal gRNAs (Alu cr1, Alu cr2 and Alu Cr3) targeting the Alu element and one non-lethal gRNA targeting AAVS1 locus in HEK293-REM cells are represented. Confluency was measured during two weeks on a daily basis. Three different transfection efficiencies with two different number of initial cells (30% and 50% confluency) with and without selection were compared. Without selection, the correct readout for Alu gRNAs (lethality) was masked because of non-transfected cells. However, REMindel successfully revealed the correct readout for lethal gRNAs.

DETAILED DESCRIPTION

Figure 1A:
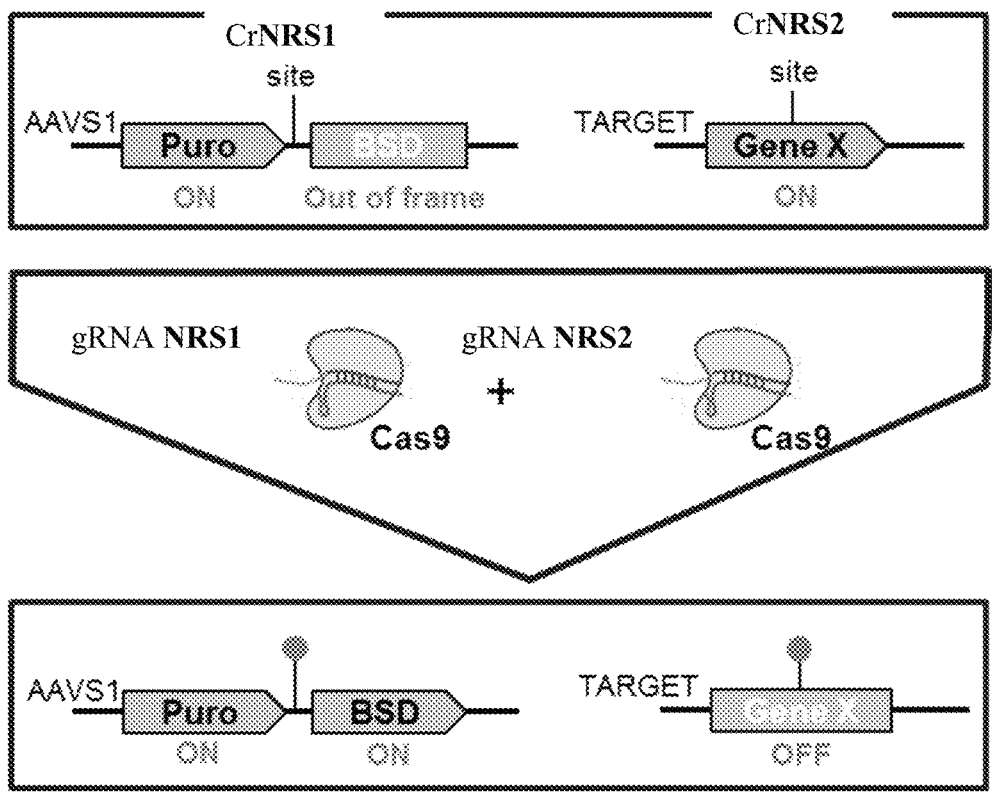
FIG. 1A shows a schematic of an example of an arrayed screening methodology of the present disclosure. An activatable reporter containing an artificial nuclease (recognition) cleavage site ("CrNRS1") and targeting the AAVS1 locus is transfected (e.g., stably transfected) into cells expressing Cas9 nuclease (or a similar nuclease) and a target gene of interest ("Gene X"), which contains a nuclease cleavage site specific to the gene of interest ("CrNRS2"). The activatable reporter contains a promoterless selectable marker gene ("Puro") and an out-of-frame selectable marker gene ("BSD"), which is only expressed following cleavage of the CrNRS1 site. A construct containing a CrNRS1 cleavage site flanked by a promoterless selectable marker gene and an out-of-frame selectable marker gene is referred to herein, in some instances, as a "REMindel cassette." Nucleic acids encoding guide RNAs (gRNAs) (e.g., single gRNA, dual gRNA, or multiple gRNAs) specific to CrNRS1 and CrNRS2 are then transfected into the cells of interest. Cells are then selected for activation of (expression of) BSD. A phenotypic analysis, for example, may be performed on cells expressing BSD.

The present disclosure provides, in some embodiments, nucleic acid-based tools that include an "activatable reporter cassette," a guide RNA construct and a RNA-guided nuclease that can be used together to modify and isolate targeted cells of interest. Advantageously, the methods provided herein, in some embodiments, are robust, cost-efficient and user-friendly. Further, the methods provided herein, in some embodiments, are virus-free.

Practical disadvantages that limit applications of lentivirus-based guide RNA libraries, particularly for arrayed screens, may be addressed using the constructs and methods of the present disclosure. Some of these limitations include costly and labor-expensive production, non-renewable stocks for end users, requirement of biosafety level 2 facilities and virus-compatible automation infrastructure. Moreover, due to the random integration of viral DNA, lentivirus-based systems can interfere with some phenotypic investigations. In addition, long-term exposure of a genome with Cas9 and guide RNA expression provided by lentiviruses can increase the chance of off-target events.

Similarly, practical disadvantages that limit the use of transfection-based systems (e.g., transfection of plasmids) for delivery of guide RNA libraries may be addressed using the constructs and methods of the present disclosure. In many cell types, nucleic acid transfection efficiency is low and the efficiency of protein transfection is even lower. For negative selection experiments, a potentially small proportion of untransfected cells will have growth advantages, thus masking the phenotypic readout. Moreover, plasmid-based screens, similar to virus-based screens, may delay phenotypic analysis. This is because plasmid-based arrayed screens are usually conducted in microwell plates, and the additional time required for transcription and translation of Cas9, for example, following plasmid transfection, results in over-confluency. This over-confluency renders the phenotypic readout difficult. Depending on the biology of the targeted genes, additional variability with respect to time must also be considered, commencing from when genetic mutagenesis occurs and ending at the time that cells acquire a corresponding phenotype(s).

The methods and nucleic acid constructs provided herein may be used to overcome many of the above-described disadvantages associated with lentiviral-based and transfection/plasmid-based systems.

Activatable Reporter Cassette

An "activatable reporter cassette" refers to a nucleic acid that comprises a nuclease recognition site (NRS) flanked by an upstream selectable marker gene and a downstream out-of-frame selectable marker gene that is different from (not the same as) the upstream selectable marker gene.

A "nuclease recognition site" is a nucleotide sequence that is cleaved by a cognate nuclease (enzyme that cleaves phosphodiester bonds between the nucleotide subunits of the nuclease recognition site). In some embodiments, the cognate nuclease is a RNA-guided nuclease, such as, for example, Cas9. As described elsewhere herein, a RNA-guided nuclease binds to a guide RNA (gRNA) that contains a scaffold sequence necessary for nuclease binding and a user-defined targeting sequence that defines (is complementary to) the target to be modified/cleaved. Thus, one can change the target of the nuclease by simply changing the targeting sequence present in the gRNA. A target gene of interest typically contains a nuclease recognition site (NRS) specific to the target gene of interest, which means the nucleotide sequence that defines the NRS of the target gene of interest is present only in the target gene of interest (is not present in other genes in the cell). It should be understood that while a NRS may be specific to a target gene of interest, the nuclease (e.g., Cas9 or Cpf1) that cleaves the NRS is capable of cleaving other nuclease recognition sites, each defined by its complementarity to a user-defined gRNA. The specificity of the nuclease is dependent on the targeting sequence of an associated gRNA. For example, an activatable reporter cassette and a target gene of interest each include a different NRS (different from each other). Even though the NRS of the target gene of interest is specific to the target gene of interest, the nuclease (e.g., Cas9) that cleaves the NRS of the target gene of interest may also cleave the NRS of the activatable reporter cassette.

A nuclease recognition site is considered "flanked" by selectable markers if there is a selectable marker gene located upstream from and adjacent to (e.g., within 1 to 100 nucleotides of) the nuclease recognition site and a selectable marker gene located downstream from and adjacent to the nuclease recognition site. Nuclease recognition sites are discussed below in more detail.

A "selectable marker" is a gene introduced into a cell that confers a trait suitable for artificial selection or encodes a protein that can be used for artificial selection. A selectable marker may be, for example, an antibiotic resistance gene. Non-limiting examples of antibiotic resistance genes include genes encoding resistance to puromycin, blasticidin S, ampicillin, kanamycin, geneticin, triclosan, chloroamphenicol, tetracycline, hygromycin or nourseothricin-dihydrogen sulfate (clonNAT). For example, the puromycin N-acetyl-transferase gene (pac) from *Streptomyces* confers puromycin resistance to host cells, the blasticidin S deaminase gene from *Aspergillus terreus* confers blasticidin S resistance to host cells, the beta-lactamase gene confers ampicillin resistance to host cells, the neo gene obtained from Tn5 confers resistance to kanamycin in bacterial cells and geneticin in eukaryotic cells, the mutant FabI gene (mFabI) obtained from the *Escherichia coli* genome confers triclosan resistance to host cells, the chloramphenicol acetyltransferase gene confers resistance to chloramphenicol, and more than 60 different genes can confer resistance to tetracycline. Hygromycin B phosphotransferase (Hph) confers hygromycin resistance to host cells.

Selectable marker genes are not limited to antibiotic resistance genes. Selectable marker genes also include genes encoding a reporter protein, such as, for example, a fluorescent reporter protein. Non-limiting examples of fluorescent reporter molecules include green fluorescent protein (e.g., AcGFP1, ZsGreen1), red fluorescent protein (e.g., DsRed-Express2, DsRed-Express, tdTomato, DsRed-Monomer, DsRed2, AsRed2, mStrawberry, mCherry), far-red fluorescent protein (e.g., HcRed1, mRaspberry, E2-Crimson, mPlum), yellow fluorescent protein (e.g., ZsYellow1, mBanana), cyan fluorescent protein (e.g., AmCyan1), orange fluorescent protein (e.g., mOrange, mOrange2) and variants thereof.

In some embodiments, a selectable marker gene encodes a protein that can be used for artificial selection. For example, an activatable reporter cassette may contain an out-of-frame selectable marker gene that encodes a protein (e.g., cell membrane receptor) otherwise not expressed by the cell into which the cassette is introduced. Upon targeted cleavage of the activatable reporter cassette by a nuclease, the out-of-frame selectable marker gene is reconfigured so that it is in-frame and is expressed. Thus, the encoded protein is expressed and can be used as a selection marker. In some embodiments, a cell comprises an activatable reporter cassette that contains a downstream, out-of-frame selectable marker gene encoding a cell membrane receptor otherwise not expressed in the cells. Upon targeted cleavage of the activatable reporter cassette by a nuclease, the out-of-frame selectable marker gene is reconfigured so that it is in-frame and the cell membrane receptor is expressed. An antibody drug (e.g., toxin) conjugate that specifically binds to the receptor, for example, may then be used to select for cells in which cleave of the activatable reporter cassette occurred. It should be understood that any cognate protein binding pairs (e.g., receptor-ligand) may be used as described above.

"Upstream" and "downstream" refer to the relative position of nucleic acid (e.g., DNA or RNA). Each strand of DNA or RNA has a 5' end and a 3' end, so named for the carbon position on the deoxyribose (or ribose) ring. By convention, upstream and downstream relate to the 5' to 3' direction in which RNA transcription takes place. Upstream is toward the 5' end of the RNA molecule and downstream is toward the 3' end. When considering double-stranded DNA, upstream is toward the 5' end of the coding strand for the gene of interest and downstream is toward the 3' end of the coding strand. Thus, an upstream selectable marker and a downstream selectable marker are defined relative to each other on a single nucleic acid. The upstream selectable marker is located toward the 5' end of the nucleic acid and the downstream selectable marker is located toward the 3' end of the nucleic acid.

In most embodiments, the upstream selectable marker of an activatable reporter cassette is different from the downstream selectable marker of the same activatable reporter cassette. For example, an upstream selectable marker may be an antibiotic resistance gene that confers resistance to puromycin, while the downstream selectable marker may be an antibiotic resistance gene that confers resistance to blasticidin S, ampicillin, kanamycin, geneticin, triclosan, chloroamphenicol or tetracycline. As another example, an upstream selectable marker may be an antibiotic resistance gene that confers resistance to blasticidin S, while the downstream selectable marker may be an antibiotic resistance gene that confers resistance to puromycin, ampicillin, kanamycin, geneticin, triclosan, chloroamphenicol or tetracycline.

Activatable reporter cassettes generally contain both an upstream, in-frame selectable marker gene and a downstream, out-of-frame selectable marker gene. The upstream, in-frame selectable marker gene is referred to simply as an "upstream selectable marker gene." Any gene not designated specifically as "out-of-frame" should be considered "in-frame." "In-frame" and "out-of-frame" refer to the reading frame of a nucleic acid. A reading frame is a way of dividing the sequence of nucleotides in a nucleic acid (DNA or RNA) into a set of consecutive, non-overlapping triplets. A triplet that equates to an amino acid or stop signal during translation is referred to as a codon. A selectable marker gene is considered in-frame if the reading frame is intact and translation can run to completion. A selectable marker gene is considered out-of-frame if the reading frame is not intact and translation cannot run to completion.

For example, in FIG. 1A, the selectable marker gene encoding puromycin N-acetyl-transferase ("Puro") of the activatable reporter cassette (top panel) is in-frame, while the selectable marker gene encoding blasticidin S deaminase ("BSD") is out-of-frame. In this configuration, puromycin N-acetyl-transferase is expressed but blasticidin S deaminase is not expressed. Following cleavage of the Cr REM site (e.g., by Cas9), the selectable marker gene encoding blasticidin S deaminase is shifted from out-of-frame to in-frame and can now be later translated, resulting in expression of blasticidin S deaminase.

In some embodiments, an activatable reporter cassette contains an upstream selectable marker gene that is "promoterless," meaning that the upstream selectable marker gene is not operably linked to a promoter. A promoter is considered to be "operably linked" when it is in a correct functional location and orientation relative to a sequence of nucleic acid that it regulates (e.g., to control ("drive") transcriptional initiation and/or expression of that sequence). An activatable reporter cassette is configured so that the promoterless selectable marker gene is expressed only when inserted (knocked in or ligated) in-frame with a promoter of the genome of a cell in which the activatable reporter cassette is introduced. In this way, an activatable reporter cassette containing a promoterless selectable marker gene functions much like a gene trap cassette. A gene trap cassette, when inserted into an intron of an expressed gene, is transcribed from the endogenous promoter of that gene in the form of a fusion transcript in which the exon(s) upstream of the insertion site is spliced in frame to the reporter/selectable marker gene. Because transcription is terminated prematurely at the inserted polyadenylation site, the processed fusion transcript encodes a truncated and non-functional version of the cellular protein and the reporter/selectable marker.

Nuclease Recognition Site and Cognate Nucleases

Activatable reporter cassettes contain a (at least one) nuclease recognition site located between two selectable marker genes. As discussed above, a nuclease recognition site is a nucleotide sequence that is recognized and cleaved by a cognate nuclease (enzyme that cleaves (cuts/hydrolyzes) phosphodiester bonds between the nucleotide subunits of the nuclease recognition site).

Genes of interest that are endogenous to a cell, or that are introduced into the genome of cell, also contain a nuclease recognition site.

In some embodiments, a nuclease recognition site contains a sequence of nucleotides that is complementary (e.g., perfectly complementary) to a guide RNA and can be cleaved by an RNA-guided nuclease, such as Cas9 or Cpf1, for example. A nuclease recognition site typically comprises a protospacer adjacent motif (PAM) immediately following the targeted sequence. In some embodiments, the PAM is 5' NGG 3', e.g., for *Streptococcus pyogenes* Cas9.

The length and composition (e.g., percent A, T, C, G) of a nuclease recognition site may vary. For example, a nuclease recognition site may have a length of 10 to 50 nucleotides. In some embodiments, a nuclease recognition site has a length of 10 to 15, 10 to 20, 10 to 30, 10 to 40, 10 to 50, 15 to 20, 15 to 30, 15 to 40, 15 to 50, 20 to 30, 20 to 40, or 20 to 50 nucleotides. In some embodiments, a nuclease recognition site has a length of 10, 11, 12, 13, 14, 15, 16, 17, 18, 19, 20, 21, 22, 23, 24, 25, 26, 27, 28, 29 or 30 nucleotides.

Nuclease recognition sites, in some embodiments, are recognized and cleaved by programmable nucleases, including zinc finger nucleases (ZFNs) (Kim et al. *Proc Natl Acad Sci USA* 93 (3): 1156-60, 1996; Bitinaite et al. *Proc Natl Acad Sci USA* 95 (18): 10570-5, 1998; and Cathomen et al. *Mol. Ther.* 16 (7): 1200-7, 2008), TAL effector nucleases (TALENs, transcription activator-like effector nucleases) (Boch et al. *Science* 326 (5959): 1509-12, 2009; Christian et al. Genetics 186 (2): 757-61, 2010); and Miller et al. *Nature Biotechnology* 29 (2): 143-8, 2011), RNA-guided engineered nucleases (RGENs) derived from the bacterial clustered regularly interspaced short palindromic repeat (CRISPR)-Cas (CRISPR-associated) system, and functional equivalents thereof (Kim H. et al., *Nature Reviews Genetics* 15, 321-334 (2014)). Programmable nucleases typically comprise a DNA binding domain, which recognizes and binds to a pre-determined DNA sequence, and a DNA cleavage domain, which cleaves the DNA at or near (e.g., within 10 nucleotides of) the DNA binding domain. For example, ZFNs comprise zinc finger domains, which bind DNA, and a Fok I domain, which cleaves the DNA (Kim et al. *Natl Acad Sci USA* 93 (3): 1156-60, 1996). Similarly, TALENs comprise TAL effector units, which bind DNA, and a Fok I domain, which cleaves DNA. The RNA-guided Cas9 nuclease cleaves the DNA, but to do so, it must first be guided to the target cleavage site by a guide RNA, which is complementary to and binds to the DNA cleavage site.

In some embodiments, a nuclease is an RNA-guided nuclease, such as Cas9 or Cpf1.

Cas9 (CRISPR associated protein 9) is an RNA-guided nuclease of a class 2 CRISPR (Clustered Regularly Interspersed Palindromic Repeats) adaptive immunity system in *Streptococcus pyogenes*, among other bacteria. CRISPR systems for editing, regulating and targeting genomes may comprise at least two distinct components: (1) a guide RNA (gRNA) and (2) Cas9. A gRNA is a single chimeric transcript that combines the targeting specificity of endogenous bacterial CRISPR targeting RNA (crRNA) with the scaffolding properties of trans-activating crRNA (tracrRNA). Typically, a gRNA used for genome editing is transcribed from either a plasmid or a genomic locus within a cell. The gRNA transcript forms a complex with Cas9, and then the gRNA/Cas9 complex is recruited to a target sequence as a result of the base-pairing between the crRNA sequence and its complementary target sequence in genomic DNA, for example.

In a typical synthetic CRISPR/Cas9 genome editing system, a genomic sequence of interest (genomic target sequence) is modified by use of a gRNA complementary to the sequence of interest, which directs the gRNA/Cas9 complex to the target (Sander J D et al., 2014 *Nature Biotechnology* 32, 247-355, incorporated by reference herein). The Cas9 endonuclease cuts the genomic target DNA upstream of a protospacer adjacent motif (PAM), resulting in double-strand breaks. Repair of the double-strand breaks often results in inserts or deletions at the double-strand break site.

Cpf1 is also a RNA-guided nuclease of a class 2 CRISPR-Cas system (Zetsche et al., 2015, *Cell* 163: 1-13, incorporated by reference herein). Cpf1, like Cas9, is a two-component RNA programmable DNA nuclease. Targeted DNA is cleaved as a 5-nt staggered cut distal to a 5' T-rich protospacer adjacent motif (PAM). There are two Cpf1 orthologs that exhibit robust nuclease activity in human cells, either of which may be used as provided herein. Enzymes that are functionally similar to Cpf1 may be used in accordance with the present disclosure.

Guide RNA Constructs and RNA-Guided Nucleases

Gene modification methods of the present disclosure use guide RNAs to direct a RNA-guided nuclease to a nuclease recognition site of an activatable reporter cassette or a gene of interest. A "guide" RNA (gRNA) is one of two components of the clustered regularly interspaced short palindromic repeats (CRISPR) Type II system, which is a bacterial immune system that has been modified for genome engineering. The other component is a non-specific CRISPR-associated endonuclease (Cas9). A gRNA is a short synthetic RNA composed of a scaffold sequence necessary for Cas9-binding and a user-defined ~20 (e.g., 20±5 or 20±10) nucleotide "spacer" or "targeting" sequence which defines the genomic target to be modified. Thus, one can change the (genomic) target of Cas9 by simply changing the targeting sequence present in the gRNA. In some embodiments, a gRNA has a length of 10 to 100 nucleotides. For example, a gRNA may have a length of 10-90, 10-80, 10-70, 10-60, 10-50, 10-40, 10-35, 10-30, 10-25, 10-20, 10-15, 15-100, 15-90, 15-80, 15-70, 15-60, 15-50, 15-40, 15-35, 15-30, 15-25, 15-20, 20-100, 20-90, 20-80, 20-70, 20-60, 20-50, 20-40, 20-35, 20-30 or 20-25 nucleotides. In some embodiments, a gRNA has a length of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides. Longer gRNAs are encompassed by the present disclosure.

Figure 1B:
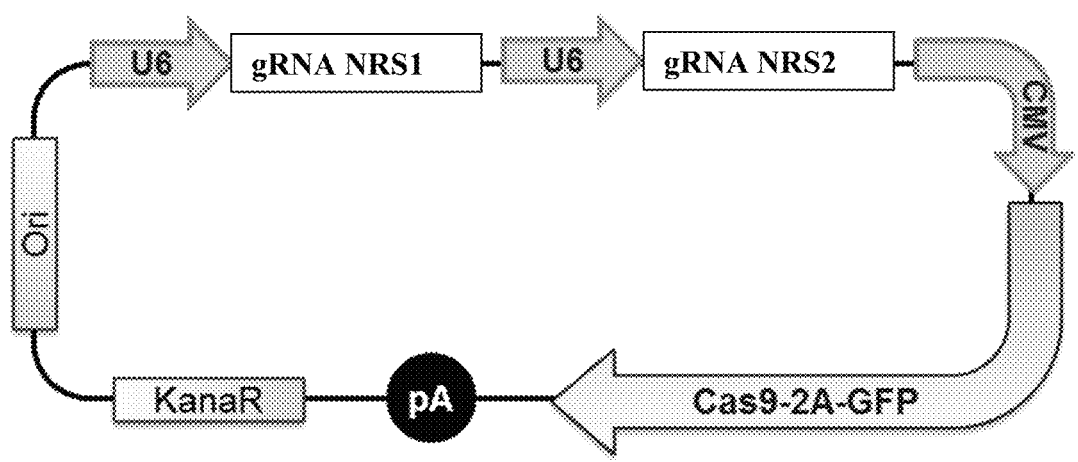
FIG. 1B shows a schematic of an example of a gRNA-NRS2-gRNA-NRS1-Cas9 construct.

FIG. 1B shows an example of a gRNA construct: a nucleic acid encoding a gRNA (gRNA NRS1) targeting a nuclease recognition site (NRS1) of an activatable reporter cassette is operably linked to a U6 promoter; and a nucleic acid encoding a gRNA (gRNA NRS2) targeting a nuclease recognition site (NRS2) of a gene of interest is operably linked to another U6 promoter. This particular example construct includes a nucleic acid encoding a RNA-guided nuclease, Cas9, which is operably linked to a CMV promoter. The construct further contains a polyA (pA) signal, a kanamycin resistance gene and an origin of replication (Ori).

Figures 7A, 7B:
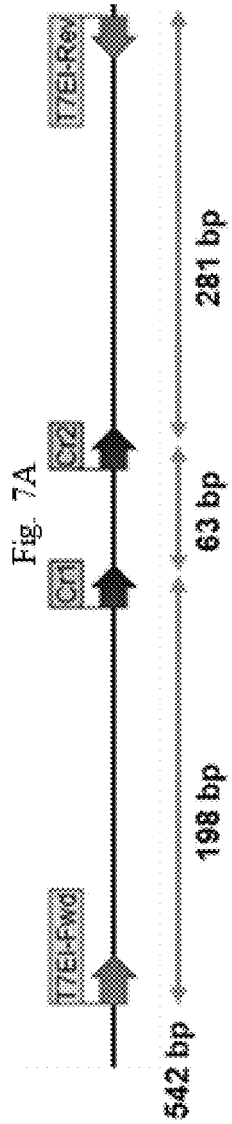
FIG. 7A shows a schematic depicting the location of two nuclease recognition target sites (Cr1 and Cr2) and primers used for amplifying the surrounding regions.
FIG. 7B shows sequencing results for DNA extracted from cells expressing: an activatable reporter cassette containing an out-of-frame BSD gene and a plasmid encoding Cas9, a gRNA targeting a NRS of the activatable reporter cassette, and a dual gRNA (gRNA-Cr1+Cr2) targeting two different nuclease recognition sites (Cr1 and Cr2) of the MAK3K1 gene (SEQ ID NOs: 44-47, top panel, top to bottom, SEQ ID NOs: 44, 48-56, bottom panel, top to bottom). In the absence of BSD, 30% of the sequenced alleles were mutated. In the presence of BSD, the frequency of mutated alleles increased to 92%.
Figures 13A, 13B:
FIG. 13A shows a schematic depicting the location of four nuclease recognition target sites (Cr1, Cr2, Cr3 and Cr4) and primers used for amplifying the surrounding regions.
FIG. 13B shows sequencing results for DNA extracted from cells expressing: an activatable reporter cassette containing an out-of-frame BSD gene and a plasmid encoding Cas9, a gRNA targeting a NRS of the activatable reporter cassette, and a dual gRNA (gRNA-Cr1+Cr3) targeting two different nuclease recognition sites (Cr1 and Cr3) of the BCL6 gene (SEQ ID NOs: 127-141, top to bottom). In the presence of BSD, the frequency of mutated alleles was 75%.
Figure 15:
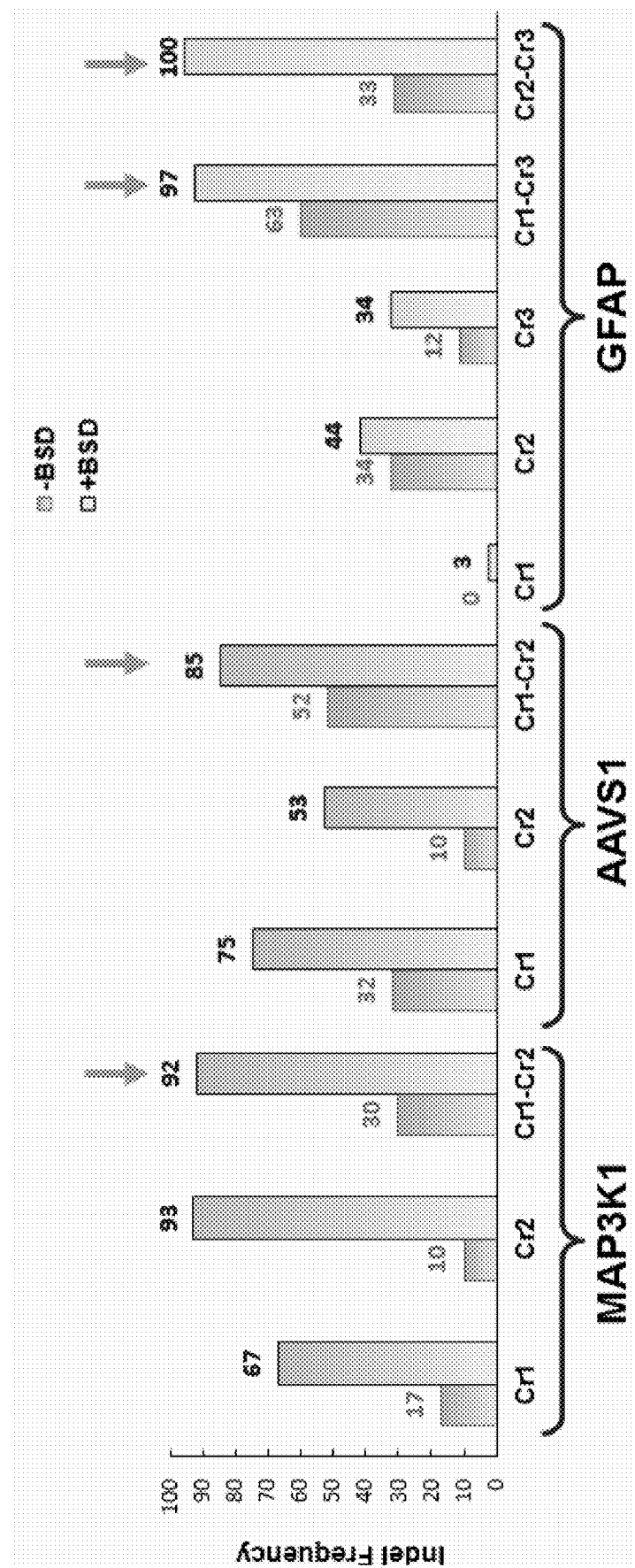
FIG. 15 compares the indel rate in the absence and presence of BSD expression.
Figure 16:
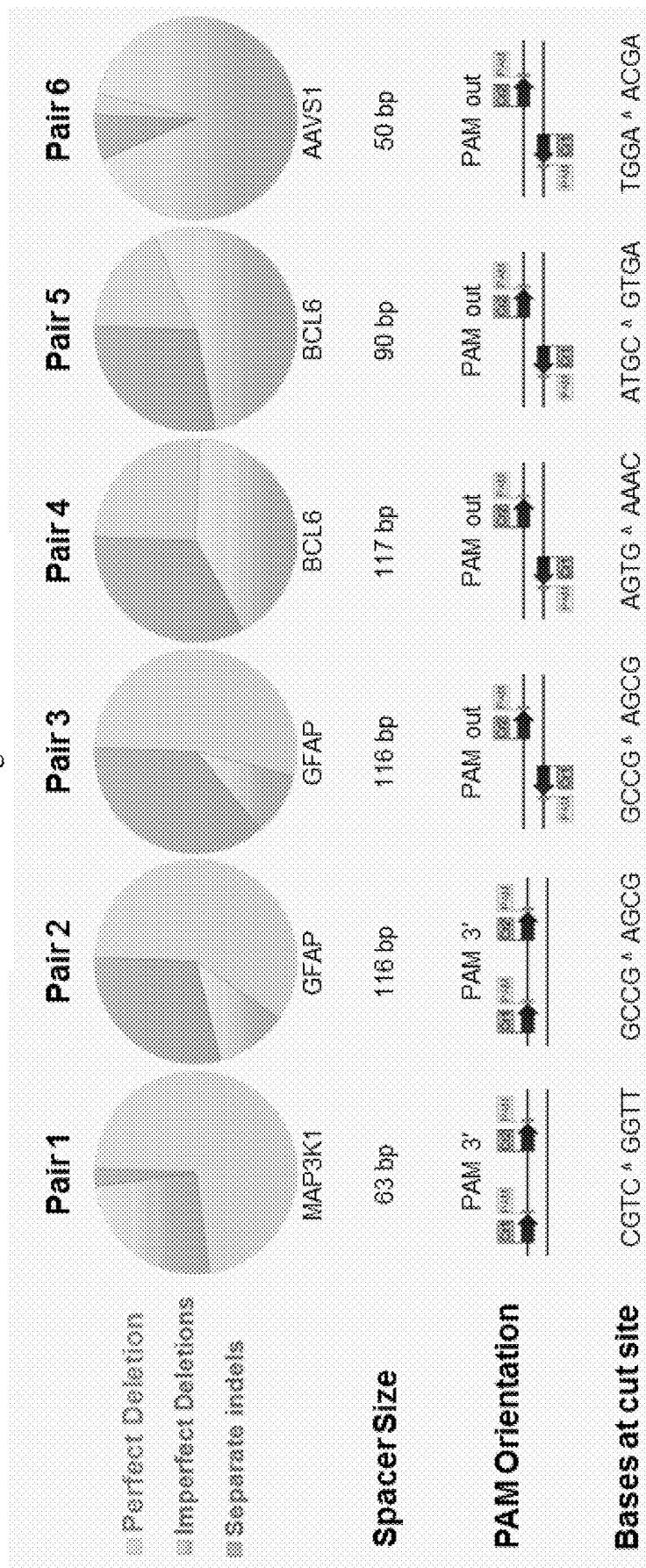
FIG. 16 shows schematics of data demonstrating that dual-gRNA does not always produce the same mutation pattern.
Figure 17A:
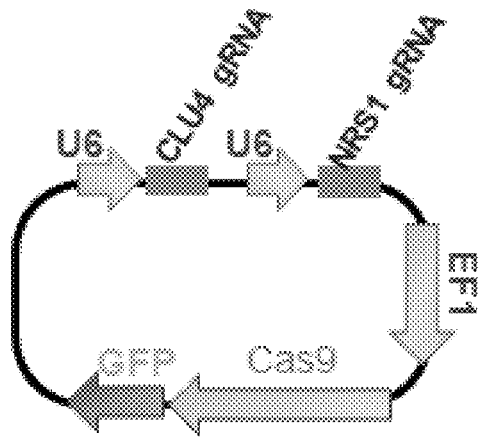
FIGS. 17A-17E show data demonstrating that enrichment of mutated cells using the activatable reporter cassette is effective regardless of transfection efficiency.
Figure 17B:
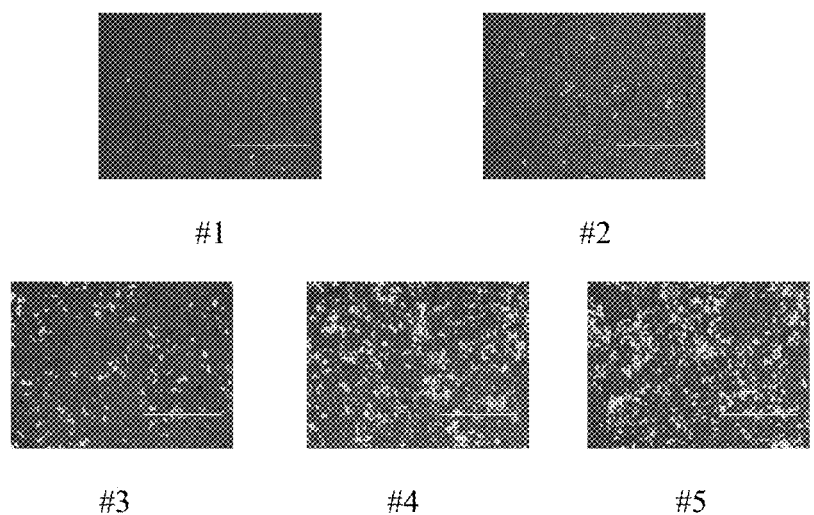
Figure 17C:
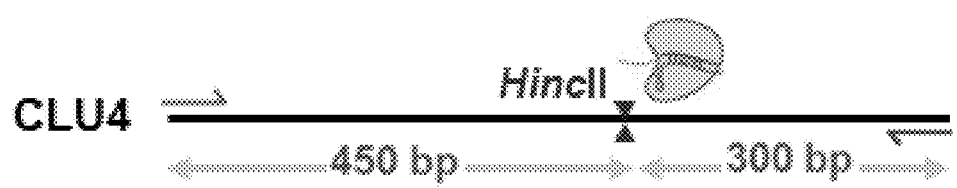
Figure 17D:
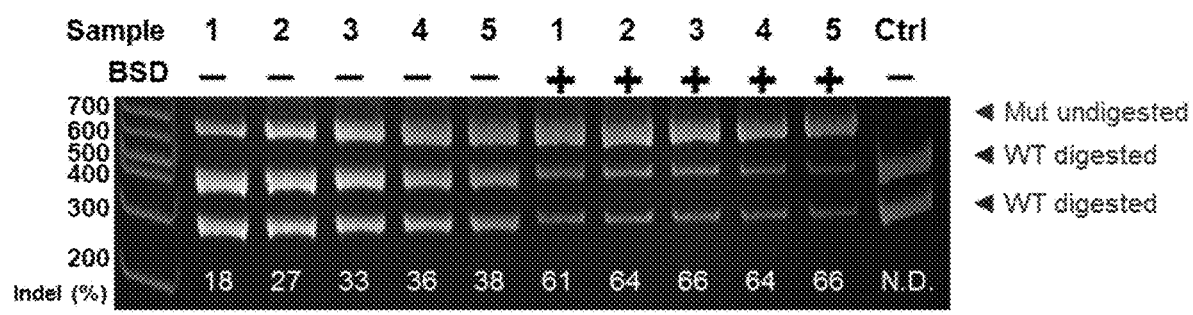
Figure 17E:
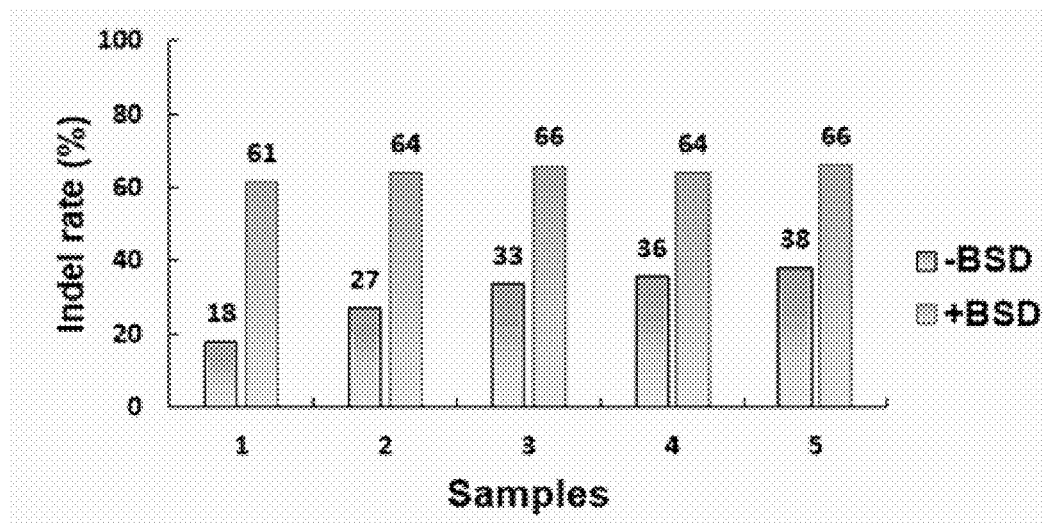

Constructs containing nucleic acids encoding a gRNA targeting a NRS1 of an activatable reporter cassette and two gRNAs, each of which targets a NRS specific to a gene of interest, are referred to herein as "dual gRNA constructs." For example, a dual gRNA construct may encode a gRNA that targets NRS1 of an activatable reporter cassette, a gRNA that targets Cr1 of a target gene of interest, and a gRNA that targets Cr2 of a target gene of interest (see, e.g., FIGS. 7B and 10B, showing data from experiments using a dual gRNA targeting Cr1 and Cr2 sites of the target gene of interest).

In some embodiments, nucleic acids encoding dual gRNAs (e.g., on the same vector or on separate vectors) are transfected into cells, while in other embodiments, two gRNAs (e.g., at equal molar amounts) are transfected into cells, for example, by electroporation or by a known chemical or physical transfection method.

An "RNA-guided nuclease" is a programmable endonuclease that can be used to perform targeted genome editing. The programmable nature of an RNA-guided nuclease, such as Cas9 or Cpf1, is a result of its association with a guide RNA (gRNA) that uses ~20 variable nucleotides at its 5' end to base pair with (are complementary to) a target DNA sequence cleaved by the nuclease. In some embodiments, the RNA-guided nuclease is Cas9. In some embodiments, the RNA-guided nuclease is Cpf1. Other RNA-guided nucleases are encompassed by the present disclosure.

Genomic Integration

Activatable reporter cassettes of the present disclosure are provided, in some embodiments, in the form of an engineered nucleic acid construct that contains a deoxyribonucleic acid-binding domain recognition site (DNA-BDRS). This DNA-BDRS is used to facilitate direct, site-specific ligation of a linearized form of the construct into a locus of a genome. Direct ligation occurs through the non-homologous end-joining (NHEJ) pathway (see, e.g., Maresca et al. *Genome Res.* 2013 March; 23(3):539-46, incorporated herein by reference). Site-specific integration depends, in part, on the presence of programmable nucleases that contain a DNA binding domain and a DNA cleavage domain (typically a FokI domain) and the presence of nucleic acids that contain at least one DNA-binding domain recognition sequence. A "DNA-binding domain recognition sequence" is a nucleotide sequence to which a nuclease DNA-binding domain of a programmable nuclease binds and a nuclease DNA cleavage domain of a programmable nuclease cleaves. Engineered constructs may contain at least one DNA-binding domain recognition sequence that is recognized and cleaved by a programmable nuclease. Cleavage of the engineered construct results in a linearized form, which can then be "ligated" into a genome in a site-specific manner.

In some embodiments, a DNA-binding domain recognition sequence of an engineered construct corresponds to a sequence located in the Rosa26 locus such that the nucleic acid may be integrated in a mouse genome. In some embodiments, a DNA-binding domain recognition sequence of an engineered construct corresponds to a sequence located in the AAVS1 locus such that the nucleic acid may be integrated in a human genome. Other DNA-binding domain recognition sequence located in other genomic loci are encompassed by the present disclosure.

Examples of programmable nuclease for use in linearizing an engineered construct include, without limitation, zinc finger nucleases (ZFNs), Tale nucleases (TALENs), and dCas9-FokI fusion proteins (catalytically inactive Cas9 fused to FokI), as described above.

In some embodiments, the DNA-binding domain recognition sequence is a ZFN DNA binding domain recognition sequence, which is bound by one or more zinc finger(s). The DNA-binding domain of individual ZFNs may contain between three and six individual zinc finger repeats and can each recognize between 9 and 18 base pairs. If the zinc finger domains are specific for their intended target site, then even a pair of 3-finger ZFNs that recognize a total of 18 base pairs can target a single locus in a mammalian genome.

In some embodiments, the DNA-binding domain recognition sequence is a TALEN DNA binding domain recognition sequence, which is bound by one or more TAL effector unit(s). TAL effectors are proteins secreted by *Xanthomonas* bacteria. The DNA binding domain typically contains a repeated highly conserved 33-34 amino acid sequence with the exception of the $12^{th}$ and $13^{th}$ amino acids. These two locations are highly variable (Repeat Variable Diresidue, RVD) and show a strong correlation with specific nucleotide recognition (Boch et al. *Science* 326 (5959): 1509-12, 2009; Moscou et al. *Science* 326 (5959): 1501, 2009, each of which is incorporated by reference herein). In some embodiments, specific DNA-binding domains are engineered by selecting a combination of repeat segments containing the appropriate RVDs (Boch et al. *Nature Biotechnology* 29 (2): 135-6, 2011).

In some embodiments, the DNA-binding domain recognition sequence is a sequence complementary (e.g., 100% complementary) to a (at least one) guide RNA (e.g., two co-expressed gRNAs). In some embodiments, the DNA-binding domain recognition sequence is a sequence that is at least 80%, at least 85%, at least 90%, at least 95% or at least 98% complementary to a gRNA (e.g., two co-expressed gRNAs). In such embodiments, a catalytically inactive Cas9 (dCas9) fused to FokI nuclease may be used to generate double strand breaks in an engineered nucleic acid.

Engineered Nucleic Acids

An "engineered nucleic acid" is a nucleic acid (e.g., at least two nucleotides covalently linked together, and in some instances, containing phosphodiester bonds, referred to as a phosphodiester "backbone") that does not occur in nature. Engineered nucleic acids include recombinant nucleic acids and synthetic nucleic acids. A "recombinant nucleic acid" is a molecule that is constructed by joining nucleic acids (e.g., isolated nucleic acids, synthetic nucleic acids or a combination thereof) and, in some embodiments, can replicate in a living cell. A "synthetic nucleic acid" is a molecule that is amplified or chemically, or by other means, synthesized. A synthetic nucleic acid includes those that are chemically modified, or otherwise modified, but can base pair with (also referred to as "binding to," e.g., transiently or stably) naturally-occurring nucleic acid molecules. Recombinant and synthetic nucleic acids also include those molecules that result from the replication of either of the foregoing.

While an engineered nucleic acid, as a whole, is not naturally-occurring, it may include wild-type nucleotide sequences. In some embodiments, an engineered nucleic acid comprises nucleotide sequences obtained from different organisms (e.g., obtained from different species). For example, in some embodiments, an engineered nucleic acid includes a murine nucleotide sequence, a bacterial nucleotide sequence, a human nucleotide sequence, a viral nucleotide sequence, or a combination of any two or more of the foregoing sequences.

An engineered nucleic acid "construct" refers to an artificially constructed nucleic acid (e.g., including an assembly of DNA sequences) that can exist by itself in circular form and can be transfected into a cell. Engineered nucleic acid constructs of the present disclosure typically contain a DNA-binding domain recognition site, which guides cleavage and linearization of the construct by a programmable nuclease. Engineered nucleic acid constructs often contain all the elements necessary for expression of a gene of interest (e.g., selectable marker gene), including, for example, a promoter, the gene of interest (transgene) and a stop sequence. It should be understood, however, that engineered nucleic acid constructs of the present disclosure do not necessarily contain all the elements necessary for expression of a gene of interest. In some embodiments, as described elsewhere herein, an engineered construct comprises an activatable reporter cassette that contains a promoterless selectable marker gene.

Figure 2:
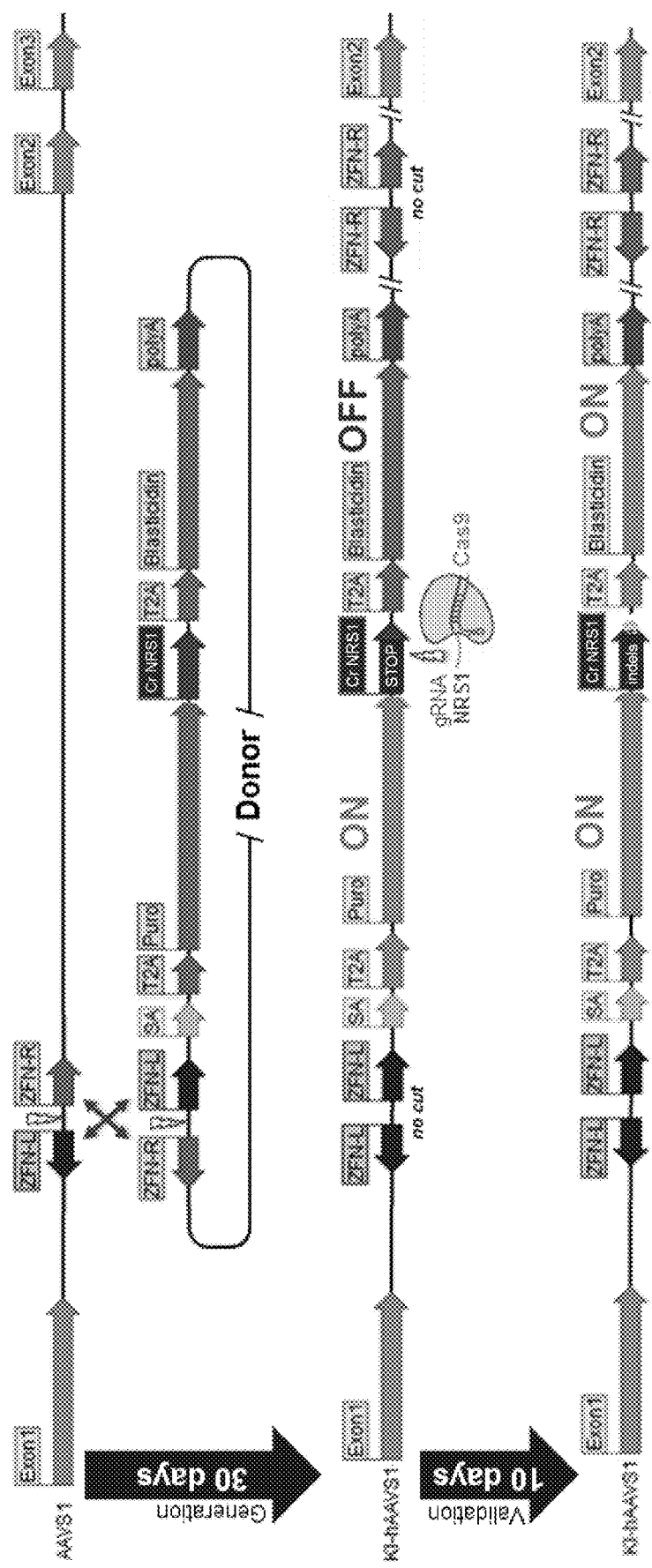
FIG. 2 shows schematics of examples of constructs used to generate cell lines expressing an activatable reporter cassette.
Figure 3:
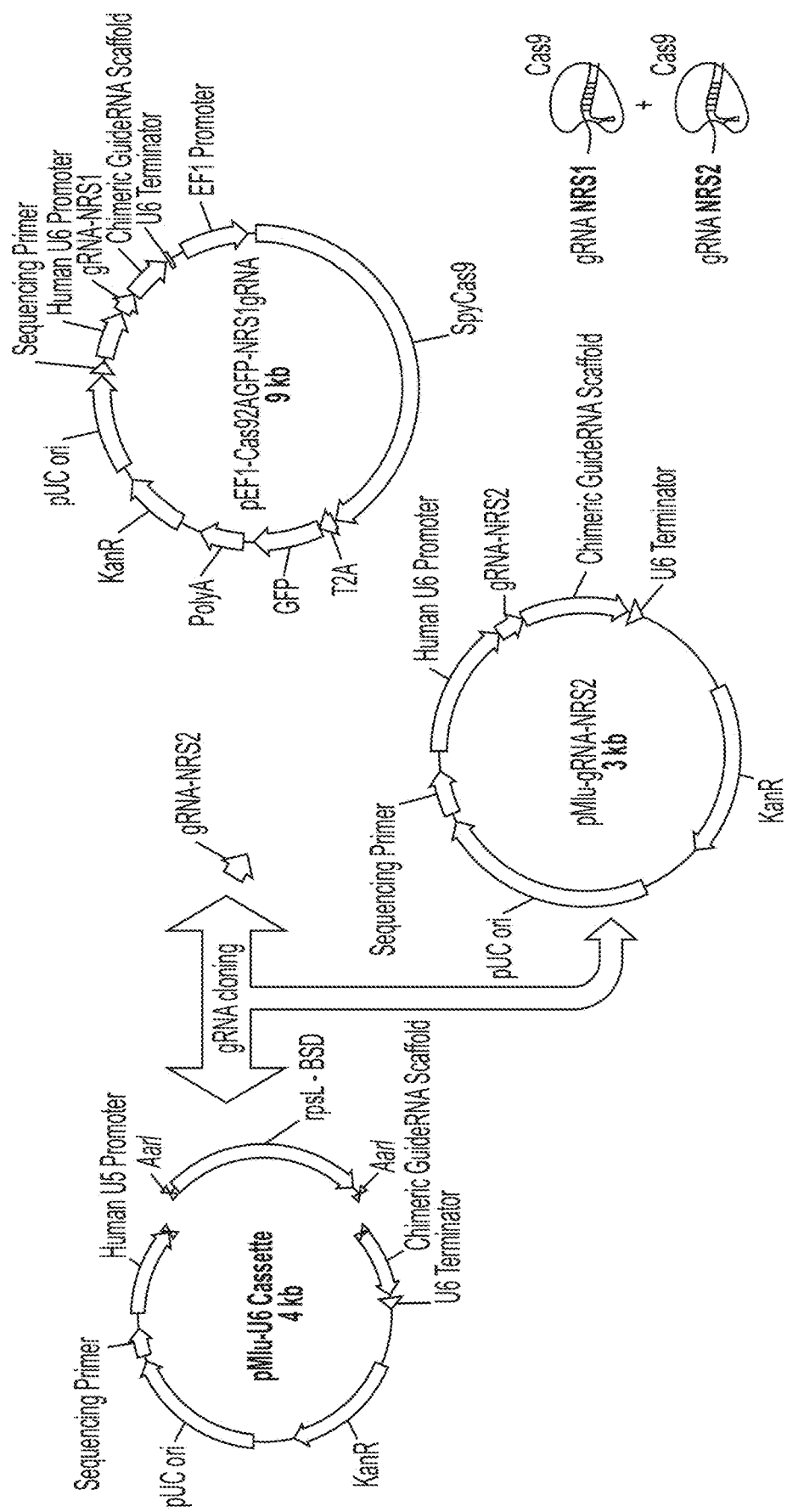
FIG. 3 shows schematic examples of Cas9 and gRNA-expressing plasmids.
Figure 4:
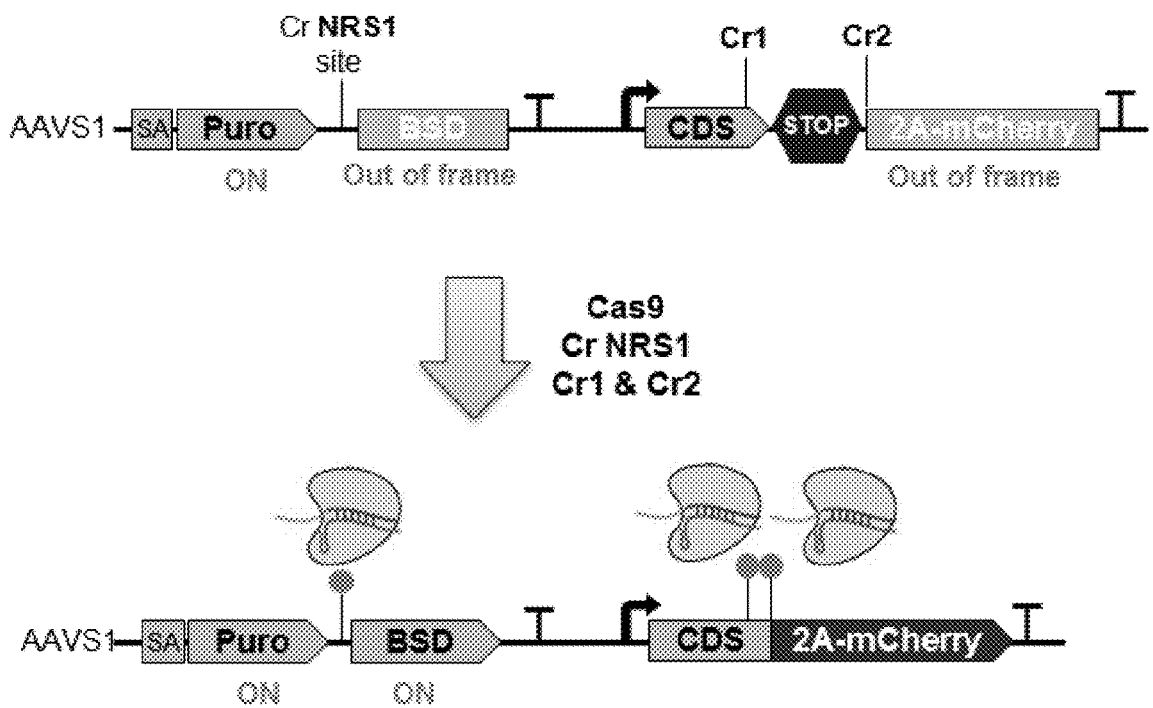
FIG. 4 shows an example of an activatable reporter cassette of the present disclosure.
Figure 5A:
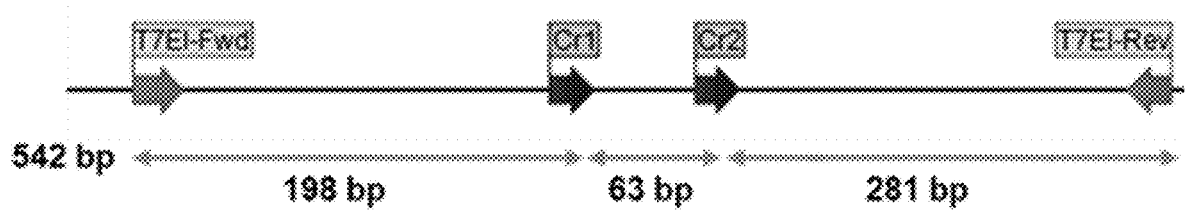
FIG. 5A shows a schematic depicting the location of two nuclease recognition target sites (Cr1 and Cr2) and primers used for amplifying the surrounding regions.

A nucleic acid "cassette," much like a "construct," refers to artificially constructed nucleic acid (e.g., including an assembly of DNA sequences). A cassette, however, does not exist by itself in circular form. A nucleic acid construct may comprise one or more nucleic acid cassettes. For example, FIG. 2 depicts a circular engineered nucleic acid construct (Donor), which includes an activatable reporter cassette. The activatable reporter cassette includes a nuclease recognition site (CrREM) flanked by a nucleic acid encoding puromycin N-acetyl-transferase and a downstream, out-of-frame selectable marker gene that encodes blasticidin S deaminase.

In some embodiments, an engineered nucleic acid of the present disclosure may comprise a backbone other than a phosphodiester backbone. For example, an engineered nucleic acid, in some embodiments, may comprise phosphoramide, phosphorothioate, phosphorodithioate, O-methylphophoroamidite linkages, peptide nucleic acids or a combination of any two or more of the foregoing linkages. An engineered nucleic acid may be single-stranded (ss) or double-stranded (ds), as specified, or an engineered nucleic acid may contain portions of both single-stranded and double-stranded sequence. In some embodiments, an engineered nucleic acid contains portions of triple-stranded sequence. An engineered nucleic acid may comprise DNA (e.g., genomic DNA, cDNA or a combination of genomic DNA and cDNA), RNA or a hybrid molecule, for example, where the nucleic acid contains any combination of deoxyribonucleotides and ribonucleotides (e.g., artificial or natural), and any combination of two or more bases, including uracil, adenine, thymine, cytosine, guanine, inosine, xanthine, hypoxanthine, isocytosine and isoguanine.

Engineered nucleic acids of the present disclosure may be produced using standard molecular biology methods (see, e.g., Green and Sambrook, Molecular Cloning, A Laboratory Manual, 2012, Cold Spring Harbor Press). In some embodiments, nucleic acids are produced using GIBSON ASSEMBLY® Cloning (see, e.g., Gibson, D. G. et al. Nature Methods, 343-345, 2009; and Gibson, D. G. et al. Nature Methods, 901-903, 2010, each of which is incorporated by reference herein). GIBSON ASSEMBLY® typically uses three enzymatic activities in a single-tube reaction: 5' exonuclease, the 3' extension activity of a DNA polymerase and DNA ligase activity. The 5' exonuclease activity chews back the 5' end sequences and exposes the complementary sequence for annealing. The polymerase activity then fills in the gaps on the annealed regions. A DNA ligase then seals the nick and covalently links the DNA fragments together. The overlapping sequence of adjoining fragments is much longer than those used in Golden Gate Assembly, and therefore results in a higher percentage of correct assemblies. Other methods of producing engineered nucleic acids are known in the art and may be used in accordance with the present disclosure.

Engineered nucleic acids of the present disclosure may include one or more genetic elements. A "genetic element" refers to a sequence of nucleotides that has a role in nucleic acid expression (e.g., promoters, insulators, enhancers, terminators and molecular (e.g., DNA or protein) binding regions) or encodes a product of a nucleic acid (e.g., a sequence of nucleotides encoding a nuclease).

Expression of engineered nucleic acids is typically driven by a promoter operably linked to the engineered nucleic acid. A "promoter" refers to a control region of a nucleic acid at which initiation and rate of transcription of the remainder of a nucleic acid sequence are controlled. A promoter drives transcription or of the nucleic acid sequence that it regulates, thus, it is typically located at or near the transcriptional start site of a gene. A promoter, in some embodiments, is 100 to 1000 nucleotides in length. A promoter may also contain sub-regions at which regulatory proteins and other molecules may bind, such as RNA polymerase and other transcription factors. Promoters may be constitutive (e.g., CAG promoter, cytomegalovirus (CMV) promoter), inducible (also referred to as activatable), repressible, tissue-specific, developmental stage-specific or any combination of two or more of the foregoing.

A promoter is considered to be "operably linked" when it is in a correct functional location and orientation relative to a sequence of nucleic acid that it regulates (e.g., to control ("drive") transcriptional initiation and/or expression of that sequence).

A promoter, in some embodiments, is naturally associated with a nucleic acid and may be obtained by isolating the 5' non-coding sequence(s) located upstream of the coding region of the given nucleic acid.

A promoter, in some embodiments, is not naturally associated with a nucleic acid. Such a promoter is referred to as a "heterologous" promoter and includes, for example, promoters that regulate other nucleic acids and promoters obtained from other cells. A heterologous promoter may be synthetic or recombinant. Synthetic heterologous promoters, in some embodiments, contain various elements obtained from known transcriptional regulatory regions. Synthetic heterologous promoters, in some embodiments, contain mutations that alter expression through methods of genetic engineering that are known in the art. Recombinant heterologous promoters, in some embodiments, are produced by recombinant cloning, nucleic acid amplification (e.g., polymerase chain reaction (PCR)), or a combination of recombinant cloning and nucleic acid amplification (see U.S. Pat. No. 4,683,202 and U.S. Pat. No. 5,928,906). Other methods of producing synthetic and recombinant heterologous promoters are contemplated herein.

A promoter, in some embodiments, is an inducible promoter. An "inducible promoter" regulates (e.g., activates or inactivates) transcriptional activity of a nucleic acid to which it is operably linked when the promoter is influenced by or contacted by a corresponding regulatory protein. Examples of inducible promoters include, without limitation, chemically- or biochemically-regulated and physically-regulated promoters, such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells). Other inducible promoters are known in the art and may be used in accordance with the present disclosure.

Engineered nucleic acids, in some embodiments, comprise enhancers. An "enhancer" is a cis-acting regulatory sequence of nucleotides involved in the transcriptional activation of a nucleic acid sequence operably linked to a promoter. The enhancer may be located at any functional location upstream or downstream from the promoter.

Engineered nucleic acids, in some embodiments, comprise terminators. A "terminator" is a sequence of nucleotides that causes transcription to stop. A terminator may be unidirectional or bidirectional. A terminator comprises a DNA sequence involved in specific termination of an RNA transcript by an RNA polymerase and prevents transcriptional activation of downstream nucleic acid sequences by upstream promoters.

The most commonly used type of terminator is a forward terminator. When placed downstream of a nucleic acid sequence that is usually transcribed, a forward transcriptional terminator will cause transcription to abort. In some embodiments, bidirectional transcriptional terminators are used, which usually cause transcription to terminate on both the forward and reverse strand. In some embodiments, reverse transcriptional terminators are provided, which usually terminate transcription on the reverse strand only.

Examples of terminators for use in accordance with the present disclosure include, without limitation, termination sequences of genes such as, for example, the bovine growth hormone terminator, and viral termination sequences such as, for example, the T0 terminator, the TE terminator, Lambda T1 and the T1T2 terminator found in bacterial systems. In some embodiments, the termination signal may be a sequence that cannot be transcribed or translated, such as those resulting from a sequence truncation.

Cells

Engineered constructs of the present disclosure may be introduced into a variety of different cells. Examples of cells into which an engineered construct may be introduced include, without limitation, mammalian cells, insect cells, bacterial cells (e.g., *Escherichia coli* cells) and yeast cells (e.g., *Saccharomyces cerevisiae* cells). Mammalian cells may be human cells, primate cells (e.g., vero cells), rat cells (e.g., GH3 cells, OC23 cells) or mouse cells (e.g., MC3T3 cells), for example. There are a variety of human cell lines, including, without limitation, HEK cells (e.g., HEK 293 or HEK 293T cells), HeLa cells, cancer cells from the National Cancer Institute's 60 cancer cell lines (NCI60), DU145 (prostate cancer) cells, Lncap (prostate cancer) cells, MCF-7 (breast cancer) cells, MDA-MB-438 (breast cancer) cells, PC3 (prostate cancer) cells, T47D (breast cancer) cells, THP-1 (acute myeloid leukemia) cells, U87 (glioblastoma) cells, SHSY5Y human neuroblastoma cells (cloned from a myeloma) and Saos-2 (bone cancer) cells.

In some embodiments, engineered constructs are expressed in stem cells (e.g., human stem cells) such as, for example, pluripotent stem cells (e.g., human pluripotent stem cells including human induced pluripotent stem cells (hiPSCs)). A "stem cell" refers to a cell with the ability to divide for indefinite periods in culture and to give rise to specialized cells. A "pluripotent stem cell" refers to a type of stem cell that is capable of differentiating into all tissues of an organism, but not alone capable of sustaining full organismal development. A "human induced pluripotent stem cell" refers to a somatic (e.g., mature or adult) cell that has been reprogrammed to an embryonic stem cell-like state by being forced to express genes and factors important for maintaining the defining properties of embryonic stem cells (see, e.g., Takahashi and Yamanaka, 2006 *Cell* 126 (4): 663-76, incorporated by reference herein). Human induced pluripotent stem cell express stem cell markers and are capable of generating cells characteristic of all three germ layers (ectoderm, endoderm, mesoderm).

Additional non-limiting examples of cell lines that may be used in accordance with the present disclosure include 293-T, 293-T, 3T3, 4T1, 721, 9L, A-549, A172, A20, A253, A2780, A2780ADR, A2780cis, A431, ALC, B16, B35, BCP-1, BEAS-2B, bEnd.3, BHK-21, BR 293, BxPC3, C2C12, C3H-10T1/2, C6, C6/36, Cal-27, CGR8, CHO, CML T1, CMT, COR-L23, COR-L23/5010, COR-L23/CPR, COR-L23/R23, COS-7, COV-434, CT26, D17, DH82, DU145, DuCaP, E14Tg2a, EL4, EM2, EM3, EMT6/AR1, EMT6/AR10.0, FM3, H1299, H69, HB54, HB55, HCA2, Hepa1c1c7, High Five cells, HL-60, HMEC, HT-29, HUVEC, J558L cells, Jurkat, JY cells, K562 cells, KCL22, KG1, Ku812, KYO1, LNCap, Ma-Mel 1, 2, 3 . . . 48, MC-38, MCF-10A, MCF-7, MDA-MB-231, MDA-MB-435, MDA-MB-468, MDCK II, MG63, MONO-MAC 6, MOR/0.2R, MRCS, MTD-1A, MyEnd, NALM-1, NCI-H69/CPR, NCI-H69/LX10, NCI-H69/LX20, NCI-H69/LX4, NIH-3T3, NW-145, OPCN/OPCT Peer, PNT-1A/PNT 2, PTK2, Raji, RBL cells, RenCa, RIN-5F, RMA/RMAS, S2, Saos-2 cells, Sf21, Sf9, SiHa, SKBR3, SKOV-3, T-47D, T2, T84, THP1, U373, U87, U937, VCaP, WM39, WT-49, X63, YAC-1 and YAR cells.

Cells of the present disclosure, in some embodiments, are modified. A modified cell is a cell that contains an exogenous nucleic acid or a nucleic acid that does not occur in nature. In some embodiments, a modified cell contains a mutation in a genomic nucleic acid. In some embodiments, a modified cell contains an exogenous independently replicating nucleic acid (e.g., an engineered nucleic acid present on an episomal vector). In some embodiments, a modified cell is produced by introducing a foreign or exogenous nucleic acid into a cell.

An engineered construct may be introduced into a cell by methods, such as, for example, electroporation (see, e.g., Heiser W. C. *Transcription Factor Protocols: Methods in Molecular Biology*™ 2000; 130: 117-134), chemical (e.g., calcium phosphate or lipid), transfection (see, e.g., Lewis W. H., et al., *Somatic Cell Genet.* 1980 May; 6(3): 333-47; Chen C., et al., *Mol Cell Biol.* 1987 August; 7(8): 2745-2752), fusion with bacterial protoplasts containing recombinant plasmids (see, e.g., Schaffner W. *Proc Natl Acad Sci USA.* 1980 April; 77(4): 2163-7), or microinjection of purified DNA directly into the nucleus of the cell (see, e.g., Capecchi M. R. *Cell.* 1980 November; 22(2 Pt 2): 479-88).

Mammalian cells (e.g., human cells) modified to comprise an engineered construct of the present disclosure may be cultured (e.g., maintained in cell culture) using conventional mammalian cell culture methods (see, e.g., Phelan M. C. *Curr Protoc Cell Biol.* 2007 September; Chapter 1: Unit 1.1, incorporated by reference herein). For example, cells may be grown and maintained at an appropriate temperature and gas mixture (e.g., 37° C., 5% $CO_2$ for mammalian cells) in a cell incubator. Culture conditions may vary for each cell type. For example, cell growth media may vary in pH, glucose concentration, growth factors, and the presence of other nutrients. Growth factors used to supplement media are often derived from the serum of animal blood, such as fetal bovine serum (FBS), bovine calf serum, equine serum and/or porcine serum. In some embodiments, culture media used as provided herein may be commercially available and/or well-described (see, e.g., Birch J. R., R. G. Spier (Ed.) Encyclopedia of Cell Technology, Wiley. 411-424, 2000; Keen M. J. *Cytotechnology* 17: 125-132, 1995; Zang, et al. *Bio/Technology.* 13: 389-392, 1995). In some embodiments, chemically defined media is used.

Methods of Producing Cells for Gene Modification Assays

The activatable reporter cassette-based systems of the present disclosure typically require an activatable reporter cassette having a nuclease recognition site (NRS1), a target gene having a nuclease recognition site (NRS2), an RNA-guided nuclease (e.g., Cas9 or Cpf1) and two gRNAs: one targeting the activatable reporter cassette and one targeting the target gene. The present disclosure encompasses a variety of methods of producing cells that comprise the foregoing tools.

For example, gRNAs, or nucleic acids encoding gRNAs, may be transfected into cells that already express a target gene, an activatable reporter cassette (e.g., having been transfected previously) and an RNA-guided nuclease (e.g., Cas9 or Cpf1). Thus, in some embodiments, methods of producing cells for a gene modification assay comprise transfecting cells that express (a) a target gene of interest that comprises a nuclease recognition site specific to the target gene of interest, (b) an activatable reporter cassette that comprises a nuclease recognition site flanked by an upstream selectable marker gene and a downstream out-of-frame selectable marker gene that is different from the upstream selectable marker gene, and (c) a RNA-guided nuclease that cleaves the nuclease recognition site of (a) and (b), with at least one engineered nucleic acid that encodes a guide RNA (gRNA) complementary to the nuclease recognition site of (a) and a gRNA complementary to the nuclease recognition site of (b), thereby producing cells for a gene modification assay. It should be understood that, in some embodiments, cells are transfected with gRNAs (rather than nucleic acids encoding gRNAs). In some embodiments, methods of producing cells for a gene modification assay comprise (a) transfecting a first population of cells that express (i) a first target gene of interest that comprises a nuclease recognition site specific to the first target gene of interest, (ii) an activatable reporter cassette that comprises a nuclease recognition site flanked by an upstream selectable marker gene and a downstream out-of-frame selectable marker gene that is different from the upstream selectable marker gene, and (iii) a RNA-guided nuclease that cleaves the nuclease recognition site of (a)(i) and the nuclease recognition site of (a)(ii), with at least one engineered nucleic acid that encodes a guide RNA (gRNA) complementary to the nuclease recognition site of (a)(i) and a gRNA complementary to the nuclease recognition site of (a)(ii), and (b) transfecting a second population of cells that express (i) a second target gene of interest that comprises a nuclease recognition site, (ii) an activatable reporter cassette that comprises a nuclease recognition site flanked by an upstream selectable marker gene and a downstream out-of-frame selectable marker gene that is different from the upstream selectable marker gene, and (iii) a RNA-guided nuclease that cleaves the nuclease recognition site of (b)(i) and the nuclease recognition site of (b)(ii) with at least one engineered nucleic acid that encodes a guide RNA (gRNA) complementary to the nuclease recognition site of (b)(i) and a gRNA complementary to the nuclease recognition site of (b)(ii), thereby producing cells for a gene modification assay.

As another example, gRNAs, or nucleic acids encoding gRNAs, may be transfected into cells that already express a target gene and an activatable reporter cassette, but not an RNA-guided nuclease (e.g., Cas9). Thus, in some embodiments, methods of producing cells for a gene modification assay comprise transfecting cells that express (a) a target gene of interest that comprises a nuclease recognition site specific to the target gene of interest and (b) an activatable reporter cassette that comprises a nuclease recognition site flanked by an upstream selectable marker gene and a downstream out-of-frame selectable marker gene that is different from the upstream selectable marker gene, with at least one engineered nucleic acid that encodes a guide RNA (gRNA) complementary to the nuclease recognition site of (a) and a gRNA complementary to the nuclease recognition site of (b), thereby producing cells for a gene modification assay. In some embodiments, the at least one engineered nucleic acid further encodes an RNA-guided nuclease that cleaves the nuclease recognition site of (a) and (b). In some embodiments, the methods further comprise transfecting the cells with an engineered nucleic acid encoding a RNA-guided nuclease that cleaves the nuclease recognition site of (a) and (b). In some embodiments, purified RNA-guided nuclease (e.g., Cas9 or Cpf1) may be introduced into the cells.

As yet another example, an activatable reporter cassette and gRNAs, or nucleic acids encoding gRNAs, may be transfected into cells that already express or include a target gene and an RNA-guided nuclease (e.g., Cas9). Thus, in some embodiments, methods of producing cells for a gene modification assay comprise transfecting cells that express (a) a target gene of interest that comprises a nuclease recognition site specific to the target gene of interest and (b) a RNA-guided nuclease that cleaves the nuclease recognition site of the target gene of interest and cleaves a nuclease recognition site of an activatable reporter cassette, with an engineered nucleic acid construct comprising a deoxyribonucleic acid-binding domain recognition site (DNA-BDRS) and an activatable reporter cassette that comprises a nuclease recognition site flanked by an upstream selectable marker gene and a downstream an out-of-frame selectable marker gene that is different from the upstream selectable marker gene.

As still another example, an activatable reporter cassette and gRNAs, or nucleic acids encoding gRNAs, may be transfected into cells that already express a target gene but not an RNA-guided nuclease (e.g., Cas9). Thus, in some embodiments, methods of producing cells for a gene modification assay comprise transfecting cells that express a target gene of interest that comprises a nuclease recognition site specific to the target gene of interest with an engineered nucleic acid construct comprising a deoxyribonucleic acid-binding domain recognition site (DNA-BDRS) and an activatable reporter cassette that comprises a nuclease recognition site flanked by an upstream selectable marker gene and a downstream an out-of-frame selectable marker gene that is different from the upstream selectable marker gene. In some embodiments, the at least one engineered nucleic acid that encodes the gRNAs further encodes a RNA-guided nuclease that cleaves the nuclease recognition site of the target gene of interest and cleaves the nuclease recognition site of the activatable reporter cassette. In some embodiments, the engineered nucleic acid construct that encodes the DNA-BDRS and the activatable reporter construct further encodes a nuclease that cleaves the nuclease recognition site of the target gene of interest and cleaves the nuclease recognition site of the activatable reporter cassette. In some embodiments, the methods further comprise transfecting the cells with a nucleic acid encoding an RNA-guided nuclease that cleaves the nuclease recognition site of the target gene of interest and cleaves the nuclease recognition site of the activatable reporter cassette.

Applications

Figure 18A:
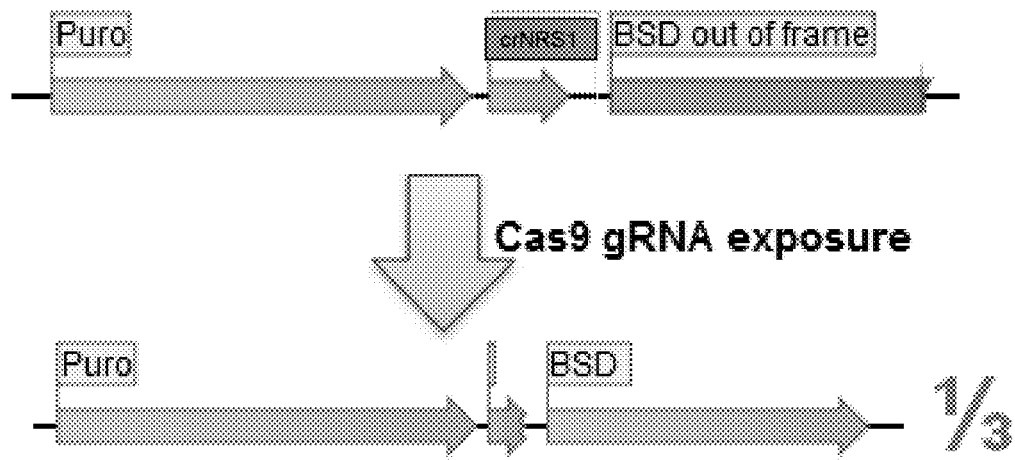
FIGS. 18A-18B show that a CrNRS1 located upstream from out-of-frame selection markers can be presented as single or dual gRNA.
Figure 18B:
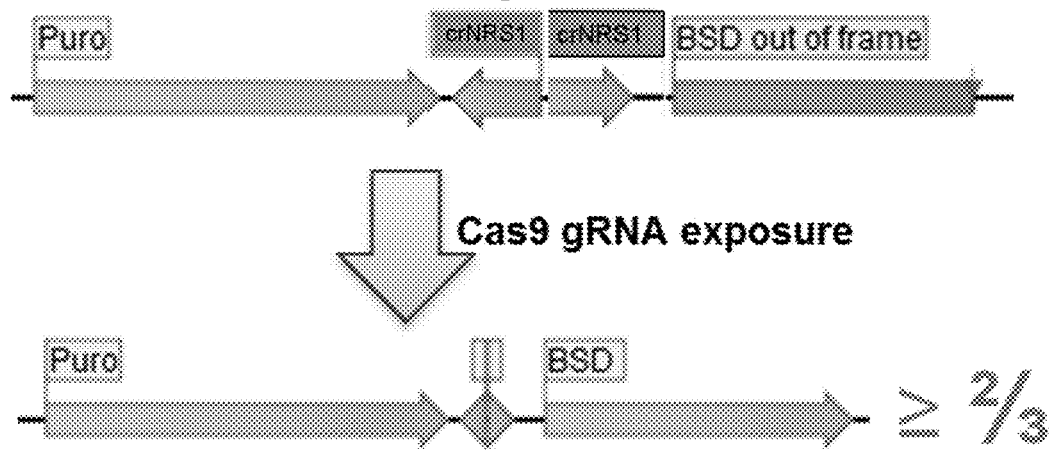
Figure 19:
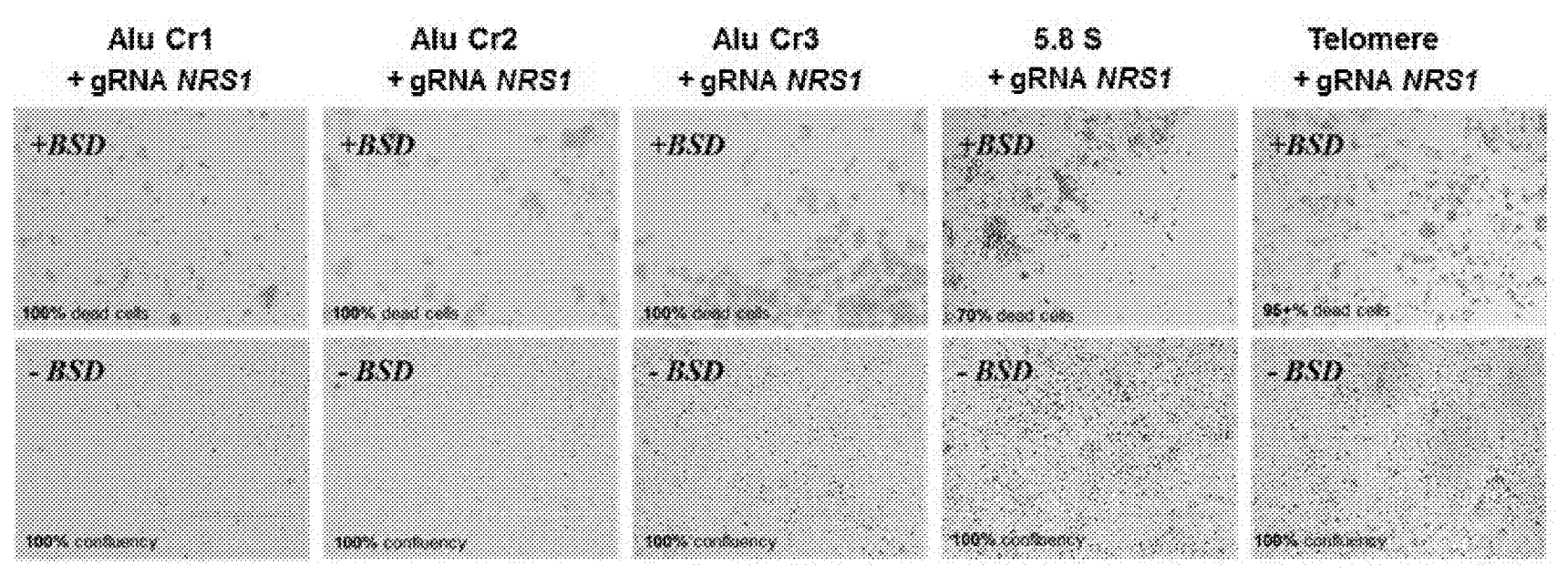
Figure 20:
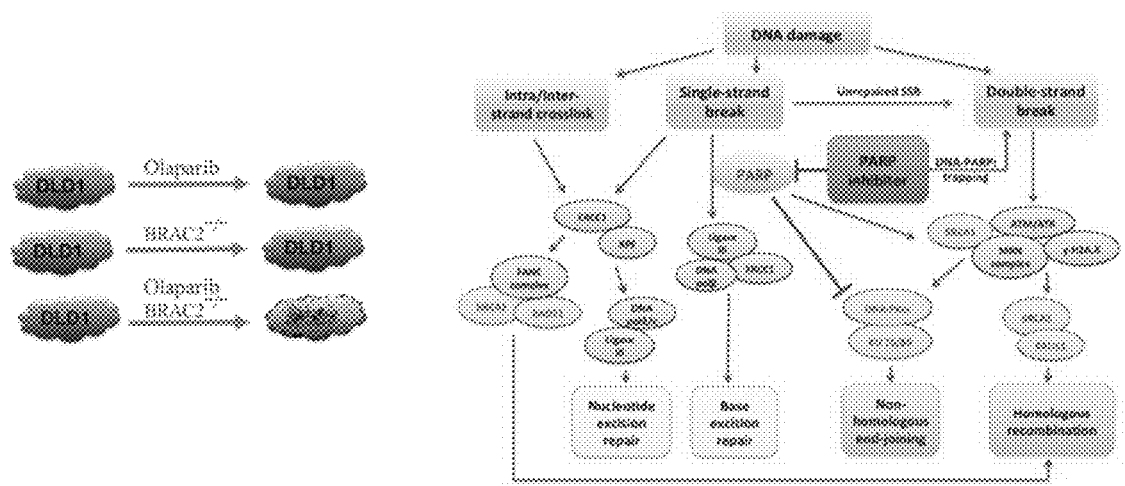
FIG. 20 schematizes a synthetic lethality screen in which combination of two or more factors (e.g., altered genes) leads to cell death while each affected single gene does not. This application may be used to identify "targeted therapeutics" for selectively killing tumor cells.
Figure 21:
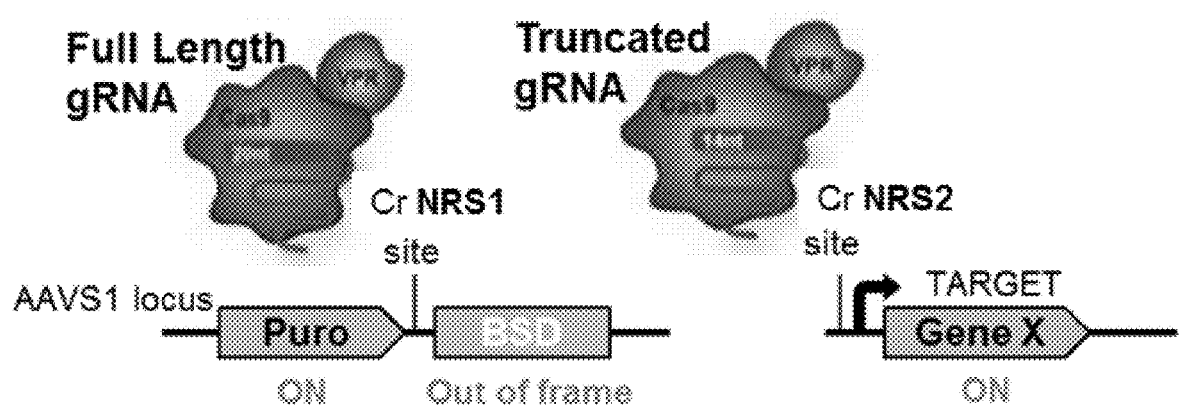
FIG. 21 shows a schematic depicting an activatable reporter cassette used for CRISPRa/i. For example, cells receive a full length gRNA targeting the CrNRS1 site of the activatable reporter cassette along with a wildtype Cas9 fused to an activation/repression (inactivation) domain. Co-delivery of a truncated gRNA for directing the Cas9 to a promoter region of Gene X can result in gene activation. Selection for BSD-activated cells can be translated as an enrichment of cells with activated/repressed GeneX.
Figure 22:
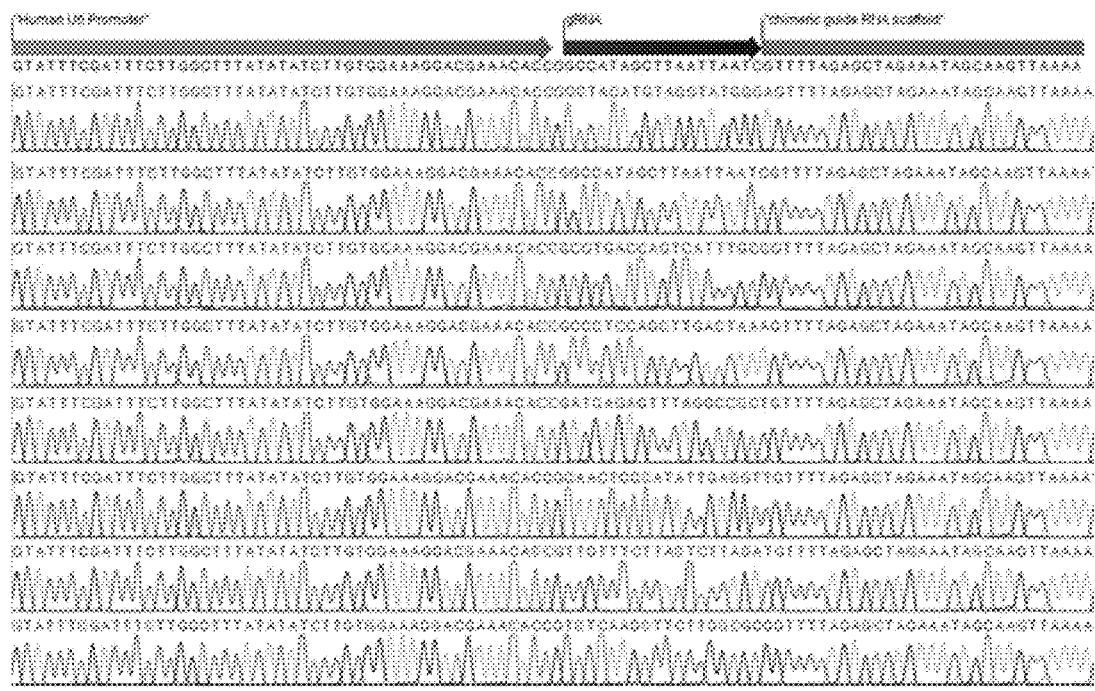
FIG. 22 shows results from quality controls tests for high-throughput gRNA cloning for a CRISPR knockout screen (SEQ ID NOS 156-164, respectively, in order for appearece). 94 out of 96 gRNAs were correctly cloned and verified by Sanger Sequencing.
Figure 23A:
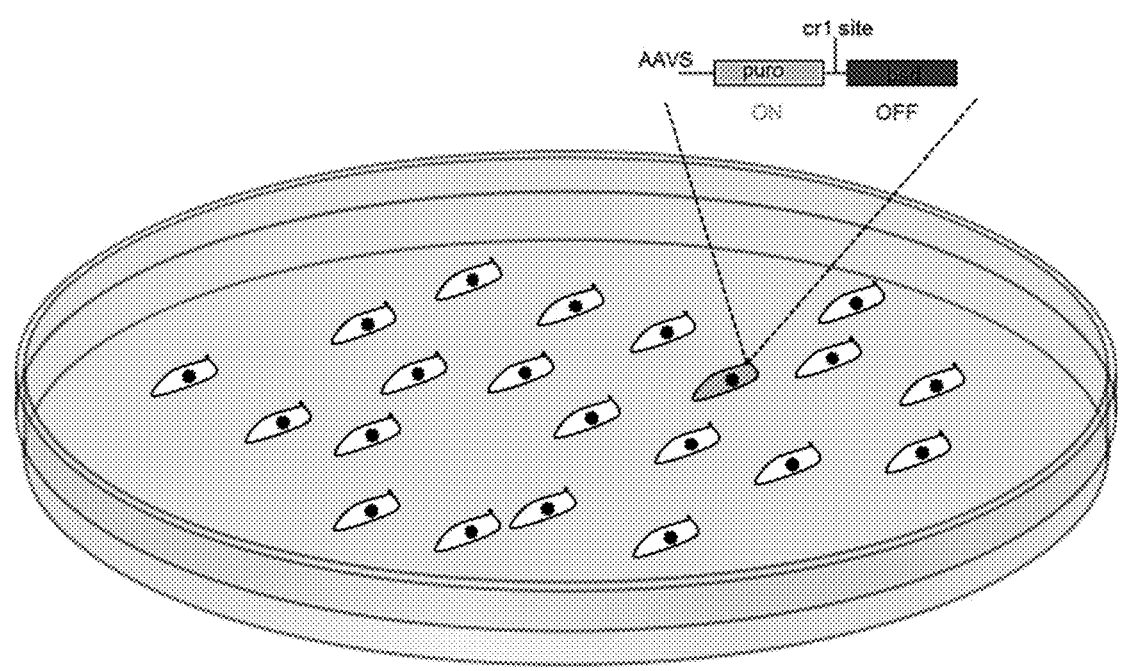
FIGS. 23A-23C show an example of a method of barcoding cells using an activatable reporter cassette. The GFP-positive cell (shaded gray) (FIG. 23A) has a particular barcode represented by an activatable reporter cassette (having an NRS1 site). This barcode is specific for this cell, and therefore blasticidin resistance can be obtained only in the cell upon transfection with gRNA against NRS1 and Cas9. In some embodiments, $10^{12}$ barcodes may be used, and all single cells in an experiment (e.g., on a single plate) can be isolated. Blasticidin selection (after selection with a particular gRNA) may be used to isolate a specific cell associated with a specific barcode.
Figure 23B:
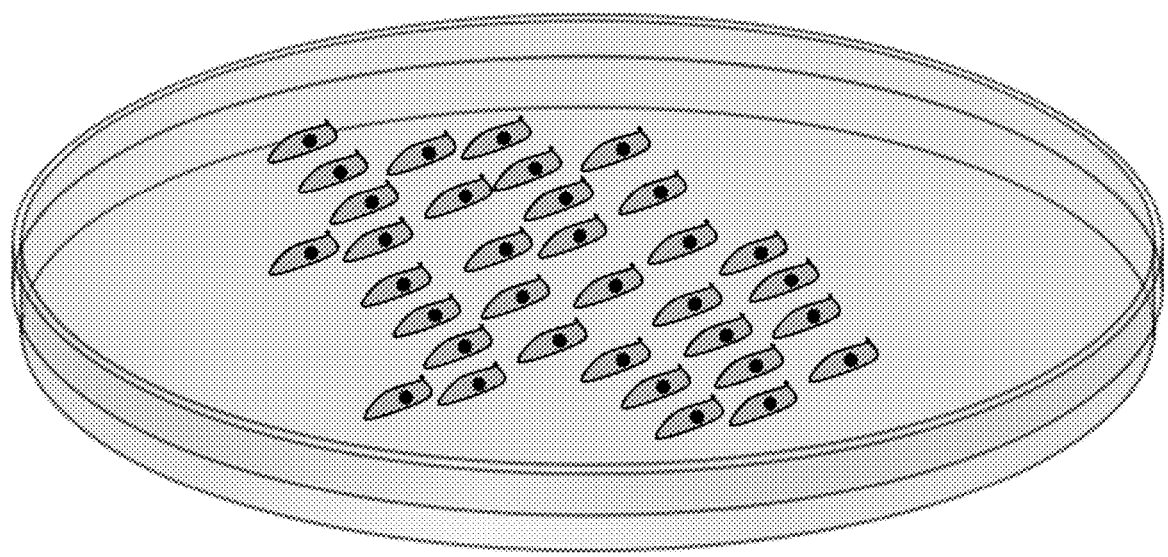
Figure 23C:
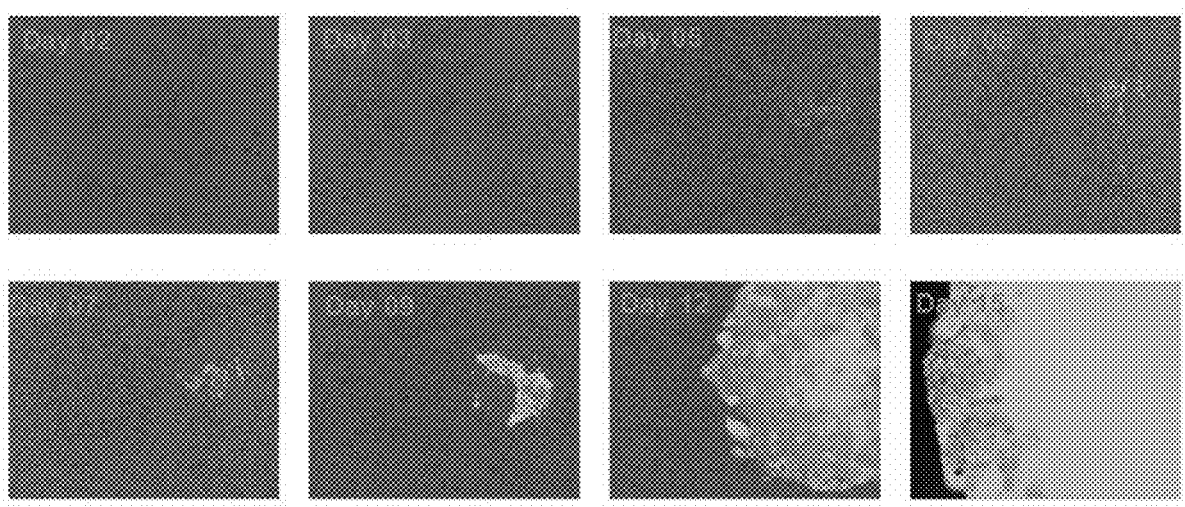

The engineered nucleic acid constructs of the present disclosure, including the activatable reporter cassettes, may be used in a variety of applications, including, without limitation, synthetic lethality screens (see, e.g., FIGS. 18-20), CRISPRi/a (inactivation/activation) screens (FIG. 21), CRISPR/Cas9 knockout arrayed screening assays (see, e.g., FIG. 22), off-target detection assays, cell line generation (e.g., enrichment for knockin events), pooled-to-arrayed screening and barcoding (FIGS. 23A-23C). Other applications and uses of the activatable reporter cassettes include, without limitation, single cell analysis, isolation of specific mutations among a population of cells, analyzing drug resistance in cells, antibody generation, isolation of clones capable of high protein production, and genome-wide tagging and isolation. See, e.g., Mali P, et al. *Science*. 2013 Feb. 15; 339(6121):823-6; Want T, et al. *Science*. 2014 Jan. 3; 343(6166):80-4; Shalem O, et al. *Science*. 2014 Jan. 3; 343(6166):84-7; Koike-Yusa H, et al. *Nat Biotechnol*. 2014 March; 32(3):267-73; and Zhou Z, et al. *Nature*. 2014 May 22; 509(7501):487-91.

In some embodiments, an activatable reporter cassette may be used to generate a knock-out cell or organism. For example, a knock-out cell may be generated by co-expressing in a cell (or introducing into a cell) an activatable reporter cassette, a gRNA specific to the nuclease recognition site of the activatable reporter cassette, a gRNA specific to a nuclease recognition site present in a target gene of interest and an RNA-guided nuclease (e.g., Cas9 or Cpf1) that cleaves the nuclease recognition sites. In some embodiments, the target gene contains an ~20 nucleotide DNA sequence that is specific to the target gene and the target sequence is immediately upstream of a protospacer adjacent motif (PAM).

In some embodiments, an activatable reporter cassette may be used to activate or repress a target gene. One feature of Cas9, for example, is its ability to bind target DNA independently of its ability to cleave target DNA. Specifically, both RuvC- and HNH-nuclease domains can be rendered inactive by point mutations (D10A and H840A in SpCas9), resulting in a nuclease dead Cas9 (dCas9) molecule that cannot cleave target DNA. The dCas9 molecule retains the ability to bind to target DNA based on the gRNA targeting sequence. In some embodiments, dCas9 may be targeted to transcriptional start sites to "repress" or "knockdown" transcription by blocking transcription initiation. In some embodiments, dCas9 may be tagged with transcriptional repressors or activators, and these dCas9 fusion proteins may be targeted to a promoter region, resulting in robust transcription repression or activation of downstream target genes. The simplest dCas9-based activators and repressors include dCas9 fused directly to a single transcriptional activator, A (e.g., VP64) or transcriptional repressors, R (e.g., KRAB). In some embodiments, a target gene in a cell may be activated or repressed by co-expressing in a cell (or introducing into a cell) an activatable reporter cassette, a gRNA specific to the nuclease recognition site of the activatable reporter cassette, a Cas9 or Cpf1 nuclease, a gRNA specific to a transcriptional start site of a target gene, and a dCas9-based activator or repressor.

In some embodiments, an activatable reporter cassette may be used for genome-wide screening applications.

In some embodiments, the methods provided herein are virus-free. That is, the methods do not require the use of a viral-based delivery system. It should be understood, however, that while the engineered nucleic acids of the present disclosure may be inserted in a precise and predetermined location of a genome without the use of viral vectors, in some embodiments, delivery of the constructs may be randomly introduced in a genome via a viral vector (e.g., a lentiviral vector).

The present disclosure also provides composition and kits comprising at least one of the engineered nucleic acid constructs (e.g., activatable reporter cassettes) of the present disclosure.

The present disclosure further provides embodiments encompassed by the following numbered paragraphs:

1. An engineered nucleic acid construct comprising a deoxyribonucleic acid-binding domain recognition site (DNA-BDRS) and an activatable reporter cassette that comprises a nuclease recognition site flanked by an upstream selectable marker gene and a downstream out-of-frame selectable marker gene that is different from the upstream selectable marker gene.

2. The engineered nucleic acid construct of paragraph 1, wherein the upstream selectable marker gene is promoter-less.

3. The engineered nucleic acid construct of paragraph 1, wherein the upstream selectable marker gene is operably linked to a promoter.

4. The engineered nucleic acid construct of any one of paragraphs 1-3, further comprising a nucleic acid encoding a gene of interest.

5. The engineered nucleic acid construct of paragraph 4, wherein the gene of interest encodes a nuclease.

6. The engineered nucleic acid construct of paragraph 5, wherein the nuclease is Cas9.

7. The engineered nucleic acid construct of paragraph 5, wherein the nuclease is Cpf1.

8. A cell comprising (a) a target gene of interest that comprises at least one nuclease recognition site, (b) the engineered nucleic acid construct of any one of paragraphs 1-7, and (c) a programmable nuclease that binds to the DNA-BDRS.

9. The cell of paragraph 8, wherein the programmable nuclease is a zinc finger nuclease, a transcription activator-like effector nuclease or a Cas9-FokI nuclease.

10. The cell of paragraph 8 or 9 further comprising a nuclease that cleaves the nuclease recognition site of the activatable reporter cassette and cleaves the nuclease recognition site of the target gene of interest.

11. The cell of paragraph 10, wherein the nuclease is Cas9.

12. The cell of paragraph 10, wherein the nuclease is Cpf1.

13. The cell of any one of paragraphs 8-12 further comprising a guide RNA (gRNA) complementary to the nuclease recognition site of the activatable reporter cassette and a gRNA complementary to the nuclease recognition site of the target gene of interest.

14. The cell of paragraph 13, wherein the gRNA complementary to the nuclease recognition site of the activatable reporter cassette and the gRNA complementary to the nuclease recognition site of the target gene of interest are encoded by engineered nucleic acids located on the same construct.

15. The cell of paragraph 14, wherein the construct further comprises a nucleic acid encoding the nuclease.

16. The cell of any one of paragraphs 8-15 comprising multiple gRNAs, each complementary to a different nuclease recognition site of the target gene of interest.

17. The cell of any one of paragraphs 8-16, wherein the selectable marker encoded by the upstream selectable marker gene confers puromycin resistance, blasticidin S deaminase resistance, ampicillin resistance, kanamycin resistance, geneticin resistance, hygromycin resistance, clonNAT resistance or triclosan resistance to the cell.

18. The cell of any one of paragraphs 8-17, wherein the selectable marker encoded by the downstream selectable marker gene confers puromycin resistance, blasticidin S deaminase resistance, ampicillin resistance, kanamycin resistance, geneticin resistance, hygromycin resistance, clonNAT resistance or triclosan resistance to the cell.

19. The cell of any one of paragraphs 8-18, wherein the nuclease recognition site of the activatable reporter cassette is not otherwise present in the genome of the cell.

20. The cell of any one of paragraphs 8-19, wherein the cell is a bacterial cell.

21. The cell of any one of paragraphs 8-19, wherein the cell is a mammalian cell.

22. The cell of paragraph 21, wherein the mammalian cell is a human cell.

23. The cell paragraph 21 or 22, wherein the cell is a pluripotent stem cell.

24. The cell of paragraph 23, wherein the cell is an induced pluripotent stem cell 25. A population of cells comprising the cells of any one of paragraphs 8-24.

26. A culture comprising cell media and the population of cells of paragraph 25.

27. A cell expressing: (a) a target gene of interest that comprises a nuclease recognition site specific to the target gene of interest; (b) an activatable reporter cassette comprising a nuclease recognition site flanked by an upstream selectable marker gene and a downstream out-of-frame selectable marker gene that is different from the upstream selectable marker gene; (c) a nuclease that cleaves the nuclease recognition site of the activatable reporter cassette and cleaves the nuclease recognition site of the target gene of interest; and (d) a guide RNA (gRNA) complementary to the nuclease recognition site of the activatable reporter cassette and a gRNA complementary to the nuclease recognition site of the target gene of interest.

28. The cell of paragraph 27, wherein the selectable marker encoded by the upstream selectable marker gene confers puromycin resistance, blasticidin S deaminase resistance, ampicillin resistance, kanamycin resistance, geneticin resistance, or triclosan resistance to the cell.

29. The cell of paragraph 27 or 28, wherein the selectable marker encoded by the downstream selectable marker gene confers puromycin resistance, blasticidin S deaminase resistance, ampicillin resistance, kanamycin resistance, geneticin resistance, or triclosan resistance to the cell.

30. The cell of any one of paragraphs 27-29, wherein the cell is a mammalian cell.

31. The cell of paragraph 30, wherein the mammalian cell is a human cell.

32. The cell of any one of paragraphs 27-31, wherein the cell is a pluripotent stem cell.

33. The cell of paragraph 32, wherein the cell is an induced pluripotent stem cell.

34. A method of producing cells for a gene modification assay, comprising: transfecting cells that express (a) a target gene of interest that comprises a nuclease recognition site specific to the target gene of interest, (b) an activatable reporter cassette that comprises a nuclease recognition site flanked by an upstream selectable marker gene and a downstream out-of-frame selectable marker gene that is different from the upstream selectable marker gene, and (c) a nuclease that cleaves the nuclease recognition site of (a) and (b), with at least one engineered nucleic acid that encodes a guide RNA (gRNA) complementary to the nuclease recognition site of (a) and a gRNA complementary to the nuclease recognition site of (b), thereby producing cells for a gene modification assay.

35. The method of paragraph 34, wherein the at least one engineered nucleic acid includes: (a) a first nucleotide sequence that encodes a gRNA complementary to a nuclease recognition site of a first target gene of interest expressed by the cells and encodes a gRNA complementary to the nuclease recognition site of the activatable reporter cassette; and a second nucleotide sequence that encodes a gRNA complementary to a nuclease recognition site of a second target gene of interest expressed by the cells and encodes a gRNA complementary to the nuclease recognition site of the activatable reporter cassette.

36. The method of paragraph 34, wherein the at least one engineered nucleic acid includes: a first nucleotide sequence that encodes a gRNA complementary to a first nuclease recognition site of the target gene of interest and encodes a gRNA complementary to the nuclease recognition site of the activatable reporter cassette; and a second nucleotide sequence that encodes a gRNA complementary to a second nuclease recognition site of the target gene of interest and encodes a gRNA complementary to the nuclease recognition site of the activatable reporter cassette.

37. The method of paragraph 34, wherein the at least one engineered nucleic acid encodes at least three gRNAs: a first gRNA complementary to a first nuclease recognition site of the target gene of interest; a second gRNA complementary to a second nuclease recognition site of the target gene of interest; and a third gRNA complementary to the nuclease recognition site of the activatable reporter cassette.

38. The method of any one of paragraphs 34-37 further comprising incubating the cells under conditions that result in cleavage of the nuclease recognition site of (a), cleavage of the nuclease recognition site of (b), and reconfiguration of the downstream selectable marker gene from out-of-frame to in-frame with the upstream selectable marker gene.

39. The method of paragraph 38 further comprising selecting cells that express the downstream selectable marker.

40. The method of paragraph 39 further comprising analyzing phenotypes of cells that express the downstream selectable marker.

41. A method of producing cells for a gene modification assay, comprising: (a) transfecting a first population of cells that express (i) a first target gene of interest that comprises a nuclease recognition site specific to the first target gene of interest, (ii) an activatable reporter cassette that comprises a nuclease recognition site flanked by an upstream selectable marker gene and a downstream out-of-frame selectable marker gene that is different from the upstream selectable marker gene, and (iii) a nuclease that cleaves the nuclease recognition site of (a)(i) and the nuclease recognition site of (a)(ii) with at least one engineered nucleic acid that encodes a guide RNA (gRNA) complementary to the nuclease recognition site of (a)(i) and a gRNA complementary to the nuclease recognition site of (a)(ii); and (b) transfecting a second population of cells that express (i) a second target gene of interest that comprises a nuclease recognition site, (ii) an activatable reporter cassette that comprises a nuclease recognition site flanked by an upstream selectable marker gene and a downstream out-of-frame selectable marker gene that is different from the upstream selectable marker gene, and (iii) a nuclease that cleaves the nuclease recognition site of (b)(i) and the nuclease recognition site of (b)(ii) with at least one engineered nucleic acid that encodes a guide RNA (gRNA) complementary to the nuclease recognition site of (b)(i) and a gRNA complementary to the nuclease recognition site of (b)(ii), thereby producing cells for a gene modification assay.

42. The method of paragraph 41 further comprising incubating cells of the first population and cells of the second population under conditions that result in cleavage of the nuclease recognition sites of (a)(i), (a)(ii), (b)(i) and (b)(ii) and reconfiguration of the downstream selectable marker gene of (a)(ii) and (b)(ii) from out-of-frame to in-frame with the upstream selectable marker gene of (a)(ii) and (b)(ii), respectively.

43. The method of paragraph 42 further comprising selecting cells of the first population that express a downstream selectable marker encoded by the downstream selectable marker gene of (a)(ii) and selecting cells of the second population that express a downstream selectable marker encoded by the downstream selectable marker gene of (b)(ii).

44. The method of paragraph 43 further comprising analyzing phenotypes of cells of the first population that express a downstream selectable marker encoded by the downstream selectable marker gene of (a)(ii) and analyzing phenotypes of cells of the second population that express a downstream selectable marker encoded by the downstream selectable marker gene of (b)(ii).

45. A method of producing cells for a gene modification assay, comprising: introducing into cells that express (a) a target gene of interest that comprises a nuclease recognition site specific to the target gene of interest, (b) an activatable reporter cassette that comprises a nuclease recognition site flanked by an upstream selectable marker gene and a downstream out-of-frame selectable marker gene that is different from the upstream selectable marker gene, and (c) a nuclease that cleaves the nuclease recognition site of (a) and (b) at least one engineered guide RNA (gRNA) complementary to the nuclease recognition site of (a) and a gRNA complementary to the nuclease recognition site of (b), thereby producing cells for a gene modification assay.

46. The method of paragraph 45, wherein the gRNAs are introduced into the cell through electroporation.

47. A method of producing cells for a gene modification assay, comprising: transfecting cells that express (a) a target gene of interest that comprises a nuclease recognition site specific to the target gene of interest and (b) an activatable reporter cassette that comprises a nuclease recognition site flanked by an upstream selectable marker gene and a downstream out-of-frame selectable marker gene that is different from the upstream selectable marker gene, with at least one engineered nucleic acid that encodes a guide RNA (gRNA) complementary to the nuclease recognition site of (a) and a gRNA complementary to the nuclease recognition site of (b), thereby producing cells for a gene modification assay.

48. The method of paragraph 47, wherein the at least one engineered nucleic acid includes: a first engineered nucleic acid that encodes a gRNA complementary to a nuclease recognition site of a first target gene of interest expressed by the cells and encodes a gRNA complementary to the nuclease recognition site of the activatable reporter cassette; and a second engineered nucleic acid that encodes a gRNA complementary to a nuclease recognition site of a second target gene of interest expressed by the cells and encodes a gRNA complementary to the nuclease recognition site of the activatable reporter cassette.

49. The method of paragraph 47, wherein the at least one engineered nucleic acid includes: a first engineered nucleic acid that encodes a gRNA complementary to a first nuclease recognition site of the target gene of interest and encodes a gRNA complementary to the nuclease recognition site of the activatable reporter cassette; and a second engineered nucleic acid that encodes a gRNA complementary to a second nuclease recognition site of the target gene of interest and encodes a gRNA complementary to the nuclease recognition site of the activatable reporter cassette.

50. The method of paragraph 47, wherein the at least one engineered nucleic acid encodes at least three gRNAs: a first gRNA complementary to a first nuclease recognition site of the target gene of interest; a second gRNA complementary to a second nuclease recognition site of the target gene of interest; and a third gRNA complementary to the nuclease recognition site of the activatable reporter cassette.

51. The method of any one of paragraphs 47-50, wherein the at least one engineered nucleic acid further encodes a nuclease that cleaves the nuclease recognition site of (a) and (b).

52. The method of any one of paragraphs 47-50 further comprising transfecting the cells with an engineered nucleic acid encoding a nuclease that cleaves the nuclease recognition site of (a) and (b).

53. The method of paragraph 51 or 52 further comprising incubating the cells under conditions that result in cleavage of the nuclease recognition site of (a), cleavage of the nuclease recognition site of (b), and reconfiguration of the downstream selectable marker gene from out-of-frame to in-frame with the upstream selectable marker gene.

54. The method of paragraph 53 further comprising selecting cells that express the downstream selectable marker.

55. The method of paragraph 54 further comprising analyzing phenotypes of cells that express the downstream selectable marker.

56. A method of producing cells for a gene modification assay, comprising: transfecting cells that express (a) a target gene of interest that comprises a nuclease recognition site specific to the target gene of interest and (b) a nuclease that cleaves the nuclease recognition site of the target gene of interest and cleaves a nuclease recognition site of an activatable reporter cassette with an engineered nucleic acid construct comprising a deoxyribonucleic acid-binding domain recognition site (DNA-BDRS) and an activatable reporter cassette that comprises a nuclease recognition site flanked by an upstream selectable marker gene and a downstream an out-of-frame selectable marker gene that is different from the upstream selectable marker gene.

57. The method of paragraph 56, wherein the upstream selectable marker gene is promoterless.

58. The method of paragraph 56, wherein the upstream selectable marker gene is operably linked to a promoter.

59. The method of any one of paragraphs 56-58, wherein the cells further express a programmable nuclease that binds to and cleaves the DNA-BDRS.

60. The method of any one of paragraphs 56-58 further comprising transfecting the cells with a nucleic acid encoding a programmable nuclease that binds to and cleaves the DNA-BDRS.

61. The method of paragraph 59 or 60 further comprising incubating the cells under conditions that result in insertion of the activatable reporter cassette into the genome of the cells and expression of the upstream selectable marker gene.

62. The method of paragraph 61 further comprising selecting cells that express the upstream selectable marker gene.

63. The method of paragraph 62 further comprising transfecting cells that express the upstream selectable marker gene with at least one engineered nucleic acid that encodes a guide RNA (gRNA) complementary to the nuclease recognition site of the target gene of interest and a gRNA complementary to the nuclease recognition site of the activatable reporter cassette.

64. The method of paragraph 63, wherein the at least one engineered nucleic acid includes: a first engineered nucleic acid that encodes a gRNA complementary to a nuclease recognition site of a first target gene of interest expressed by the cells and encodes a gRNA complementary to the nuclease recognition site of the activatable reporter cassette; and a second engineered nucleic acid that encodes a gRNA complementary to a nuclease recognition site of a second target gene of interest expressed by the cells and encodes a gRNA complementary to the nuclease recognition site of the activatable reporter cassette.

65. The method of paragraph 63, wherein the at least one engineered nucleic acid includes: a first engineered nucleic acid that encodes a gRNA complementary to a first nuclease recognition site of the target gene of interest and encodes a gRNA complementary to the nuclease recognition site of the activatable reporter cassette; and a second engineered nucleic acid that encodes a gRNA complementary to a second nuclease recognition site of the target gene of interest and encodes a gRNA complementary to the nuclease recognition site of the activatable reporter cassette.

66. The method of paragraph 63, wherein the at least one engineered nucleic acid encodes at least three gRNAs: a first gRNA complementary to a first nuclease recognition site of the target gene of interest; a second gRNA complementary to a second nuclease recognition site of the target gene of interest; and a third gRNA complementary to the nuclease recognition site of the activatable reporter cassette.

67. The method of any one of paragraphs 63-66 further comprising incubating the cells under conditions that result in cleavage of the nuclease recognition site of the target gene of interest, cleavage of the nuclease recognition site of the activatable reporter cassette, and reconfiguration of the downstream selectable marker gene from out-of-frame to in-frame with the upstream selectable marker gene.

68. The method of paragraph 67 further comprising selecting cells that express the downstream selectable marker.

69. The method of paragraph 68 further comprising analyzing phenotypes of cells that express the downstream selectable marker.

70. A method of producing cells for a gene modification assay, comprising: transfecting cells that express a target gene of interest that comprises a nuclease recognition site specific to the target gene of interest with an engineered nucleic acid construct comprising a deoxyribonucleic acid-binding domain recognition site (DNA-BDRS) and an activatable reporter cassette that comprises a nuclease recognition site flanked by an upstream selectable marker gene and a downstream an out-of-frame selectable marker gene that is different from the upstream selectable marker gene.

71. The method of paragraph 70, wherein the upstream selectable marker gene is promoterless.

72. The method of paragraph 70, wherein the upstream selectable marker gene is operably linked to a first promoter.

73. The method of any one of paragraphs 70-72, wherein the cells further express a programmable nuclease that binds to and cleaves the DNA-BDRS.

74. The method of any one of paragraphs 70-72 further comprising transfecting the cells with a nucleic acid encoding a programmable nuclease that binds to and cleaves the DNA-BDRS.

75. The method of paragraph 73 or 74 further comprising incubating the cells under conditions that result in insertion of the activatable reporter cassette into the genome of the cells and expression of the upstream selectable marker gene.

76. The method of paragraph 75 further comprising selecting cells that express the upstream selectable marker gene.

77. The method of paragraph 76 further comprising transfecting cells that express the upstream selectable marker gene with at least one engineered nucleic acid that encodes a guide RNA (gRNA) complementary to the nuclease recognition site of the target gene of interest and a gRNA complementary to the nuclease recognition site of the activatable reporter cassette.

78. The method of paragraph 77, wherein the at least one engineered nucleic acid includes: a first engineered nucleic acid that encodes a gRNA complementary to a nuclease recognition site of a first target gene of interest expressed by the cells and encodes a gRNA complementary to the nuclease recognition site of the activatable reporter cassette; and a second engineered nucleic acid that encodes a gRNA complementary to a nuclease recognition site of a second target gene of interest expressed by the cells and encodes a gRNA complementary to the nuclease recognition site of the activatable reporter cassette.

79. The method of paragraph 77, wherein the at least one engineered nucleic acid includes: a first engineered nucleic acid that encodes a gRNA complementary to a first nuclease recognition site of the target gene of interest and encodes a gRNA complementary to the nuclease recognition site of the activatable reporter cassette; and a second engineered nucleic acid that encodes a gRNA complementary to a second nuclease recognition site of the target gene of interest and encodes a gRNA complementary to the nuclease recognition site of the activatable reporter cassette.

80. The method of paragraph 79, wherein the at least one engineered nucleic acid encodes at least three gRNAs: a first gRNA complementary to a first nuclease recognition site of the target gene of interest; a second gRNA complementary to a second nuclease recognition site of the target gene of interest; and a third gRNA complementary to the nuclease recognition site of the activatable reporter cassette.

81. The method of any one of paragraphs 77-80, wherein the at least one engineered nucleic acid that encodes the gRNAs further encodes a nuclease that cleaves the nuclease recognition site of the target gene of interest and cleaves the nuclease recognition site of the activatable reporter cassette.

82. The method of any one of paragraphs 70-81 wherein the engineered nucleic acid construct that encodes the DNA-BDRS and the activatable reporter construct further encodes a nuclease that cleaves the nuclease recognition site of the target gene of interest and cleaves the nuclease recognition site of the activatable reporter cassette.

83. The method of paragraph 82, wherein the upstream selectable marker gene of the activatable reporter construct is operably linked to a first promoter and the nuclease is encoded by a gene operably linked to a second promoter that is different from the first promoter.

84. The method of paragraph 81 or 82 further comprising incubating the cells under conditions that result in cleavage of the nuclease recognition site of the target gene of interest, cleavage of the nuclease recognition site of the activatable reporter cassette, and reconfiguration of the downstream selectable marker gene from out-of-frame to in-frame with the upstream selectable marker gene.

85. The method of paragraph 84 further comprising selecting cells that express the downstream selectable marker.

86. The method of paragraph 85 further comprising analyzing phenotypes of cells that express the downstream selectable marker.

87. A method, comprising (a) introducing reagents into cells of a mixed population that comprise (i) a target gene of interest that comprises at least one nuclease recognition site and (ii) at least one activatable reporter cassette that comprises a nuclease recognition site flanked by an upstream selectable marker gene and a downstream out-of-frame selectable marker gene that is different from the upstream selectable marker gene, wherein the reagents comprise a nuclease that cleaves the at least one nuclease recognition site, a guide RNA (gRNA) complementary to the nuclease recognition site of the activatable reporter cassette and a gRNA complementary to the nuclease recognition site of a target gene of interest, thereby producing cells that comprise the reagents; (b) incubating the cells of (a) that comprise the reagents under conditions that result in expression of the upstream selectable marker gene and cleavage of the at least one nuclease recognition site, thereby producing cells that express the upstream selectable marker gene; and (c) contacting cells of (b) that express the upstream selectable marker gene with a selection agent associated with the downstream selectable marker gene, under conditions that result in death of cells that do not express the downstream selectable marker gene, thereby producing cells that express the downstream selectable marker gene.

88. A method, comprising (a) introducing reagents into cells of a mixed population that comprise (i) a target gene of interest that comprises at least one nuclease recognition site, (ii) at least one activatable reporter cassette that comprises a nuclease recognition site flanked by an upstream selectable marker gene and a downstream out-of-frame selectable marker gene that is different from the upstream selectable marker gene, and (iii) a nuclease that cleaves the at least one nuclease recognition site, wherein the reagents comprise a guide RNA (gRNA) complementary to the nuclease recognition site of the activatable reporter cassette and a gRNA complementary to the nuclease recognition site of a target gene of interest, thereby producing cells that comprise the reagents; and (b) incubating the cells of (a) that comprise the reagents under conditions that result in expression of the upstream selectable marker gene and cleavage of the at least one nuclease recognition site, thereby producing cells that express the upstream selectable marker gene; and (c) contacting cells of (b) that express the upstream selectable marker gene with a selection agent associated with the downstream selectable marker gene, under conditions that result in death of cells that do not express the downstream selectable marker gene, thereby producing cells that express the downstream selectable marker gene.

89. The method of paragraph 87 or 88, further comprising analyzing cells produced in (c) that express the downstream selectable marker gene.

EXAMPLES

Example 1

Results of the studies provided herein show efficient generation of cell lines containing a Cas9 encoding transgene in the AAVS1 locus together with an activatable reporter cassette.

Results of the studies provided herein also show that rpsL-BSD counter selection may be used for efficient preparation of plasmid-based guide RNA libraries. Initially, experiments tested whether transformants could be used directly for liquid culture containing kanamycin and streptomycin, thus omitting laborious steps of plating and colony pickup. The isolated plasmids from cultures inoculated with either single colony or transformation products were compared. This comparison was performed for 96 guide RNAs targeting bromodomain-containing genes using Sanger sequencing methods and a Fragment Analyzer™ to control quality and quantity of correctly ligated oligonucleotide dimers into pU6 plasmids, respectively. Results demonstrated that this method can be used in high-throughput manner and substantially reduces the efforts required for plasmid library preparation.

Example 2

FIG. 23A shows a GFP-positive cell (shaded gray) having a particular barcode represented by an activatable reporter cassette containing an NRS1 recognition site. This barcode is specific to this cell, thus blasticidin resistance can be obtained only in this cell upon transfection with Cas9 and a gRNA targeting NRS1. Blasticidin selection (after transfection with a particular guide RNA) will isolate the specific cell associated with the specific barcode. In some embodiments, all cells on a dish (Petri dish) may be isolated, each containing a barcode specific to that cell. In some embodiments, at least $10^{12}$ different barcodes may be used.

Example protocol for barcoding:

(1) Day 0—transfect a mixed population of cells containing barcodes (activatable reporter cassettes) with Cas9 and a gRNA;

(2) Day 3—add selection agent (e.g., blasticidin) and analyze cell growth (3) Day 14—analyze GFP expression in residual cells resistance to selection agent.

Example 3

CRISPR screens represent a promising approach to identify genes suitable for therapeutic targeting. A growing number of studies successfully utilized CRISPR technology for performing genetic screens in either pooled or arrayed formats, most commonly through lentiviral delivery of guide RNA libraries. Practical disadvantages of lentivirus libraries, however, including cost, labor expensive production, non-renewable stocks for end users, requirement of Biosafety Level 2 facilities, and virus-compatible automation infrastructure are limiting applications of virus-based guide RNA libraries. Moreover, the random integration nature of viral DNA can potentially interfere with some phenotypic analysis. In addition, long-term exposure to Cas9 and guide RNA expression provided by lentiviruses may result in deleterious effects.

Alternatively, transfection of plasmid libraries can be used to deliver guide RNAs. Transfection efficiency with nucleic acids, however, is sub-optimal in many cell types. This is particularly relevant for negative selection screens where a potential small proportion of un-transfected cells will have a growth advantage, thus masking the readout and compromising the outcome.

Figure 24:
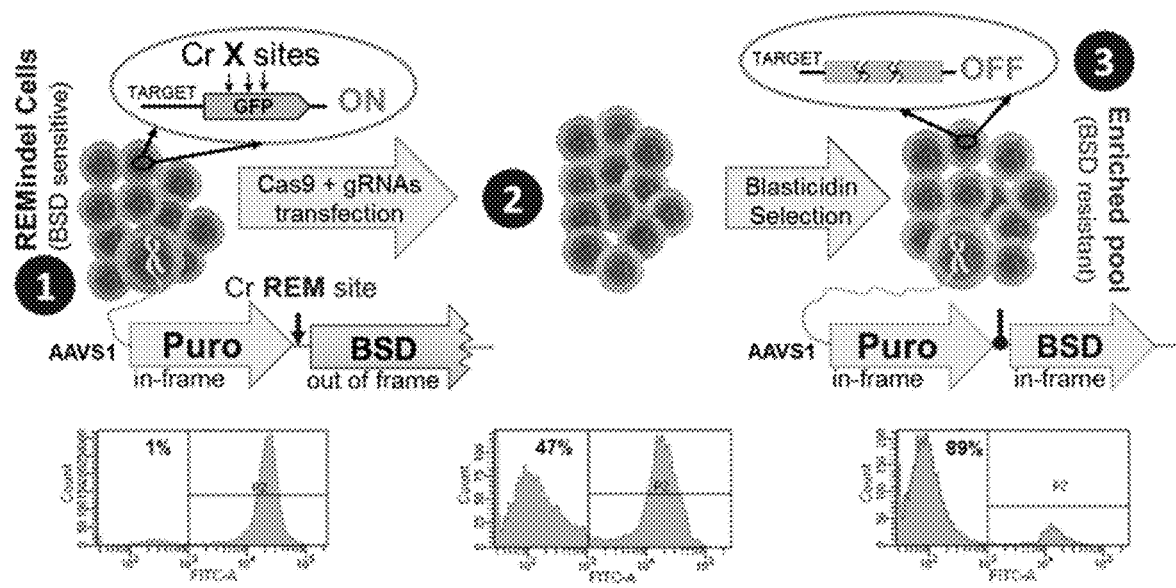
FIG. 24 shows a schematic of an example of a REMindel experiment. (1) In cells constitutively expressing EGFP, the REMindel cassette was knocked-in using FuGeneHD reagents. Cas9 and the gRNAs targeted the REM site, which is an artificial target site without off-targets in the human genome. (2) The arrayed CRISPR library was then applied (more than one gRNA for Gene X may be used). The gRNA(s) may be delivered via plasmid, IVT, PCT or synthetic crRNA. (3) Activated BSD was then selected and the phenotype studied. Three days after transfection, cells were passaged in two wells, one of which was kept under Blasticidin selection. After one week, the portion of EGFP positive cells was measured using FACS. Results indicated that the EGFP-disrupted cells were enriched following Blasticidin selection.

The methodology of the present disclosure (REMindel) may be used, in some embodiments, to efficiently enrich for targeted cells and facilitate screening of guide RNA libraries in vector-based arrayed format. A REMindel cassette may be precisely integrated in a safe harbor locus (AAVS1) of the target cell. A REMindel cassette includes two antibiotic selections in tandem: the first (e.g., puromycin) allows selection of cells with correct cassette integration, while the second is an out-of-frame (downstream of REM site, e.g., FIG. 24) non-functional marker (e.g., blasticidin) that is reconstituted by DNA repair upon CRISPR cut in the REM site (FIG. 24). Transfecting REMindel cells with CRISPR targeting both the gene of interest (GFP, FIG. 24) and the REM site simultaneously activated blasticidin and created a knockout (KO) in the gene of interest. Blasticidin selection enabled enrichment of KO cells (FIG. 24). Therefore, cells "remind" exposure to Cas9 with a permanent activation of a selection marker.

Example 4

Cas9 nuclease combined with large-scale guide RNA (gRNA) libraries have emerged as an exciting new tool for forward genetic screens. In arrayed strategies for genetic screens in cultured cells, gRNAs are arranged in multi-well plates to be delivered by either transfection or viral transduction. Each gRNA has to be separately prepared, so cost-efficient methodologies are in high demand for preparing large-scale arrayed resources.

Figure 25A:
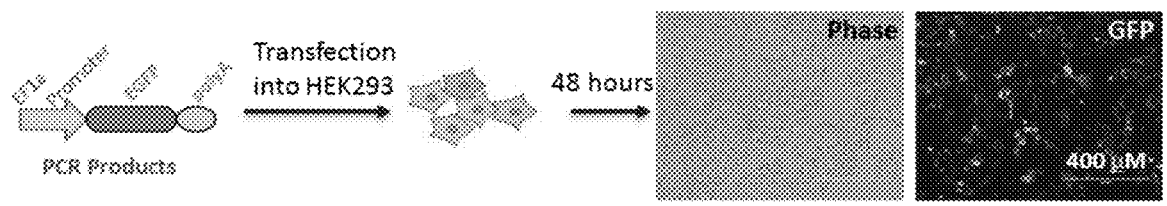
FIG. 25A shows a schematic and results from an experiment in which a PCR-amplified cassette containing EGFP under the control of EF1a promoter resulted in the expression of EGFP in HEK293 cells. EGFP was measured 48 hours after transfection.
Figure 25B:
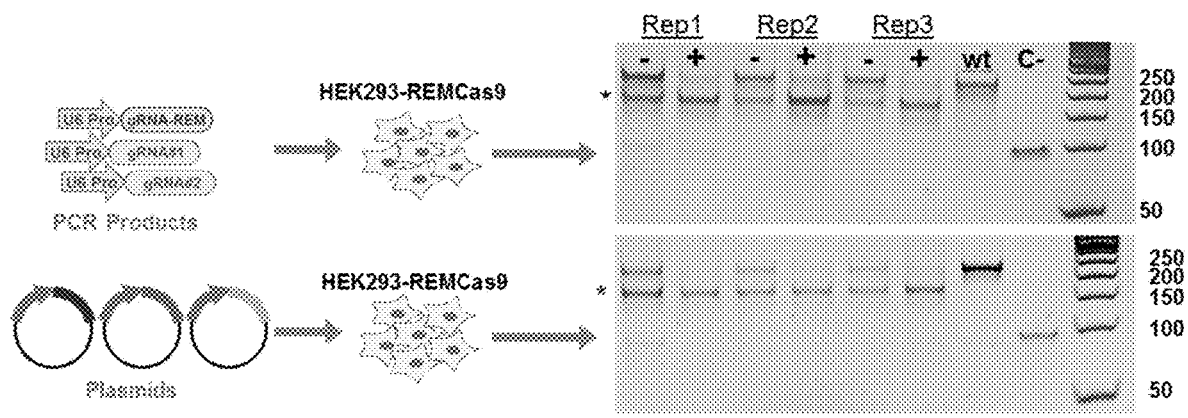
FIG. 25B shows a comparison of PCR-based gRNAs versus plasmid-based gRNAs. Three gRNAs (including gRNA-REM and dual gRNAs, #1 and #2, targeting AAVS1 locus) were co-transfected into HEK293-REM cells that constitutively express Cas9. The frequency of mutated allele (*) is indicated for three replicates (Rep1, Rep2 and Rep3) with (+) and without (−) REMindel enrichment. Results indicate the enrichment of mutated cells in both PCR-based and plasmid-based experiments.

This Example shows that a GFP cassette in PCR product format can be efficiently transfected into human cells resulting in detectable expression (FIG. 25). An overlap-extension design of oligonucleotides for a PCR method may be used to amplify any cassette containing U6 promoter, for example, together with a gRNA backbone (FIG. 26A). The PCR products induce gene knock out in HEK293 cells stably expressing Cas9 (FIG. 26B). PCR-gRNAs may be used to generate cost effective gRNA libraries. Moreover, overlap-extension oligonucleotides may also be used for ligation-free cloning of gRNAs (FIG. 27A). This was validated by showing that 9 out of 11 gRNAs were correctly assembled into the vector using PCR products generated using overlap extension (FIG. 27B).

This method for preparing gRNAs is particularly useful, for example, when used on a larger scale with the virus-free arrayed screening strategy (REMindel), as provided herein.

Example 5

The Cas9 DNA cleaving system has emerged as an efficient and simple method for gene targeting. Here, REMindel-based enrichment of genome edited human cells was examined using single and dual guide RNAs (gRNA) targeting different loci in the human genome.

Figure 28A:
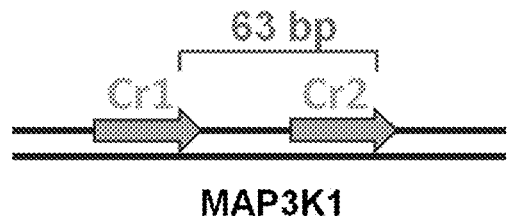
FIGS. 28A-28B show a schematic of the experiment discussed in Example 5.
Figure 28B:
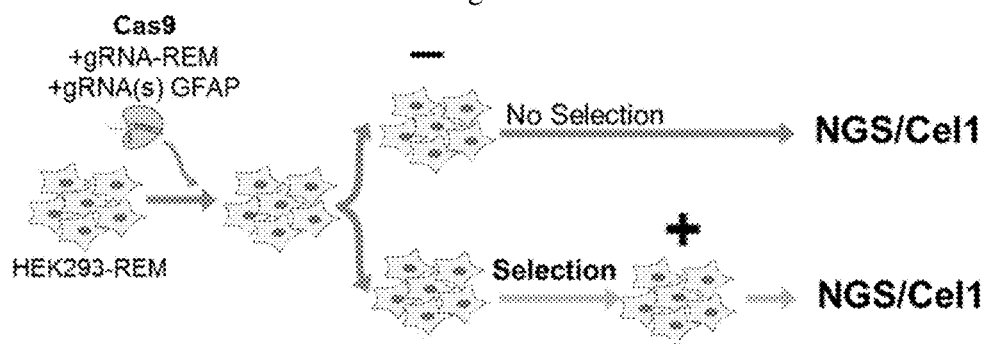

Two or more gRNAs against targeted genes (FIG. 28A) were prepared in plasmid format and transfected into HEK293-REM cells separately or together with a REMindel gRNA and Cas9 encoding plasmids. Indel frequencies were measured before and after selection with Cell assay and amplicon next generation sequencing (FIG. 28B).

Figure 29A:
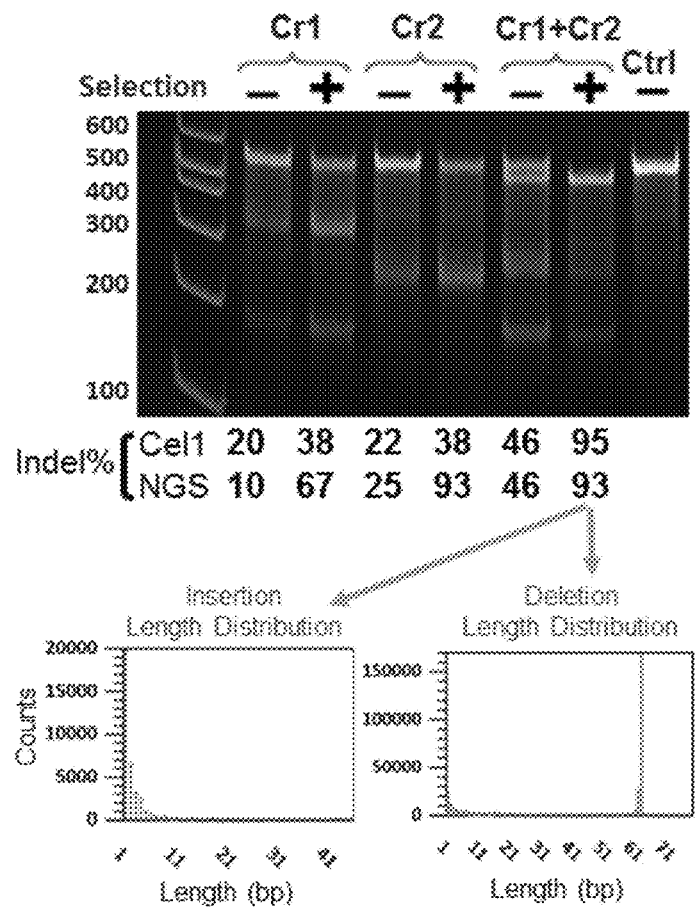
FIG. 29A, top panel, is a photograph of a gel showing that higher indel frequencies can be achieved using two gRNAs targeting the gene of interest.
Figure 29B:
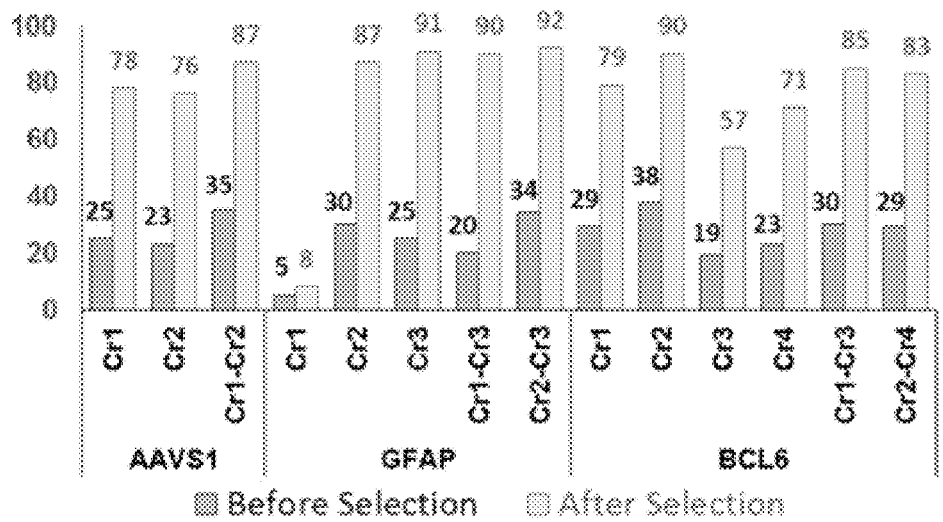
FIG. 29 B is a graph showing that applying dual-gRNA and REMindel can result in more than 80% indel frequency at different loci in enriched cell population.
FIG. 29C is a graph showing results from amplicon sequencing, which provides insight regarding output of DNA repair machinery on the targeted locus.
Figure 29C:
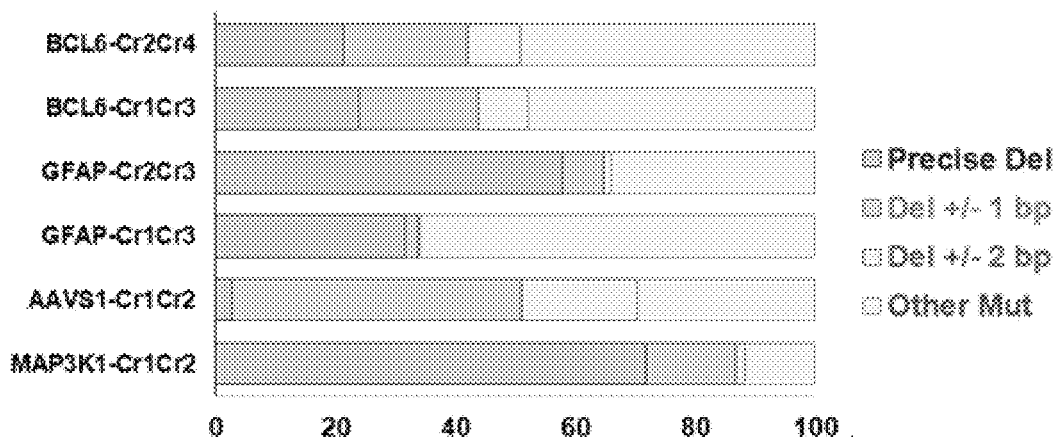

Higher indel frequencies were achieved using two gRNAs targeting the gene of interest (FIG. 29A, top panel). NGS analysis was successfully performed on samples containing large indels induced by dual-gRNAs (FIG. 29B, bottom panel). Applying dual-gRNA and REMindel resulted in more than 80% indel frequency at different loci in enriched cell population (FIG. 29B). This can be translated as higher chance of knockout and thus increasing the success rate in phenotypic screens using the CRISPR system. Amplicon sequencing, in addition to providing more consistent results for measuring indel frequencies comparing to Cell assay, also provides insight regarding the output of DNA repair machinery on the targeted locus (FIG. 29C). In summary, these data indicate that REMindel is highly efficient for enrichment of cells containing Cas9 nuclease-induced mutations.

Example 6

Negative selection screens are used for therapeutic target discovery to identify essential gene sets associated to fundamental processes in different cell types. As provided herein, 'REMindel' may be used as a virus-free methodology towards CRISPR/Cas9-based knockout screens. REMindel enables implementation of plasmid format guide RNA (gRNA) libraries via transfection, thus alleviating cost and effort required for preparing of libraries as viral particles. Here, the efficacy of the REMindel approach was examined with a focus on negative selections under different experimental conditions.

Figure 30:
FIG. 30 shows a schematic of three gRNAs designed against Alu element, which has a very high abundance throughout human genome.

The gRNAs were designed against the Alu element, which has a high abundance throughout human genome (FIG. 30). Expression of Cas9 together with these gRNAs was expected to induce high number of double-strand breaks in the genome and trigger cell death. These three gRNAs were tested separately, in comparison with a gRNA targeting a non-essential gene (AAVS1) in HEK293 cells with (in the presence of a REMindel cassette) and without (in the absence of a REMindel cassette) REMindel selection. The experiment was also performed under three different transfection efficiency settings (as measured by GFP expression 48 hours after transfection) with two different starting confluency of seeded cells. INCUCYTE® was used to determine the transfection efficiency and measurements of confluency (FIG. 31).

The results showed that without using REMindel, untransfected cells have a growth advantage over transfected cells and mask the lethality readout. REMindel enabled the elimination of the untransfected cells and successfully detected the lethality effects of Alu gRNAs. Arrayed-format screens are commonly conducted in micro-well plates. Thus, the starting cell population should be as low as possible to avoid over-confluency of cells during the time course of the experiment. Remarkably, the expected experimental success was achieved with low starting cell density using only REMindel (FIG. 31). These results show that use of REMindel increases the accuracy and efficacy of arrayed-format screens for essential genes.

Example 7

One step in performing successful arrayed-format gene targeting using CRISPR system is to ensure the efficient delivery of Cas9 and guide-RNAs (gRNAs) into the cells. Although gRNA delivery through viral transduction can provide efficient expression in transduced cells, long term genomic exposure to Cas9 and gRNA provided by integrated viruses can result in off-target effects, thus compromising the experimental readout. Alternatively, transient expression of gRNA via transfection of plasmids can also be used. However, in general, plasmid transfection is not as efficient procedure as viral transduction and this variability (specially related to CRISPR reagents) could potentially affect the overall outcome of the experiments since the sub-population of cells with acquired phenotype depends on transfection efficiency. 'REMindel' may be used as a transfection-based methodology for enhancing knockout applications of the CRISPR system. In this Example, REMindel outcome with different transfection efficiencies was tested.

Figure 32A:
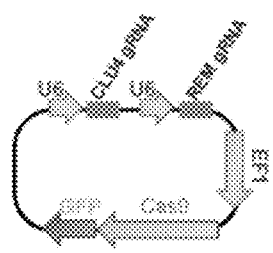
FIG. 32A shows a schematic of a plasmid containing Cas9GFP together with two gRNAs in tandem.
Figure 32B:
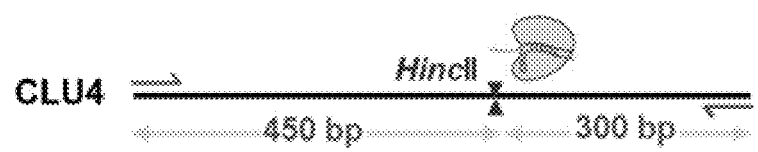
FIG. 32B shows a schematic of CLU4-gRNA precisely targeting a restriction enzyme site in CLU4 gene.
Figure 32C:
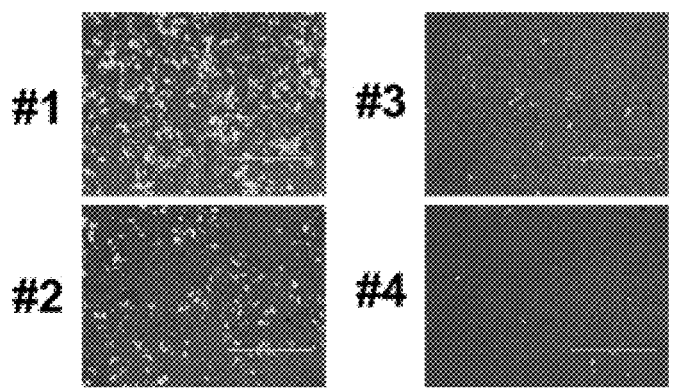
FIG. 32C shows results from scaling down the amount of transfection reagent to transfect gRNAs-Cas9 plasmid into a fixed amount of cells.

A plasmid containing Cas9-GFP together with two gRNAs in tandem was first generated (FIG. 32A). CLU4-gRNA precisely targets a restriction enzyme site in the CLU4 gene. The site will be disrupted upon successful targeting, thus allowing the quantification of efficiency by digestion and fragment analysis (FIG. 32B). To obtain different transfection efficiency, the amount of transfection reagent used to transfect gRNAs-Cas9 plasmid into a fixed amount of cells was scaled down in a stepwise manner (FIG. 32C). Following transfection, the cells were divided into two groups (to select or not with REMindel). Finally, the targeting efficiency was measured using a fragment analyzer.

Figure 32D:
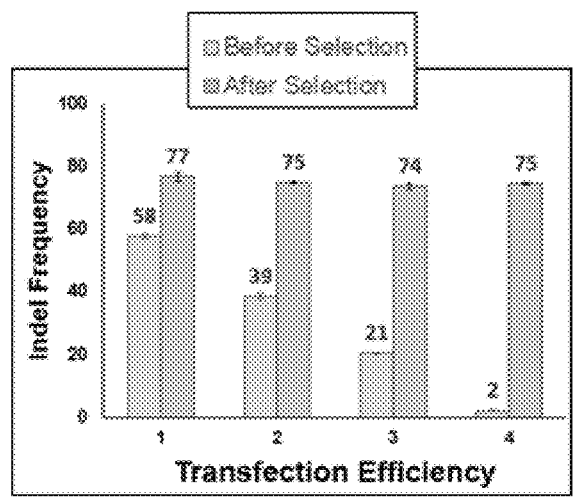
FIG. 32D is a graph showing that the same frequency of indel was detected across all differently transfected samples following REMindel enrichment.

Results showed that increased transfection efficiency is directly correlated to increased indel frequency. Nevertheless, following REMindel enrichment, the same frequency of indel was detected across all differently transfected samples (FIG. 32D). These data prove that REMindel selection enables the same level of indel enrichment regardless of transfection efficiency.

Example 8

The CRISPR-Cas9 system has emerged as an efficient tool for creating mutations on selected gene and generating knockout cells. However, if the mutations do not cause a frameshift, the targeted gene can still be transcribed to produced a functional protein. Moreover, the ploidy of the recipient cell line greatly affects the mutation outcome. In case of KO in diploid cells, both alleles, preferably in a gene region affecting all transcript variants, need to have the proper frameshift. As provided herein, 'REMindel' is a methodology for enriching mutated cells. In this Example, REMindel was used to generate and enrich knockout phenotypes.

Figure 33A:
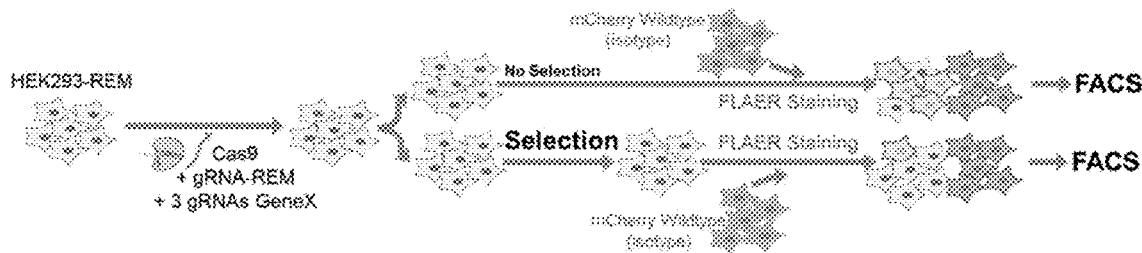
FIG. 33A is a schematic showing Cas9 and gRNAs against REM site and PIG genes (which are involved in GPI anchor biosynthesis pathway) transfected into HEK293-REM cells in plasmid format using a lipid-based (Fu-GeneHD transfection reagents) transfection protocol. After three days cells were passaged into two, and one was kept under Blasticidin selection for one week. Before FLAER staining, mCherry positive cells having a wild-type genotype for PIG genes (isotype) were mixed with the HEK-REM cells. The percentage of mCherry and FLAER-positive cells was measured using FACS.

Seven genes (PIG) essential for glycosylphosphatidylinositol (GPI anchor) biosynthesis were targeted and a sensitive FACS readout (FLAER assay) was used. PIG genes were targeted in arrayed format in HEK293-REMindel cells (mainly triploid) and the percentage of cells was compared with knockout phenotype with or without REMindel selection. All gRNAs were transfected in plasmid format using lipid-based transfection protocol (FIG. 33A).

Figure 33B:
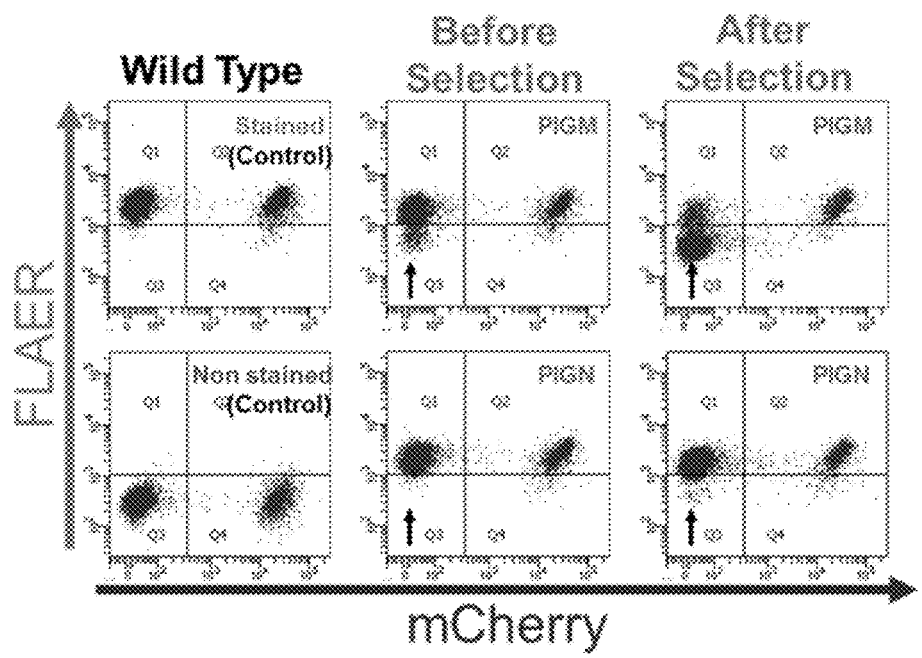
FIG. 33B shows results from a FACS analysis using a FLAER (fluorescein-labeled proaerolysin) assay. HEK293-REM cells with wildtype phenotype are gated in Q1 after FLAER staining. Cells with disrupted GPI (for two genes, PIGM and PIGN, before and after selection) are gated in Q3.
Figure 33C:
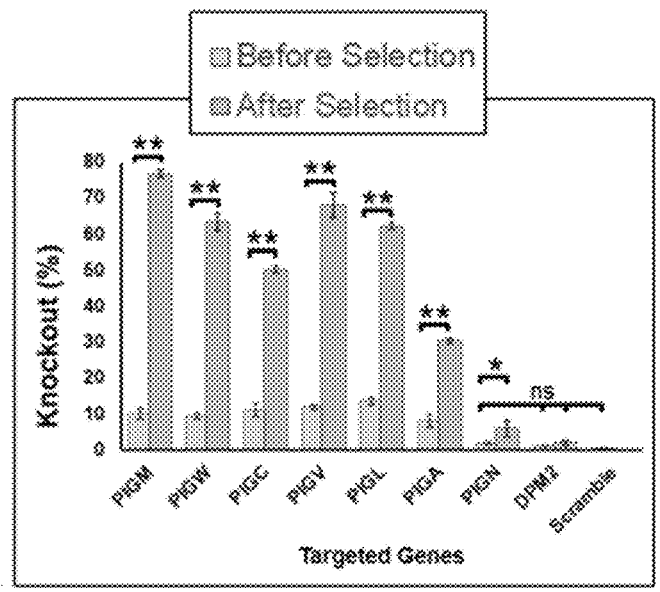
FIG. 33C is a graph showing that REMindel enriched the population of "truly" knockout cells. Results for 7 PIG genes (essential for the GPI anchor biosynthesis) and DPM2 (non-essential for GPI anchor biosynthesis) are shown in the bar graph. ns; non-significant (p-value >0.05), *; statistically significant (p-value <0.05).

FACS analysis (FIG. 33B) using a FLAER assay provided highly sensitive detection of GPI knockout HEK293 cells. REMindel remarkably enriched the population of "truly" knockout cells, and in one case (PIGN), detection of KO phenotype would not have been possible without REMindel (FIG. 33C). This study confirms that REMindel is an efficient methodology towards enrichment of knockout cells.

Example 9

Figure 34:
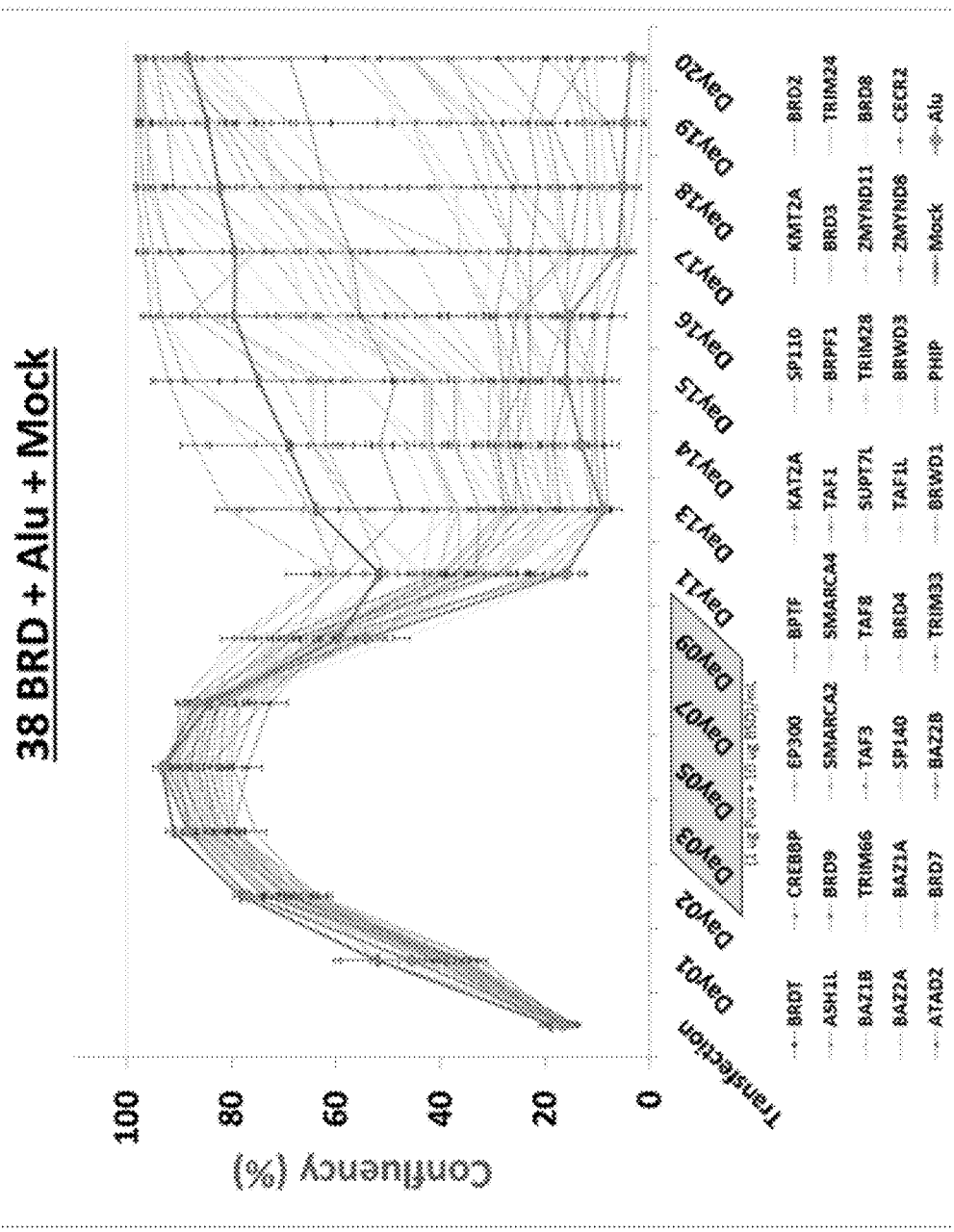
FIG. 34 shows results from a lethality screen of 38 bromodomain containing genes.
Figure 35:
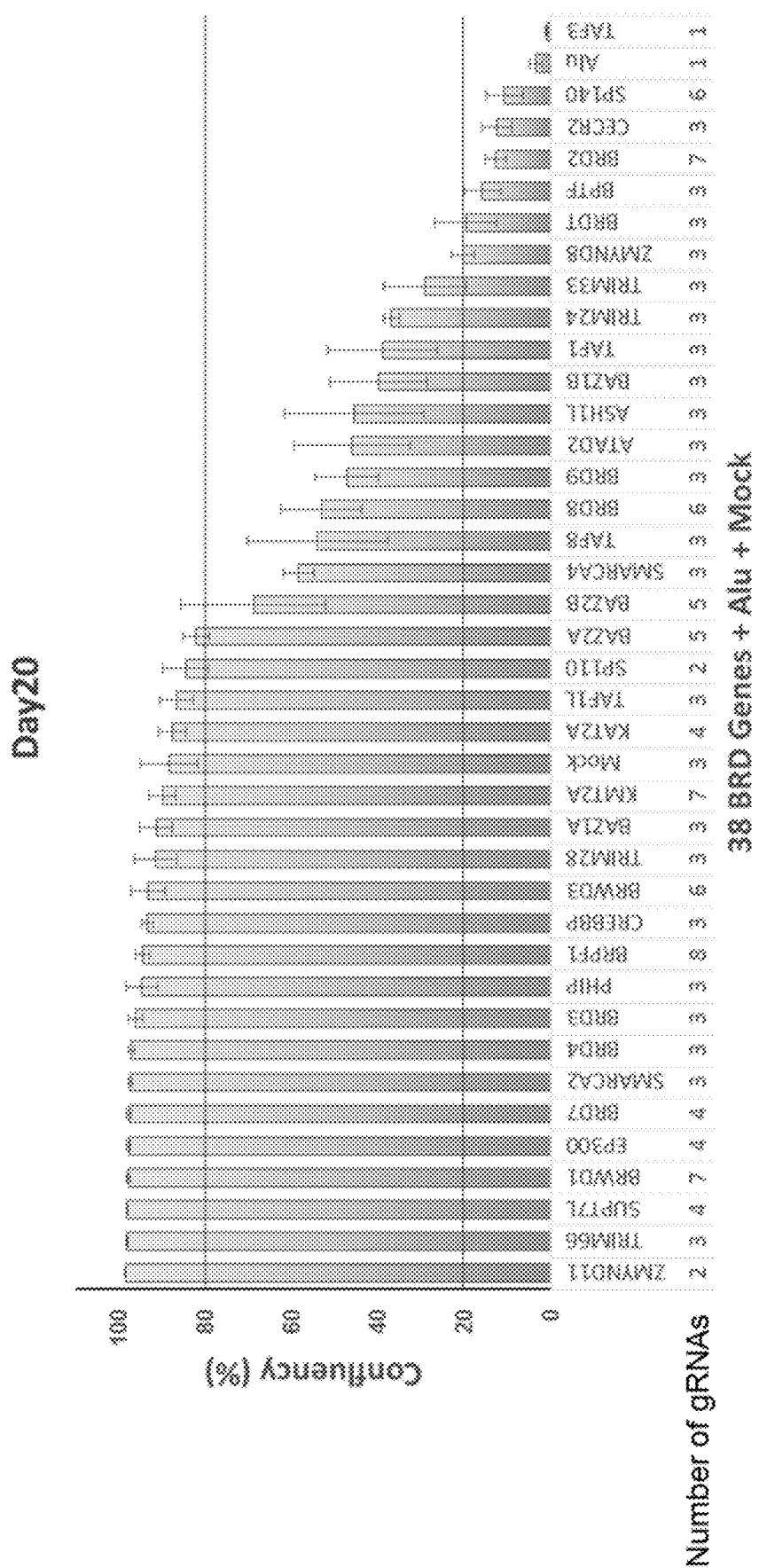
FIG. 35 shows confluency endpoint measurements and the number of gRNAs targeting each of the 38 bromodomain containing genes

A lethality screen for 38 bromodomain containing genes in arrayed format in HCT116-REM cells was performed. Confluency was measured during three weeks on a daily basis. Alu gRNA and AAVS1 were used as lethal and non-lethal controls, respectively. Plasmids containing Cas9 and gRNAs were transfected into HCT116 cells using FuGeneHD transfection reagents. Selection for one week (1 µg/mL Puromycin and 10 µg/mL blasticidin) was applied during Day 3 until Day 9. Cells were cultured in 96-well format plates and the media changed daily. Results are shown in FIG. 34. FIG. 35 shows confluency endpoint measurements and the number of gRNAs targeting each gene.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An engineered nucleic acid construct comprising a deoxyribonucleic acid-binding domain recognition site (DNA-BDRS) and an activatable reporter cassette that comprises a Cas9 or Cpf1 RNA-guided nuclease recognition site flanked by an upstream promoterless selectable marker gene and a downstream out-of-frame selectable marker gene that is different from the upstream selectable marker gene, wherein the DNA-BDRS is capable of facilitating direct, site-specific ligation of the construct into a locus of a genome.

2. The engineered nucleic acid construct of claim 1, further comprising a nucleic acid sequence encoding a Cas9 or Cpf1 RNA-guided nuclease.

3. The engineered nucleic acid construct of claim 1, wherein the Cas9 or Cpf1 RNA-guided nuclease recognition site is a Cas9 RNA-guided nuclease recognition site.

4. An isolated cell comprising (a) a target gene of interest that comprises at least one Cas9 or Cpf1 RNA-guided nuclease recognition site, (b) the engineered nucleic acid construct of claim 1, wherein the Cas9 or Cpf1 RNA-guided nuclease recognition site of the activatable reporter cassette comprises a sequence that is different from the Cas9 or Cpf1 RNA-guided nuclease recognition site of the target gene of interest, and (c) a programmable nuclease that is capable of binding to the DNA-BDRS.

5. The isolated cell of claim 4, wherein the programmable nuclease is a zinc finger nuclease, a transcription activator-like effector nuclease or a Cas9-FokI nuclease.

6. The isolated cell of claim 4, further comprising a Cas9 or Cpf1 RNA-guided nuclease that is capable of cleaving the Cas9 or Cpf1 RNA-guided nuclease recognition site of the activatable reporter cassette and the Cas9 or Cpf1 RNA-guided nuclease recognition site of the target gene of interest.

7. The isolated cell of claim 4, further comprising a first guide RNA (gRNA) complementary to the Cas9 or Cpf1 RNA-guided nuclease recognition site of the target gene of interest and a second gRNA complementary to the Cas9 or Cpf1 RNA-guided nuclease recognition site of the activatable reporter cassette.

8. The isolated cell of claim 7, wherein the first gRNA complementary to the Cas9 or Cpf1 RNA-guided nuclease recognition site of the target gene of interest and the second gRNA complementary to the Cas9 or Cpf1 RNA-guided nuclease recognition site of the activatable reporter cassette are encoded by engineered nucleic acids located on the same construct.

9. The isolated cell of claim 7, wherein the construct further comprises a nucleic acid encoding the Cas9 or Cpf1 RNA-guided nuclease.

10. The isolated cell of claim 4, comprising multiple gRNAs, each complementary to a different Cas9 or Cpf1 RNA-guided nuclease recognition site of the target gene of interest.

11. The isolated cell of claim 4, wherein the cell is a mammalian cell.

12. The isolated cell of claim 4, wherein the cell is an induced pluripotent stem cell.

13. The isolated cell of claim 4, wherein the Cas9 or Cpf1 RNA-guided nuclease recognition site is a Cas9 RNA-guided nuclease recognition site.

14. A population of isolated cells comprising the cells of claim 4.

15. A culture comprising cell media and the population of isolated cells of claim 14.

16. An isolated cell comprising:
(a) a target gene of interest that comprises a Cas9 or Cpf1 RNA-guided nuclease recognition site specific to the target gene of interest;
(b) an activatable reporter cassette integrated into a genome of the cell, the activatable reporter cassette comprising a Cas9 or Cpf1 RNA-guided nuclease recognition site flanked by an upstream promoterless selectable marker gene and a downstream out-of-frame selectable marker gene that is different from the upstream selectable marker gene, wherein the RNA-guided nuclease recognition site of the activatable reporter cassette has a sequence that is different from the sequence of the Cas9 or Cpf1 RNA-guided nuclease recognition site specific to the target gene of interest;
(c) a Cas9 or Cpf1 RNA-guided nuclease that is capable of cleaving the Cas9 or Cpf1 RNA-guided nuclease recognition site of the activatable reporter cassette and the Cas9 or Cpf1 RNA-guided nuclease recognition site of the target gene of interest; and
(d) a first guide RNA (gRNA) complementary to the Cas9 or Cpf1 RNA-guided nuclease recognition site of the target gene of interest and a second complementary to the Cas9 or Cpf1 RNA-guided nuclease recognition site of the activatable reporter cassette.

17. A method of producing cells for a gene modification assay, comprising:
  transfecting cells that comprise (a) a target gene of interest that comprises a Cas9 or Cpf1 RNA-guided nuclease recognition site specific to the target gene of interest, (b) an activatable reporter cassette integrated into a genome of the cell that comprises a Cas9 or Cpf1 RNA-guided nuclease recognition site flanked by an upstream promoterless selectable marker gene and a downstream out-of-frame selectable marker gene that is different from the upstream selectable marker gene, wherein the Cas9 or Cpf1 RNA-guided nuclease recognition site of the activatable reporter cassette has a sequence that is different from the sequence of the Cas9 or Cpf1 RNA-guided nuclease recognition site specific to the target gene of interest, and (c) a Cas9 or Cpf1 RNA-guided nuclease that is capable of cleaving the Cas9 or Cpf1 RNA-guided nuclease recognition site of (a) and (b)
  with at least one engineered nucleic acid comprising a first nucleotide sequence that encodes a first guide RNA (gRNA) complementary to the Cas9 or Cpf1 RNA-guided nuclease recognition site of (a) and a second nucleotide sequence that encodes a second gRNA complementary to the Cas9 or Cpf1 RNA-guided nuclease recognition site of (b), thereby producing cells for a gene modification assay.

18. The method of claim 17, wherein the at least one engineered nucleic acid further comprises:
  a third nucleotide sequence that encodes a third gRNA complementary to a Cas9 or Cpf1 RNA-guided nuclease recognition site of a second target gene of interest expressed by the cells.

19. A method of producing cells for a gene modification assay, comprising:
  (a) transfecting a first population of cells that comprise (i) a first target gene of interest that comprises a Cas9 or Cpf1 RNA-guided nuclease recognition site specific to the first target gene of interest, (ii) an activatable reporter cassette integrated into a genome of the cell that comprises a Cas9 or Cpf1 RNA-guided nuclease recognition site flanked by an upstream promoterless selectable marker gene and a downstream out-of-frame selectable marker gene that is different from the upstream selectable marker gene, wherein the Cas9 or Cpf1 RNA-guided nuclease recognition site of the activatable reporter cassette has a sequence that is different from the sequence of the nuclease recognition site specific to the target gene of interest, and (iii) a Cas9 or Cpf1 RNA-guided nuclease that cleaves the Cas9 or Cpf1 RNA-guided nuclease recognition site of (a)(i) and the Cas9 or Cpf1 RNA-guided nuclease recognition site of (a)(ii) with at least one engineered nucleic acid that encodes a first guide RNA (gRNA) complementary to the Cas9 or Cpf1 RNA-guided nuclease recognition site of (a)(i) and a second gRNA complementary to the Cas9 or Cpf1 RNA-guided nuclease recognition site of (a)(ii); and
  (b) transfecting a second population of cells that comprise (i) a second target gene of interest that comprises a Cas9 or Cpf1 RNA-guided nuclease recognition site specific to the second target gene or interest, (ii) an activatable reporter cassette that comprises a Cas9 or Cpf1 RNA-guided nuclease recognition site flanked by an upstream promoterless selectable marker gene and a downstream out-of-frame selectable marker gene that is different from the upstream selectable marker gene, wherein the Cas9 or Cpf1 RNA-guided nuclease recognition site of the activatable reporter cassette has a sequence that is different from a sequence of the Cas9 or Cpf1 RNA-guided nuclease recognition site specific to the second target gene of interest, and (iii) a Cas9 or Cpf1 RNA-guided nuclease that cleaves the Cas9 or Cpf1 RNA-guided nuclease recognition site of (b)(i) and the Cas9 or Cpf1 RNA-guided nuclease recognition site of (b)(ii) with at least one engineered nucleic acid that encodes a third guide RNA (gRNA) complementary to the Cas9 or Cpf1 RNA-guided nuclease recognition site of (b)(i) and a fourth gRNA complementary to the Cas9 or Cpf1 RNA-guided nuclease recognition site of (b)(ii), thereby producing cells for a gene modification assay.

20. A method, comprising:
  (a) introducing reagents into cells of a mixed population of cells that each comprise (i) a target gene of interest that comprises at least one Cas9 or Cpf1 RNA-guided nuclease recognition site specific to the target gene of interest and (ii) at least one activatable reporter cassette that comprises a Cas9 or Cpf1 RNA-guided nuclease recognition site flanked by an upstream promoterless selectable marker gene and a downstream out-of-frame selectable marker gene that is different from the upstream selectable marker gene, wherein the Cas9 or Cpf1 RNA-guided nuclease recognition site of the activatable reporter cassette has a sequence that is different from the sequence of the Cas9 or Cpf1 RNA-guided nuclease recognition site specific to the target gene of interest, wherein the reagents comprise a Cas9 or Cpf1 RNA-guided nuclease that is capable of cleaving the Cas9 or Cpf1 RNA-guided nuclease recognition sites of the target gene of interest and the activatable reporter cassette, a first guide RNA (gRNA) complementary to the Cas9 or Cpf1 RNA-guided nuclease recognition site of a target gene of interest and a second guide RNA gRNA complementary to the Cas9 or Cpf1 RNA-guided nuclease recognition site of the activatable reporter cassette, thereby producing cells that comprise the reagents;
  (b) incubating the cells of (a) that comprise the reagents under conditions that result in expression of the upstream selectable marker gene and cleavage of the Cas9 or Cpf1 RNA-guided nuclease recognition site of the activatable reporter cassette, thereby producing cells that express the upstream selectable marker gene; and
  (c) contacting cells of (b) that express the upstream selectable marker gene with a selection agent associated with the downstream selectable marker gene, under conditions that result in death of cells that do not express the downstream selectable marker gene, thereby producing cells that express the downstream selectable marker gene.

* * * * *

UNITED STATES PATENT AND TRADEMARK OFFICE
CERTIFICATE OF CORRECTION

PATENT NO. : 11,254,928 B2
APPLICATION NO. : 16/070406
DATED : February 22, 2022
INVENTOR(S) : Maresca et al.

Page 1 of 1

It is certified that error appears in the above-identified patent and that said Letters Patent is hereby corrected as shown below:

In the Claims

Column 100, Lines 28-30 (Claim 9): "The isolated cell of claim 7, wherein the construct further comprises a nucleic acid encoding the Cas9 or Cpf1 RNA-guided nuclease."

Should be replaced with: –The isolated cell of claim 8, wherein the construct further comprises a nucleic acid encoding the Cas9 or Cpf1 RNA-guided nuclease.–

Signed and Sealed this
Twenty-sixth Day of July, 2022

Katherine Kelly Vidal
*Director of the United States Patent and Trademark Office*